(12) United States Patent
Takakura et al.

(10) Patent No.: US 10,400,251 B2
(45) Date of Patent: Sep. 3, 2019

(54) VIRUS-RESISTANT TOBACCO AND METHOD FOR CREATING SAME

(71) Applicant: JAPAN TOBACCO INC., Tokyo (JP)

(72) Inventors: Yoshimitsu Takakura, Tokyo (JP); Kazuharu Koga, Tokyo (JP); Akira Shinjo, Tokyo (JP); Hisashi Udagawa, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 146 days.

(21) Appl. No.: 15/387,182

(22) Filed: Dec. 21, 2016

(65) Prior Publication Data

US 2017/0107533 A1 Apr. 20, 2017

Related U.S. Application Data

(63) Continuation of application No. PCT/JP2015/068713, filed on Jun. 29, 2015.

(30) Foreign Application Priority Data

Jun. 27, 2014 (JP) ................................. 2014-133378
Sep. 24, 2014 (JP) ................................. 2014-194424

(51) Int. Cl.
| | | |
|---|---|---|
| *C12N 15/82* | (2006.01) | |
| *A01H 1/00* | (2006.01) | |
| *A01H 1/06* | (2006.01) | |
| *A01H 5/00* | (2018.01) | |
| *C12N 15/01* | (2006.01) | |
| *C12N 15/113* | (2010.01) | |
| *A01H 5/12* | (2018.01) | |
| *C12Q 1/6895* | (2018.01) | |

(52) U.S. Cl.
CPC .......... *C12N 15/8283* (2013.01); *A01H 1/00* (2013.01); *A01H 1/06* (2013.01); *A01H 5/00* (2013.01); *A01H 5/12* (2013.01); *C12N 15/01* (2013.01); *C12N 15/113* (2013.01); *C12N 15/821* (2013.01); *C12N 15/8218* (2013.01); *C12N 15/8241* (2013.01); *C12Q 1/6895* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 7,772,462 | B2 | 8/2010 | Jahn et al. |
|---|---|---|---|
| 8,298,819 | B2 | 10/2012 | Takakura et al. |
| 2006/0294618 | A1 | 12/2006 | Jahn et al. |
| 2013/0056014 | A1 | 3/2013 | Noguchi et al. |
| 2013/0117879 | A1 | 5/2013 | Walsh et al. |
| 2017/0107533 | A1 | 4/2017 | Takakura et al. |

FOREIGN PATENT DOCUMENTS

| CN | 101397569 A | 4/2009 |
|---|---|---|
| EP | 2208788 A1 | 7/2010 |
| NZ | 551521 A | 9/2009 |
| WO | WO 2005/118850 A1 | 12/2005 |
| WO | WO 2011/02394 A1 | 8/2011 |
| WO | WO 2015/199242 A1 | 12/2015 |

OTHER PUBLICATIONS

Gong, D., "Important Tobacco Genes: 1. Tobacco Disease Restistance Related Genes," Chinese Tobacco Science (2014), vol. 35, No. 1, pp. 133-135.
Jinpeng et al., "Cloning of PVY Associated Gene eIF4E and Construction of Its Corresponding RNAi Vectors," Chinese Agricultural Science Bulletin (2012), vol. 28, No. 18, pp. 189-193.
Julio et al., "Characterization of PVY (Potato Virus Y) resistance in tobacco: potential role of an eIF4E gene identified by high through-put sequencing technologies," International Plant & Animal Genome Conference XXI (2013).
Office Action dated Apr. 23, 2018, in Chinese Patent Application No. 201580035068.6.
Extended European Search Report dated Nov. 21, 2017, in European Patent Application No. 15811561.8.
Freire, M.A., "Potyviral VPg and HC-Pro Proteins and the Cellular Translation Initiation Factor eIF(iso)4E Interact with Exoribonuclease Rrp6 and a Small α-Heat Shock Protein," Plant Mol. Biol. Rep. (2014), vol. 32, pp. 596-604.
Agarwal et al., "Advances in molecular marker techniques and their applications in plant sciences," Plant Cell Rep., vol. 27, No. 4, 2008 (published online Feb. 2, 2008), pp. 617-631.
Ala-Poikela et al., "Helper Component Proteinase of the Genus Potyvirus Is an Interaction Partner of Translation Initiation Factors eIF(iso)4E and eIF4E and Contains a 4E Binding Motif," J Virol., vol. 85, No. 13, Jul. 2011 (published ahead of print on Apr. 27, 2011), pp. 6784-6794.
Albar et al., "Mutations in the eIF(iso)4G translation initiation factor confer high resistance of rice to Rice yellow mottle virus," Plant J., vol. 47, No. 3, 2006, pp. 417-426.
Altschul et al., "Basic local alignment search tool," J. Mol. Biol., vol. 215, No. 3, 1990, pp. 403-410.
Baker et al., "Nonsense-mediated mRNA decay: terminating erroneous gene expression," Current Opinion in Cell Biology, vol. 16, No. 3, 2004, pp. 293-299.

(Continued)

*Primary Examiner* — Elizabeth F McElwain
(74) *Attorney, Agent, or Firm* — Birch, Stewart, Kolasch & Birch, LLP

(57) ABSTRACT

A virus-resistant tobacco in accordance with the present invention is such that it includes a mutation in a translation initiation factor eIF(iso)4E gene, the mutation causing production of an eIF(iso)4E protein which is non-functional with respect to a virus or suppressing expression of the eIF(iso)4E gene, or a virus-resistant tobacco in accordance with the present invention is such that an expression level of the eIF(iso)4E gene is 20% or lower as compared to a wild type.

18 Claims, 2 Drawing Sheets
Specification includes a Sequence Listing.

(56) References Cited

OTHER PUBLICATIONS

Belhaj et al., "Plant genome editing made easy: targeted mutagenesis in model and crop plants using the CRISPR/Cas system," Plant Methods, vol. 9, No. 39, Oct. 11, 2013, pp. 1-10.
Boiteux et al., "Breeding for Resistance to Viral Diseases," Plant Breeding for Biotic Stress Resistance, Springer-Verlag Berlin Heidelberg, 2012, pp. 57-79.
Brogna et al., "Nonsense-mediated mRNA decay (NMD) mechanisms," Nat. Structural Mol. Biol., vol. 16, No. 2, Feb. 2009 (published online Feb. 4, 2009), pp. 107-113.
Cavatorta et al.., "Engineering virus resistance using a modified potato gene," Plant Biotechnology Journal, vol. 9, No. 9, 2011, pp. 1014-1021.
Combe et al., "Translation initiation factors eIF4E and eIFiso4E are required for polysome formation and regulate plant growth in tobacco," Plant Molecular Biology, vol. 57, No. 5, 2005, pp. 749-760.
De Bruin, "Sources of resistance in the genus Nicoliana to the virus causing bushy top disease in tobacco," Phytophylactica, vol. 22, No. 2, 1990, pp. 263-264.
Decroocq of al., "Multiple Resistance Traits Control Plum pox virus Infection in *Arabidopsis thaliana*," Molecular Plant-Microbe Interactions, vol. 19, No. 5, 2006, pp. 541-549.
Dunoyer et al., "A cysteine-rich plant protein potentiates Polyvirus movement through an interaction with the virus genome-linked protein VPg," Journal of Virology, vol. 78, No. 5, Mar. 2004, pp. 2301-2309 (10 pages).
Durai et al., "Zinc finger nucleases: custom-designed molecular scissors for genome engineering of plant and mammalian cells," Nucleic Acids Res., vol. 33, No. 18, 2005 (published online Oct. 26, 2005), pp. 5978-5990.
Hellens et al., "pGreen: a versatile and flexible binary Ti vector for Agrobacterium-mediated plant transformation," Plant Mol. Biol., vol. 42, No. 6, 2000, pp. 819-832.
Hipper et al., "Viral and cellular factors involved in Phloem transport of plant viruses," Frontier's in Plant Science, vol. 4, Article 154, May 24, 2013, pp. 1-24.
Huang et al., "A host RNA helicase-like protein, AtRH8, interacts with the polyviral genome-linked protein, VPg, associates with the virus accumulation complex, and is essential for infection," Plant Physiol., vol. 152, No. 1, Jan. 2010, pp. 255-266.
Hwang et al., "Translation elongation factor 1B (eEF1B) is an essential host factor for Tobacco mosaic virus infection in plants," Virology, vol. 439, No. 2, May 2013, pp. 1-10.
International Search Report (Form PCT/ISA/210), dated Oct. 6, 2015, for International Application No. PCT/JP2015/068713.
Julio et al., "Characterization of PVY (Potato Virus Y) Resistance in Tobacco: Potential Role of an eIF4E Gene Identified by High Throughput Sequencing Technologies," 2013 CORESTA Joint Study Groups Meeting—Agro-Phyto Abstracts, AP 29, p. 30.
Jung of al., "Exploring natural variations in eIF4E and screening for potyviral resistance in diverse *Nicotiana* species," Hort. Environ. Biotechnol., vol. 54, No. 5, 2013, pp. 430-440.
Komari et al., "Binary vectors and super-binary vectors," Methods in Mol. Biol., vol. 343, 2006, pp. 15-41.
Lellis et al., "Loss-of-susceptibility mutants of *Arabidopsis thaliana* reveal an essential role for eIF(iso)4E during polyvirus infection," Current Biology, vol. 12, No. 12, Jun. 25, 2002, pp. 1046-1051.
Lusser et al., "Deployment of new biotechnologies in plant breeding," Nature Biotechnology, vol. 30, No. 3, Mar. 2012, pp. 231-239.
Masuta et al., "A Single Amino Acid Change in Viral Genome-Associated Protein of Potato Virus Y Correlates with Resistance Breaking in 'Virgin A Mutant' Tobacco," Phytopathology, vol. 89, No. 2, 1999, pp. 118-123 (12 pages).
Mazier et al., "Knock-Down of Both eIF4E1 and eIF4E2 Genes Confers Broad-Spectrum Resistance against Polyviruses in Tomato," PLoS ONE, vol. 6, issue 12, e29595, Dec. 29, 2011, pp. 1-10.
Mo et al., "Complete nucleotide sequence and genome organization of a Chinese isolate of tobacco bushy top virus," Archives of Virology, vol. 148, No. 2, 2003 (published online Nov. 18, 2002), pp. 389-397.
Neff et al., "dCAPS, a simple technique for the genetic analysis of single nucleotide polymorphisms: experimental applications in *Arabidopsis thaliana* genetics," Plant J., vol. 14, No. 3, 1998, pp. 387-392.
Neff et al., "Web-based printer design for single nucleotide polymorphism analysis," Trends in Genetics, vol. 18, No. 12, Dec. 2002 (published online Nov. 1, 2002), pp. 613-615.
Nieto et al., "An eIF4E allele confers resistance to an uncapped and non-polyadenylated RNA virus in melon," The Plant Journal, vol. 48, No. 3, 2006, pp. 452-462.
Oh et al., "Oligonucleotide-directed plant gene targeting," Current Opinion in Biotechnology, vol. 12, No. 2, 2001, pp. 169-172.
Piron at al., "An induced Mutation in Tomato eIF4E Leads to Immunity to Two Polyviruses," PLoS ONE, vol. 5, Issue 6, e11313, Jun. 25, 2010, pp. 1-10 (20 pages).
Pulcinelli et al., "Reporting a source of PVY$^{ntn}$ resistance in *Nicotiana tabacum* L.," Souza Cruz, CORESTA, 2009 Joint Study Groups Meeting, Rovinj, Croatia, 2009, 32 pages.
Robaglia et al., "Translation initiation factors: a weak link in plant RNA virus infection," Trends in Plant Science, vol. 11, No. 1, Jan. 2006 (available online Dec. 15, 2005), pp. 40-45.
Ruffel et al., "A natural recessive resistance gene against potato virus Y in pepper corresponds to the eukaryotic initiation factor 4E (eIF4E)," Plant J., vol. 32, No. 6, 2002, pp. 1067-1075.
Ruffel of al., "Simultaneous mutations in translation initiation factors eIF4E and eIF(iso)4E are required to prevent pepper veinal mottle virus infection of pepper," J Gen Virol., vol. 87, 2006, pp. 2089-2098.
Sato et al., "Host factors and its relevance to virus infection in plants," Virus, vol. 56, No. 2, Dec. 2006, pp. 155-164, with an English abstract.
Sato et al., "Selective involvement of members of the eukaryotic initiation factor 4E family in the infection of *Arabidopsis thaliana* by polyviruses," FEBS Letters, vol. 579, No. 5, 2005 (available online Jan. 19, 2005), pp. 1167-1171.
Tajima et al., "Construction of Mutant Panel in *Nicotiana tabacum* L.," Japanese Journal of Phytopathology, vol. 77, No. 3, Aug. 2011, p. 258 (2 pages), with a partial English translation.
Truniger et al., "Recessive resistance to plant viruses," Adv Virus Res., vol. 75, 2009, pp. 119-159 (42 pages).
Vincentz et al., "Constitutive expression of nitrate reductase allows normal growth and development of Nicotiana plumbaginifolia plants," EMBO J., vol. 10, No. 5, 1991, pp. 1027-1035.
Wang et al., "Silencing of the Host Factor eIF(iso)4E Gene Confers Plum Pox Virus Resistance in Plum," PLoS ONE, vol. 8, issue 1, e50627, Jan. 28, 2013, pp. 1-12 (24 pages).
Wesley et al., "Construct design for efficient, effective and high-throughput gene silencing in plants," Plant J., vol. 27, No. 6, 2001, pp. 581-590.
Yoshii et al., "The *Arabidopsis* Cucumovirus Multiplication 1 and 2 Loci Encode Translation initiation Factors 4E and 4G," J Virol., vol. 78, No. 12. Jun. 2004, pp. 6102-6111 (11 pages).
Zhang et al., "Transcription activator-like effector nucleases enable efficient plant genome engineering," Plant Physiology, vol. 161, No. 1, Jan. 2013, pp. 20-27.
Zhu et al., "Targeted manipulation of maize genes in vivo using chimeric RNA/DNA oligonucleotides," Proc. Natl. Acad. Sci. USA, vol. 96, No. 15, Jul. 1999, pp. 8768-8773.
Jinpeng et al., "Cloning of PVY Associated Gene eIF4E and Construction of Its Corresponding RNAi Vectors," Chinese Agricultural Science Bulletin (2012), vol. 28, No. 18, pp. 189-193.
Henderson et al., "A Severe Virus Disease of Tobacco in Montgomery County, Virginia," Plant Disease Reporter, vol. 47, No. 3, Mar. 15, 1963, pp. 187-189.
International Preliminary Report on Patentability and Written Opinion of the International Searching Authority for International Application No. PCT/JP2017/030492, dated Mar. 7, 2019.
International Search Report, dated Nov. 28, 2017, for International Application No. PCT/JP2017/030492.

(56) References Cited

OTHER PUBLICATIONS

Julio et al., "A Eukaryotic Translation Initiation Factor 4E (eIF4E) is Responsible for the "va" Tobacco Recessive Resistance to Potyviruses," Plant Mol Biol Rep, vol. 33, 2015, pp. 609-623.

Julio et al., "Nicotiana tabacum eukaryotic translation initiation factor 4E (eIF4E) mRNA, complete cds," GenBank, Accession No. KF155696.1, Sep. 15, 2015, 1 page.

Julio et al., "Nicotiana tabacum isolate T021658 eukaryotic initiation factor 4E mRNA, complete cds," GenBank, Accession No. KM202068.1, Sep. 15, 2015, 1 page.

Yamamoto, "Studies on Breeding of Tobacco Varieties Resistant to Veinal Necrosis Disease by Potato Virus Y Strain T," Bulletin of the Leaf Tobacco Research Laboratory, No. 2, Mar. 1992, pp. 78-79.

… (1)

VIRUS-RESISTANT TOBACCO AND METHOD FOR CREATING SAME

CROSS-REFERENCE TO RELATED APPLICATIONS

This application is a Continuation of PCT International Application No. PCT/JP2015/068713 filed in Japan on Jun. 29, 2015, which claims the benefit of Patent Applications No. 2014-133378 filed in Japan on Jun. 27, 2014 and No. 2014-194424 filed in Japan on Sep. 24, 2014, the entire contents of which are hereby incorporated by reference.

TECHNICAL FIELD

The present invention relates to virus-resistant tobacco and a method for producing the virus-resistant tobacco.

BACKGROUND ART

The genus Potyvirus, which is the largest group of plant viruses, has a broad host range. Potato virus Y (hereinafter referred to as PVY), which is a virus that belongs to the genus Potyvirus, can non-persistently transmit through aphids and infect a variety of solanaceous plant species. When it comes to tobacco, PVY causes symptoms such as reduced plant height and vein necrosis. This results in decreases in quality and yield of leaf tobacco and thus causes great damage to tobacco production in the world. From leaf tobacco infected with PVY and decreased in quality, tobacco products with significantly decreased quality are produced.

Meanwhile, Tobacco bushy top virus (hereinafter referred to as TBTV), which is a virus that belongs to the genus Umbravirus, is known as a causative virus for tobacco bushy top disease that has occurred in Africa and Asia. TBTV is persistently transmitted by aphids at a natural environment and causes plant stunting and leaf mottling symptom of tobacco. This results in decreases in quality and yield of tobacco. In particular, the tobacco bushy top disease has become an important disease in African countries.

In tobacco (*Nicotiana tabacum*), Virgin A mutant (hereinafter referred to as VAM), which is a genetic resource exhibiting resistance to PVY, is known and has been frequently utilized in a tobacco breeding program. However, the VAM-Breaking strain (PVY-Breaking strain which can also be expressed as PVY-B), which is a new strain of PVY to break the resistance of VAM, has recently been reported around the world. Currently, there has been strong demand for tobacco resistant to the VAM-Breaking strain. Recently, tobacco acquiring resistance to the VAM-Breaking strain by gamma-ray irradiation has been reported (Non-Patent Literature 1), but a causative gene has not been identified. Further, some of wild species including, for example, *Nicotiana africana* have been known to exhibit resistance to the PVY-Breaking strain, but have not yet been utilized in a breeding program.

Still further, it has been reported that exploration for resistance sources to tobacco bushy top disease was conducted using 43 types of tobacco varieties and wild species belonging to the genus *Nicotiana*, and none of these tobacco varieties exhibited resistance to tobacco bushy top disease, while several wild species did not show any symptoms of viral diseases (Non-Patent Literature 2). However, the mode of inheritance of resistance of such wild species has not been elucidated, and it is expected that introduction of the resistant trait into the cultivated varieties of *N. tabacum* from the wild species is accompanied by introduction of a trait that adversely affects quality and yield. Therefore, a practical use of them is a long way off.

About half of approximately 200 types of known plant virus-resistance genes are recessively inherited (Non-Patent Literature 3). These genes are considered to be host factors required for, for example, replication and cell-to-cell movement of viruses. Research over the past decade has revealed some of these factors. For example, translation initiation factors such as eIF4E and eIF4G, DEAD-box RNA helicase-like protein (Non-Patent Literature 4), a cysteine-rich VPg-interacting protein (Non-Patent Literature 5), Translation elongation factor (Non-Patent Literature 6), and others have been identified as recessive virus-resistance gene factors. As a matter of course, these factors are not all of the virus-resistance genes. In addition, a number of other factors are considered to be candidates for the virus-resistance genes (Non-Patent Literature 3). Examples of such candidates include various plant factors associated with sieve tube transport of plant viruses (Non-Patent Literature 7).

Viruses utilize translation initiation systems of hosts in the synthesis of viral proteins. In 2002, it was shown that a recessive resistance gene factor against Turnip mosaic virus (TuMV) in *Arabidopsis thaliana* is a mutation of a translation initiation factor eIF(iso)4E (Non-Patent Literature 8). Since then, the association of the eIF4E gene family with recessive resistance to known viruses belonging to the genus Potyvirus has been studied in some plants. In fact, it has been shown that recessive virus-resistance is acquired by an artificial mutation of eIF4E or eIF(iso)4E.

For example, Patent Literature 1 describes a method of imparting virus resistance by suppressing the eIF4E gene (not including eIF(iso)4E) function. Further, Patent Literature 2 describes a mutant plant having eIF4E or eIF(iso)4E not be acted upon by a virus, by splicing mutation of the eIF4E gene or eIF(iso)4E gene. The mutation is insertion, deletion, or substitution of at least one base in a non-coding region of eIF4E or eIF(iso)4E or in a splicing element (a region containing ±10 bases from a boundary site between an exon and an intron) of eIF4E or eIF(iso)4E, and the mutation is intended to occur preferably in an intron, and more preferably in a first intron. Still further, Patent Literature 3 describes a method involving selection of pepper veinal mottle disease (Pepper veinal mottle virus (PVMV)) resistant plant by combination of mutations both in eIF4E and in eIF(iso)4E, and specifically describes a method of selecting a plant in which eIF4E and eIF(iso)4E are not expressed at all, but mutated eIF4E does express.

Yet further, it has been shown that, for example, a causative gene in recessive resistance to PVY in pepper is eIF4E (Non-Patent Literature 9). In addition, it has been shown that Clover yellow vein virus proliferates in eIF(iso)4E-deficient *Arabidopsis thaliana*, but does not proliferate in eIF4E-deficient *Arabidopsis thaliana*, and, on the contrary, TuMV proliferates in the eIF4E-deficient *Arabidopsis thaliana*, but does not proliferate in the eIF(iso)4E-deficient *Arabidopsis thaliana* (Non-Patent Literature 10). Further, in order to acquire resistance to PVMV, both eIF4E and eIF(iso)4E must lose their functions simultaneously (Non-Patent Literature 11). For example, Non-Patent Literature 12, Non-Patent Literature 13, and others have reviewed recent translation initiation factors and plant viral resistance.

Association between a limited number of viruses other than the viruses belonging to the genus Potyvirus and translation initiation factors have also been pointed out. For example, Cucumber mosaic virus (CMV) is a virus belonging to the genus Cucumovirus. Production of 3a protein that is associated with cell-to-cell movement of CMV is inhibited in *Arabidopsis thaliana* in which eIF4E or eIF4G is destroyed. In addition, Rice yellow mottle virus (RYMV) is a virus belonging to the genus Sobemovirus. Rice in which eIF(iso)4G has a mutation is resistant to RYMV (Non-Patent Literature 14 and Non-Patent Literature 15).

As for a tomato, which is a solanaceous plant as is the case with tobacco, a relationship between Potyvirus resistance and a translation initiation factor eIF4E has been studied based on an exhaustive analysis of a tomato mutant panel. In the study, it has been shown that suppression of the function of eIF4E1, which is a member of the eIF4E gene family, imparts resistance to PVY and Pepper mottle virus (PepMoV), but does not impart resistance to Tobacco etch virus (TEV) (Non-Patent Literature 16). It has also been shown together that suppression of the function of eIF4E2, eIF(iso)4E, eIF4G, or eIF(iso)4G do not impart resistance to these viruses belonging to the genus Potyvirus. It has also been shown that simultaneous suppression of the functions of eIF4E1 and eIF4E2 by using RNAi (RNA interference) imparts resistance to seven types of viruses belonging to the genus Potyvirus, including PVY, PepMoV and TEV. However, interestingly, it has been shown that suppression of the function of eIF(iso)4E by RNAi does not impart resistance to any of these viruses (Non-Patent Literature 17). It has also been shown together that eIF(iso)4E of tomato is not associated with resistance to viruses other than the viruses belonging to the genus Potyvirus (Non-Patent Literature 17).

Thus, an association between PVY resistance and eIF4E in any plant has been pointed out so far, but an association between PVY resistance and eIF(iso)4E has never been reported. Although eIF(iso)4E is categorized into the eIF4E family, DNA sequence identity between eIF4E and eIF(iso)4E in plants is generally less than 60%. In addition, eIF(iso)4E forms a translation complex different from that formed by eIF4E. Specifically, eIF(iso)4E, together with eIF(iso)4G, forms a translation complex eIF(iso)4F, while eIF4E, together with eIF4G, forms a translation complex eIF4F.

As for tobacco (*Nicotiana tabacum*), reduction of an expression level of eIF4E1 or eIF(iso)4E has been reported (Non-Patent Literature 18). In this report, the transcription of eIF4E1 or eIF(iso)4E of tobacco is suppressed by using antisense technology. Non-Patent Literature 18 describes that production of tobacco in which the amount of transcripts of eIF4E1 is suppressed to 30% to 40% relative to a control and tobacco in which the amount of transcripts of eIF(iso)4E is suppressed to 60% relative to a control and that in a crossbreed progeny between both of the above tobaccos, the amount of transcripts of eIF4E1 is reduced to 26% relative to a control, and the amount of transcripts of eIF(iso)4E is reduced to 31% relative to a control. However, Non-Patent Literature 18 does not describe association with viral resistance at all. Further, the possibility that HC-Pro protein of PVY interacts with eIF(iso)4E of tobacco has been suggested from an assay system using *Nicotiana benthamiana* (Non-Patent Literature 19). However, Non-Patent Literature 19 has not pointed out association with resistance.

Further, as for tobacco, it has been found from a comprehensive analysis of transcripts of PVY-resistant VAM tobacco and transcripts of PVY-sensitive tobacco that the level of transcripts of eIF4E gene is specifically low in VAM tobacco, and indeed, it has been shown that tobacco having a mutation in this gene becomes PVY resistance (Non-Patent Literature 20).

On the contrary, it has been reported that there is no association between Potyvirus resistance of tobacco and mutations in the translation initiation factors eIF4E and eIF(iso)4E (Non-Patent Literature 21). This report has investigated base sequences of eIF4E and eIF(iso)4E genes in varieties resistant to PVY and PepMoV, which are viruses belonging to the genus Potyvirus and can infect tobacco, and in varieties sensitive to these viruses. As a result, it has been shown that an association between mutations that occurred in both of the genes and resistance and sensitivity to the viruses was not observed. For example, while no mutations were detected in the eIF4E gene and eIF(iso)4E gene of a certain PVY-resistant variety, mutations were observed in those of a PVY-sensitive variety. In similar experiments conducted on other plants in the past, mutations were detected in eIF4E and eIF(iso)4E genes of a PVY-resistant variety, and the PVY resistance was attributed to such mutations. Thus, Non-Patent Literature 21 concludes that, in tobacco, unlike other solanaceous plants, there is no association between the PVY resistance and the translation initiation factors eIF4E and eIF(iso)4E. As discussed above, as for tobacco, unlike other plants, the issue of an association between Potyvirus resistance and the translation initiation factors is still in chaos.

Furthermore, an association between the translation initiation factors and resistance to viruses belonging to the genus Umbravirus is not known at all in any plant species including tobacco.

Tobacco (*Nicotiana tabacum*), which is an amphidiploid, has a larger number of genes than a normal diploid plant. In tobacco, basically one pair of genes derived from *Nicotiana sylvestris* and one pair of genes derived from *Nicotiana tomentosiformis* are present. That is, in tobacco, at least two pairs of homologous genes are present. Therefore, the mode of inheritance of tobacco is more complicated than that of diploid plants. In *Arabidopsis thaliana*, three types of eIF4E and one type of eIF(iso)4E are supposed to be present (Non-Patent Literature 12). In tobacco, translation initiation factors, which are observed in tobacco, are considered to be all present in pairs. It has been found that an eIF4E family of tobacco has at least 12 members including even a cap-binding protein functionally similar to eIF4E (Non-Patent Literature 20). The members of the gene family of tobacco translation initiation factors are much larger in number when further including even eIF4G and eIF(iso)4G.

CITATION LIST

Patent Literatures

[Patent Literature 1]
Specification of U.S. Pat. No. 7,772,462
[Patent Literature 2]
Specification of U.S. Patent Application Publication No. 2013/117879
[Patent Literature 3]
International Publication No. WO 2005/118850
[Non-Patent Literatures]
[Non-Patent Literature 1]
Pulcinelli et al. (2009) Reporting a source of PVYntn resistance in *Nicotiana tabacum* L. CORESTA Joint Study Groups Meeting, Rovinj, Croatia.
[Non-Patent Literature 2]
De Bruin. (1990) Sources of resistance in the genus *Nicotiana* to the virus causing bushy top disease in tobacco. Phytophylactica. 22: 263-264.
[Non-Patent Literature 3]
Truniger V, Aranda M A. (2009) Recessive resistance to plant viruses. Adv Virus Res. 75:119-159.

[Non-Patent Literature 4]
Huang et al. (2010) A host RNA helicase-like protein, AtRH8, interacts with the potyviral genome-linked protein, VPg, associates with the virus accumulation complex, and is essential for infection. Plant Physiol. 152: 255-266.
[Non-Patent Literature 5]
Dunoyer et al. (2004) A Cysteine-Rich Plant Protein Potentiates Potyvirus Movement through an Interaction with the Virus Genome-Linked Protein VPg. J. Virol. 78: 2301-2309.
[Non-Patent Literature 6]
Hwang et al. (2013) Translation elongation factor 1B (eEF1B) is an essential host factor for Tobacco mosaic virus infection in plants. Virology 439:105-114.
[Non-Patent Literature 7]
Hipper et al. (2013) Viral and cellular factors involved in Phloem transport of plant viruses. Front Plant Sci. 4: article 154.
[Non-Patent Literature 8]
Lellis et al. (2002) Loss-of-susceptibility mutants of *Arabidopsis thaliana* reveal an essential role for eIF(iso)4E during potyvirus infection. Curr Biol. 12:1046-1051.
[Non-Patent Literature 9]
Ruffel et al. (2002) A natural recessive resistance gene against potato virus Y in pepper corresponds to the eukaryotic initiation factor 4E (eIF4E). Plant J. 32, 1067-1075.
[Non-Patent Literature 10]
Sato et al. (2005) Selective involvement of members of the eukaryotic initiation factor 4E family in the infection of *Arabidopsis* thalianaby potyviruses. FEBS Lett. 579: 1167-1171.
[Non-Patent Literature 11]
Ruffel et al. (2006) Simultaneous mutations in translation initiation factors eIF4E and eIF(iso)4E are required to prevent pepper veinal mottle virus infection of pepper. J Gen Virol. 87, 2089-2098.
[Non-Patent Literature 12]
Robaglia and Caranta. (2006) Trends in Plant Science 11:40-45.
[Non-Patent Literature 13]
Leonardo et al. (2012) Breeding for resistance to viral diseases. In Fritsche-Neto and Borem. (2012) Plant breeding for biotic stress resistance. Springer-Verlag Berlin Heidelberg.
[Non-Patent Literature 14]
Yoshii et al. (2004) The *Arabidopsis* Cucumovirus Multiplication 1 and 2 Loci Encode Translation Initiation Factors 4E and 4G. J Virol. 78: 6102-6111.
[Non-Patent Literature 15]
Albar et al. (2006) Mutations in the eIF(iso)4G translation initiation factor confer high resistance of rice to Rice yellow mottle virus. Plant J. 47:417-426.
[Non-Patent Literature 16]
Piron et al. (2010) PLOS ONE 5: e11313.
[Non-Patent Literature 17]
Mazier et al. (2011) PLOS ONE 6: e29595.
[Non-Patent Literature 18]
Combe et al. (2005) Translation initiation factors eIF4E and eIFiso4E are required for polysome formation and regulate plant growth in tobacco. Plant Molecular Biology 57: 749-760.
[Non-Patent Literature 19]
Ala-Poikela et al. (2011) Helper Component Proteinase of the Genus Potyvirus Is an Interaction Partner of Translation Initiation Factors eIF(iso)4E and eIF4E and Contains a 4E Binding Motif. J Virol. 85: 6784-6794.
[Non-Patent Literature 20]
Julio et al. (2013) Characterisation of PVY (Potato Virus Y) resistance in tobacco: potential role of an eIF4E gene identified by high throughput sequencing technologies. CORESTA Meeting Agro-Phyto Groups abstr. AP 29.
[Non-Patent Literature 21]
Jung and Yearn. (2013) Exploring Natural Variations in eIF4E and Screening for Potyviral Resistance in Diverse *Nicotiana* Species. Hort. Environ. Biotechnol. 54:430-440.

SUMMARY OF INVENTION

Technical Problem

Although tobacco having resistance to the PVY-Breaking strain has been known, it is only one case, as discussed earlier. Besides, persistence of the resistance of such tobacco is unknown. Therefore, in order to avoid a potential genetic vulnerability, the development of another novel tobacco having resistance to viruses including the PVY-Breaking strain is an urgent necessity. Further, a gene involved in the resistance has still remained unidentified. This has been a stumbling block for a precise marker breeding.

Additionally, as for TBTV, exploration for TBTV-resistant varieties through the cultivars was performed. However, any varieties exhibiting resistance to TBTV were not found. Later, the development of TBTV-resistant varieties was not performed.

The present invention has been attained in view of the above problems, and it is a main object of the present invention to provide tobacco having resistance to a virus and a method for producing the tobacco.

Solution to Problem

An aspect of a virus-resistant tobacco in accordance with the present invention includes a mutation in a translation initiation factor eIF(iso)4E gene, the mutation causing production of a translation initiation factor eIF(iso)4E protein which is non-functional with respect to a virus or suppressing expression of the translation initiation factor eIF(iso)4E gene.

Another aspect of the virus-resistant tobacco in accordance with the present invention is such that an expression level of a translation initiation factor eIF(iso)4E gene is 20% or lower, as compared to a wild type.

An aspect of a method for producing a virus-resistant tobacco in accordance with the present invention, includes introducing a mutation to a translation initiation factor eIF(iso)4E gene, the mutation causing production of a translation initiation factor eIF(iso)4E protein which is non-functional with respect to a virus or suppressing expression of the translation initiation factor eIF(iso)4E gene, in order to produce tobacco having resistance to a virus.

Another aspect of the method for producing a virus-resistant tobacco in accordance with the present invention includes introducing a factor that suppresses an expression level of a translation initiation factor eIF(iso)4E gene to 20% or lower as compared to a wild type, in order to produce tobacco having resistance to a virus.

An aspect of a detection-use polynucleotide in accordance with the present invention is a polynucleotide for detecting a mutation in a translation initiation factor eIF(iso)4E gene of tobacco, the mutation causing production of a translation initiation factor eIF(iso)4E protein which is non-functional with respect to a virus or suppressing expression of the translation initiation factor eIF(iso)4E gene.

An aspect of a DNA marker for evaluating tobacco for resistance to a virus in accordance with the present invention, includes: a polynucleotide consisting of a continuous base sequence which contains a mutation in a translation initiation factor eIF(iso)4E gene or a sequence complementary to the continuous base sequence, the mutation causing production of a translation initiation factor eIF(iso)4E protein which is non-functional with respect to a virus or suppressing expression of the translation initiation factor eIF(iso)4E gene.

Advantageous Effects of Invention

The present invention enables provision of tobacco having resistance to a virus.

DESCRIPTION OF EMBODIMENTS

[1. Virus-Resistant Tobacco and Method for Producing the Virus-Resistant Tobacco]

An aspect of the present invention relates to tobacco having resistance to a virus (a virus-resistant tobacco) and more specifically to a virus-resistant tobacco such that an expression level (e.g., the amount of transcripts) of a translation initiation factor eIF(iso)4E gene which is functional with respect to a virus is reduced in a cell. Further, another aspect of the present invention relates to a method for producing tobacco having resistance to a virus (a method for producing a virus-resistant tobacco) and more specifically to a method for producing a virus-resistant tobacco by reducing an expression level (e.g., the amount of transcripts) of an eIF(iso)4E gene which is functional with respect to a virus in a cell.

Figure 2:
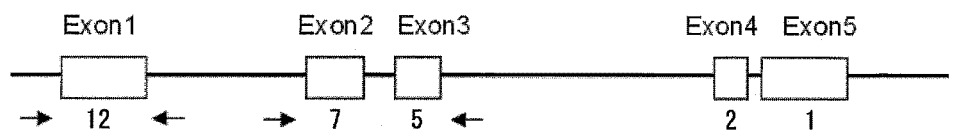
FIG. 2 is a diagram illustrating a gene structure of an S-type (derived from *Nicotiana sylvestris*) eIF(iso)4E of tobacco (*Nicotiana tabacum*).
Figure 3:
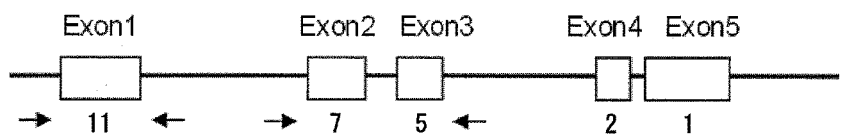
FIG. 3 is a diagram illustrating a gene structure of a T-type (derived from *Nicotiana tomentosiformis*) eIF(iso)4E of tobacco (*Nicotiana tabacum*).

*Nicotiana tabacum*, which is an amphidiploid, has both an S-type genome and a T-type genome derived from *Nicotiana sylvestris* and *Nicotiana tomentosiformis*, respectively, each of which is an ancestor species thereof. Thus, *N. tabacum* has two pairs of eIF(iso)4E genes (alleles) with different base sequences. Both the S-type eIF(iso)4E gene and T-type eIF(iso)4E gene of *N. tabacum*, as indicated in FIGS. 2 and 3, respectively, have five exons and four introns. Note that, in FIGS. 2 and 3, numbers provided in lower parts of FIGS. 2 and 3 indicate the numbers of positions at which potential nonsense mutations occur, and arrows indicate the positions of primers in the Examples. An example of a cDNA sequence of an S-type, wild-type eIF(iso)4E gene is represented by SEQ ID NO: 1 (GenBank accession number: AY699609). In SEQ ID NO: 1, an open reading frame is 70th to 672nd bases. An example of a cDNA sequence of a T-type, wild-type eIF(iso)4E gene is represented by SEQ ID NO: 2 (GenBank accession number: EB683576). In SEQ ID NO: 2, an open reading frame is 37th to 624th bases. Further, an example of an amino acid sequence of an S-type, wild-type eIF(iso)4E protein is represented by SEQ ID NO: 3. An example of an amino acid sequence of a T-type, wild-type eIF(iso)4E protein is represented by SEQ ID NO: 4. Further, an example of an mRNA sequence (which contains "u" instead of "t" in a cDNA sequence) of an S-type, wild-type eIF(iso)4E gene is represented by SEQ ID NO: 5. An example of an mRNA sequence (which contains "u" instead of "t" in a cDNA sequence) of a T-type, wild-type eIF(iso)4E gene is represented by SEQ ID NO: 6. Further, an example of a base sequence of a genome of an S-type, wild-type eIF(iso)4E gene is represented by SEQ ID NO: 7. An example of a base sequence of a genome of a T-type, wild-type eIF(iso)4E gene is represented by SEQ ID NO: 8. In SEQ ID NO: 7, exons are 132nd to 397th bases (first exon), 1730th to 1898th bases (second exon), 2029th to 2154th bases (third exon), 4723rd to 4785th bases (fourth exon), and 4893rd to 5096th bases (fifth exon). In SEQ ID NO: 8, exons are 164th to 382nd bases (first exon), 1620th to 1788th bases (second exon), 1919th to 2044th bases (third exon), 3205th to 3267th bases (fourth exon), and 3373rd to 3593rd bases (fifth exon).

In a plant, base sequences of protein coding regions of genes having the same function can be different by the order of 1% to several percents between cultivars, depending on a gene, and can be different by the order of several percents to 10% between a cultivar and a wild relative. A wild-type eIF(iso)4E gene before undergoing mutation, herein, encompasses a gene which causes production of mRNA consisting of a base sequence represented by SEQ ID NO: 5 or SEQ ID NO: 6 and a gene which encodes an eIF(iso)4E protein consisting of an amino acid sequence represented by SEQ ID NO: 3 or SEQ ID NO: 4. Further, the wild-type eIF(iso)4E gene before undergoing mutation, herein, encompasses a gene which causes production of mRNA having a sequence identity of 92% or higher, preferably 95% or higher, more preferably 97% or higher, even more preferably 99% or higher with the base sequence represented by SEQ ID NO: 5 or SEQ ID NO: 6 and encodes a functional eIF(iso)4E protein. Still further, the wild-type eIF(iso)4E gene herein encompasses a gene which encodes a functional eIF(iso)4E protein having a sequence identity of 92% or higher, preferably 95% or higher, more preferably 97% or higher, even more preferably 99% or higher with the amino acid sequence represented by SEQ ID NO: 3 or SEQ ID NO: 4. Yet further, the wild-type eIF(iso)4E gene herein encompasses a gene which (i) causes production of mRNA having a base sequence in which 1 to 50 bases, 1 to 40 bases, 1 to 30 bases, 1 to 20 bases, 1 to 15 bases, 1 to 12 bases, 1 to 10 bases, 1 to 8 bases, 1 to 5 bases, 1 to 3 bases, 1 to 2 bases, or one base are/is substituted, deleted, inserted, and/or added in the base sequence represented by SEQ ID NO: 5 or SEQ ID NO: 6 and (ii) encodes a functional eIF(iso)4E protein. Further, the wild-type eIF(iso)4E gene herein encompasses a gene which encodes a functional eIF(iso)4E protein having an amino acid sequence in which 1 to 20 amino acids, 1 to 15 amino acids, 1 to 12 amino acids, 1 to 10 amino acids, 1 to 8 amino acids, 1 to 5 amino acids, 1 to 4 amino acids, 1 to 3 amino acids, 1 to 2 amino acids, or one amino acid are/is substituted, deleted, inserted, and/or added in the amino acid sequence represented by SEQ ID NO: 3 or SEQ ID NO: 4. Unless otherwise specified, any numerical range expressed as "A to B" herein means "not less than A and not greater than B".

For example, a wild-type T-type eIF(iso)4E gene before undergoing mutation, herein, encompasses a gene whose cDNA sequence is identical to the sequence assigned GenBank accession number FN666434. This sequence, which is derived from a T-type eIF(iso)4E gene derived from tobacco variety Samsun NN, has a sequence identity of 97% with cDNA sequence of EB683576 (SEQ ID NO: 2) of a T-type eIF(iso)4E derived from tobacco variety K326. Proteins encoded by these two genes have an amino acid sequence identity (identity) of 97% and an amino acid sequence similarity (similarity) of 99%.

As used herein, the "base sequence identity" refers to the percentage of alignments of bases which match exactly between a plurality of base sequences. The "amino acid sequence identity" refers to the percentage of alignments of amino acids which match exactly between a plurality of amino acid sequences. The "amino acid sequence similarity" refers to the percentage of alignments of amino acids which match exactly or have similar properties between a plurality of amino acid sequences. Examples of amino acids having similar properties are listed as follows. For example, amino acids having a residue with positive charges are lysine, arginine, and histidine, amino acids having a residue with negative charges are asparatic acid and glutamic acid, amino acids having a non-polar residue, i.e., a hydrophobic residue are alanine, valine, leucine, isoleucine, methionine, tryptophan, phenylalanine, and proline, and polar amino acids with no charges are glycine, serine, threonine, cysteine, tyrosine, asparagine, and glutamine. The "base sequence identity", "amino acid sequence identity", "amino acid sequence similarity" can be calculated by using, for example, BLAST (Literature: Altschul et al. (1990) Basic local alignment search tool. J Mol Biol. 215:403-410.), which is a sequence analysis (homology search) program commonly used by those skilled in the art, or by using a commercially available nucleic acid and amino acid analysis software. BLAST search can be performed on a website of, for example, GenBank (www.ncbi.nlm.nih.gov/genbank/) or DNA Data Bank of Japan (www.ddbj.nig.ac.jp/indexj.html). In doing so, various search parameters can be changed, but default values are used normally.

As used herein, the "tobacco" encompasses not only *Nicotiana tabacum* but also other species of the same genus *Nicotiana*. Examples of other species of the genus *Nicotiana* include *N. paniculata, N. knightiana, N. solanifolia, N. benavidesii, N. cordifolia, N. raimondii, N. cutleri, N. rustica, N. tomentosa, N. tomentosiformis, N. otophora, N. kawakamii, N. setchellii, N. undulata, N. arentsii, N. wigandioides, N. glutinosa, N. thyrsiflora, N. obtusifolia, N. palmeri, N. langsdorffii, N. alata, N. forgetiana, N. bonariensis, N. longiflora, N. plumbaginifolia, N. azambujae, N. mutabilis, N. sylvestris, N. repanda, N. stocktonii, N. nesophila, N. nudicaulis, N. noctiflora, N. petunioides, N. acaulis, N. ameghinoi, N. glauca, N. paa, N. acuminata, N. pauciflora, N. attenuata, N. longibracteata, N. miersii, N. corymbosa, N. linearis, N. spegazzinii, N. quadrivalvis, N. clevelandii, N. benthamiana, N. umbratica, N. cavicola, N. debneyi, N. gossei, N. amplexicaulis, N. maritima, N. velutina, N. hesperis, N. occidentalis, N. simulans, N. megalosiphon, N. rotundifolia, N. excelsior, N. suaveolens, N. ingulba, N. exigua, N. goodspeedii, N. rosulata, N. fragrans, N. africana, N. burbidgeae, N. heterantha, N. stenocarpa, N. truncata,* and *N. wuttkei*. Further, the "tobacco" encompasses, for example, a whole tobacco plant, tobacco plant tissues (e.g., a leaf, a stalk, a flower, a root, a reproductive organ, an embryo, and a part thereof), a tobacco seedling, a tobacco seed, a dried tobacco leaf, a dried tobacco stalk, a dried tobacco flower, a dried tobacco root, and a dried tobacco seed.

It is considered that cDNA sequences of eIF(iso)4E genes of these *Nicotiana* plants have a sequence identity of 90% or higher with the base sequence represented by SEQ ID NO: 1. In fact, the base sequence represented by SEQ ID NO: 1 shows a sequence identity of 100% with a cDNA sequence of a eIF(iso)4E gene of *N. sylvestris* (except for introns). The base sequence represented by SEQ ID NO: 2 shows a sequence identity of 99% with a cDNA sequence of eIF(iso)4E of *N. tomentosiformis* (except for introns). The base sequence represented by SEQ ID NO: 1 and base sequence represented by SEQ ID NO: 2 show sequence identities of 98% and 99%, respectively, with a cDNA sequence of eIF(iso)4E of *N. otophora* (except for introns). Further, all of the eIF(iso)4E genes of *N. sylvestris, N. tomentosiformis,* and *N. otophora* have exons (five exons) and introns (four introns) which are numerically equal to exons and introns of the gene of *N. tabacum*.

The base sequence of the wild-type eIF(iso)4E gene can be obtained by using, for example, the BLAST program to perform homology search using the base sequence represented by SEQ ID NO: 1 across genomes (Whole genome shotgun contigs) of *N. sylvestris, N. tomentosiformis,* or *N. otophora*, which are registered in GenBank. Alternatively, a base sequence of an eIF(iso)4E gene of a plant species derived from a plant belonging to the genus *Nicotiana* can be obtained by amplifying the eIF(iso)4E gene from a genomic DNA of the plant species by a PCR method using, for example, a primer sequence represented by SEQ ID NO: 25 to SEQ ID NO: 36, and then determining a base sequence of PCR products. The homology search may be performed by using the BLAST program or may be performed by using a commercially available nucleic acid and amino acid analysis software.

Further, from a genomic library or cDNA library of tobacco wild species, a base sequence of an eIF(iso)4E gene of the tobacco wild species can be obtained by performing a hybridization experiment under stringent conditions with use of the base sequence represented by SEQ ID NO: 1 or SEQ ID NO: 2 as a probe.

A virus to which a virus-resistant tobacco shows resistance is not limited to a specific virus. Examples of the virus include viruses with which tobaccos can be infected, such as viruses belonging to the genus Alfamovirus (e.g., Alfalfa mosaic virus), viruses belonging to the genus Curtovirus (e.g., Beet curly top virus), viruses belonging to the genus Begomovirus (e.g., Tobacco leaf curl virus), viruses belonging to the genus Cucumovirus (e.g., Cucumber mosaic virus and Peanut stunt virus), viruses belonging to the genus Ilarvirus (e.g., Tobacco streak virus), viruses belonging to the genus Potyvirus (e.g., Potato virus Y (PVY), Tobacco etch virus, Tobacco vein mottling virus, and Tobacco vein banding mosaic virus), viruses belonging to the genus Tobamovirus (e.g., Tobacco mosaic virus), viruses belonging to the genus Tobravirus (e.g., Tobacco rattle virus), viruses belonging to the genus Necrovirus (e.g., Tobacco necrosis virus), viruses belonging to the genus Varicosavirus (e.g., Tobacco stunt virus), viruses belonging to the genus Nepovirus (e.g., Tobacco ringspot virus), viruses belonging to the genus Umbravirus (e.g., Tobacco bushy top virus and Tobacco mottle virus), viruses belonging to the genus Polerovirus (e.g., Tobacco vein distorting virus), viruses belonging to the genus Mastrevirus (e.g., Tobacco yellow dwarf virus), and viruses belonging to the genus Tospovirus (e.g., Tomato spotted wilt virus). A virus-resistant tobacco in accordance with the present invention may have resistance to a species of viruses or may have resistance to two or more species of viruses. A virus-resistant tobacco in accordance with the present invention may have significant resistance to the viruses belonging to the genus Potyvirus. A virus-resistant tobacco in accordance with the present invention can have resistance to viruses in the PVY-O strain, the PVY-C strain, the PVY-Z strain, and the PVY-N strain (including NTN and NW) of Potato virus Y (PVY) in the viruses belonging to the genus Potyvirus and particularly to the PVY strain that breaks virus resistance of Virgin A mutant of tobacco (the VAM-Breaking strain). Further, a virus-resistant tobacco in accordance with the present invention may have significant resistance to the viruses belonging to the genus Umbravirus and particularly to Tobacco bushy top virus (TBTV).

As used herein, "virus resistance" refers to delay or nonoccurrence of a symptom that occurs in tobacco with viral infection, relative to a susceptible tobacco variety. Examples of the symptom that occurs in tobacco include plant stunting, vein necrosis, stem necrosis, vein distorting, and mottling. Alternatively, the "virus resistance" refers to suppression of reproduction/replication of a virus or suppression of cell-to-cell movement of a virus, relative to a susceptible tobacco variety.

(Aspect 1 of Virus-Resistant Tobacco and Method for Producing the Virus-Resistant Tobacco)

An aspect of a virus-resistant tobacco in accordance with the present invention is a virus-resistant tobacco that includes a mutation in an eIF(iso)4E gene, the mutation causing production of a translation initiation factor eIF(iso)4E protein which is non-functional with respect to a virus or suppressing expression of the translation initiation factor eIF(iso)4E gene.

As used herein, the "mutation" refers to point mutation, deletion, insertion, duplication, translocation, and inversion in DNA. Unless otherwise specified, the "mutation" refers to a difference from the wild-type base sequence.

As used herein, the "eIF(iso)4E gene" encompasses, in a genome, not only a coding region that encodes an eIF(iso)4E protein, but also a non-coding region required for expression of the eIF(iso)4E protein, including introns, regulatory regions, and other untranslated sequences.

The "eIF(iso)4E protein which is non-functional with respect to a virus" refers to an eIF(iso)4E protein that cannot be used for self-reproduction or cell-to-cell movement of a virus (the use of that eIF(iso)4E protein is inhibited at least partially), and encompasses both an eIF(iso)4E protein that does not carry the function of a normal eIF(iso)4E protein (as a translation initiation factor) in tobacco and an eIF(iso)4E protein that does carry the function of a normal eIF(iso)4E protein in tobacco, but cannot be used by a virus. As demonstrated in Examples discussed later, the inventors of the present invention have found that, in tobacco, an eIF(iso)4E protein of a wild type (a plant having no mutation introduced thereto) is probably used for self-reproduction or cell-to-cell movement of a virus.

The "expression level of an eIF(iso)4E gene" may be the amount of transcription to an eIF(iso)4E mRNA (the transcription level or the amount of transcripts) and/or the amount of translation to an eIF(iso)4E protein (translational level or the amount of translation products). Thus, the expression that "eIF(iso)4E expression is suppressed" encompasses a case where transcription is suppressed as compared to a wild type, a case where translation is suppressed as compared to a wild type, and a case where both transcription and translation are suppressed as compared to a wild type. Note that the expression that "transcription is suppressed" encompasses a case where transcripts are degraded.

As described above, N. tabacum is considered to have a pair of S-type eIF(iso)4E genes and a pair of T-type eIF(iso)4E genes, which comes to a total of four eIF(iso)4E genes (two S-type eIF(iso)4E genes and two T-type eIF (iso) 4E genes). In one example, it is preferable that a virus-resistant tobacco has a mutation in at least the S-type eIF(iso)4E genes. In this case, the virus-resistant tobacco has resistance to at least the viruses belonging to the genus Umbravirus (e.g., TBTV). In another example, it is preferable that a virus-resistant tobacco has a mutation in at least the T-type eIF(iso)4E genes. In this case, the virus-resistant tobacco has resistance to at least the viruses belonging to the genus Potyvirus (e.g., the PVY-B strain). In still another example, it is more preferable that a virus-resistant tobacco has a mutation in both the S-type eIF(iso)4E genes and the T-type eIF(iso)4E genes. In this case, the virus-resistant tobacco has resistance to at least both the viruses belonging to the genus Umbravirus (e.g., TBTV) and the viruses belonging to the genus Potyvirus (e.g., the PVY-B strain). Further, a mutation in one type of eIF(iso)4E genes may be a homozygous mutation (for example, both of the two S-type eIF(iso)4E genes have mutations) or may be a heterozygous mutation, but is preferably a homozygous mutation.

Thus, an example of a virus-resistant tobacco (i) has one or more mutations in (a) a wild-type eIF(iso)4E gene which encodes an eIF(iso)4E protein consisting of an amino acid sequence represented by SEQ ID NO: 3, (b) a wild-type eIF(iso)4E gene which encodes a functional eIF(iso)4E protein having a sequence identity of 92% or higher with the amino acid sequence represented by SEQ ID NO: 3, (c) a wild-type eIF(iso)4E gene which causes production of mRNA consisting of a base sequence represented by SEQ ID NO: 5, or (d) a wild-type eIF(iso)4E gene which causes production of mRNA having a sequence identity of 92% or higher with the base sequence represented by SEQ ID NO: 5 and encodes a functional eIF(iso)4E protein, and (ii) has resistance to viruses belonging to the genus Umbravirus. Another example of a virus-resistant tobacco (i) has one or more mutations in (a) a wild-type eIF(iso)4E gene which encodes an eIF(iso)4E protein consisting of an amino acid sequence represented by SEQ ID NO: 4, (b) a wild-type eIF(iso)4E gene which encodes a functional eIF(iso)4E protein having a sequence identity of 92% or higher with the amino acid sequence represented by SEQ ID NO: 4, (c) a wild-type eIF(iso)4E gene which causes production of mRNA consisting of a base sequence represented by SEQ ID NO: 6, or (d) a wild-type eIF(iso)4E gene which causes production of mRNA having a sequence identity of 92% or higher with the base sequence represented by SEQ ID NO: 6 and encodes a functional eIF(iso)4E protein, and (ii) has resistance to viruses belonging to the genus Potyvirus.

Further, one eIF(iso)4E gene may have a plurality of mutations. Still further, mutations in a plurality of eIF(iso)4E genes may be the same mutations or may be different mutations.

Assuming that one of two pairs of eIF(iso)4E genes originally have lost functionality (due to spontaneous mutation), the other one pair still having functionality may have a mutation(s). Further, assuming that although two eIF(iso)4E genes in one of two pairs of eIF(iso)4E genes have completely lost functionality, one eIF(iso)4E gene in the other pair has lost functionality, but the other one eIF(iso)4E gene in the other pair still has functionality, that is, three of the four eIF(iso)4E genes have lost functionality, virus resistance can develop as long as an eIF(iso)4E expression level is sufficiently low. In the case of tobacco wild species (the genus *Nicotiana*) originally having only one pair of eIF(iso)4E genes, a mutation(s) occurs in that one pair of eIF(iso) 4E genes.

In a case where a virus-resistant tobacco in accordance with the present invention has a mutation in a coding region, a mutation occurs in an amino acid sequence of a eIF(iso)4E protein. The mutation is, for example, substitution, deletion, and insertion. In a case where the mutation is substitution of an amino acid, an amino acid to be substituted and a substituted amino acid are not limited to specific ones, provided that an eIF(iso)4E protein is rendered non-functional with respect to a virus. For example, such substitution is preferably non-conservative substitution. The non-conservative substitution is exemplified by substitution of an amino acid by another amino acid having a different charge or a different hydrophobicity (e.g., substitution of a basic amino acid by an acidic amino acid or substitution of a polar amino acid by a non-polar amino acid) and substitution of a certain amino acid by another amino acid having a different size of a side chain. Further, in a case where the mutation occurs in the coding region, the mutation may be a frameshift mutation or a nonsense mutation. In a case where the mutation is a nonsense mutation (a mutation that causes a change to a stop codon), nonsense-mediated mRNA decay (Literature: Brogna and Wen 2009, Nat. Structural Mol. Biol. 16: 107-113) may occur, and degradation of a transcript may thus occur. In view of this, the position of the nonsense mutation is preferably in Exon 1, Exon 2, and/or Exon 3, more preferably in Exon 1 and/or Exon 2. In a case where the mutation is frame-shift mutation or nonsense mutation, it is preferable that the mutation is located between a position about half the length of a gene and a 5' end of the gene. Specifically, it is preferable that the mutation occurs in Exon 1, Exon 2, and/or Exon 3. The closer to the 5' end the mutation is located, the shorter a normal part of a resulting protein is. Thus, the protein is more likely to become non-functional with respect to a virus. In a case where mutations occur in coding regions of all of eIF(iso)4E genes of tobacco (e.g., all the four eIF(iso)4E genes of *N. tabacum*), any eIF(iso)4E protein which is functional with respect to a virus is not produced at all.

In a case where a virus-resistant tobacco in accordance with the present invention has a mutation in a non-coding region, such a mutation does not affect an amino acid sequence that encodes a eIF(iso)4E protein but can alter a secondary structure of DNA or mRNA, alter a binding site for transcription or translational system, or decrease a tRNA binding efficiency. Accordingly, a decrease in transcriptional level and a decrease in translational level can occur.

Meanwhile, in a case where a virus-resistant tobacco in accordance with the present invention has a mutation in a non-coding region at a 5' end, such a mutation can lead to the appearance of ATG (initiation codon) in a frame that is not a correct frame. This may cause a translation to be initiated from such an incorrect frame. In such a case, a normal eIF(iso)4E protein is not produced. For example, in a case where a mutagen is ethyl methane sulfonate (EMS) (described later), a G to A mutation in GTG or a C to T mutation in ACG occurs. This causes another ATG to appear. In a case where a frameshift occurs in such a situation, translation into a normal eIF(iso)4E protein does not occur.

In a case where transcription of an eIF(iso)4E gene is suppressed, the amount of transcripts of the eIF(iso)4E gene is preferably 20% or lower, more preferably 15% or lower, and even more preferably 10% or lower, as compared to a wild type. Further, in a case where translation of an eIF(iso)4E gene is suppressed, the amount of translation products of the eIF(iso)4E gene is preferably 20% or lower, more preferably 15% or lower, and even more preferably 10% or lower, as compared to a wild type.

Further, a mutation in an eIF(iso)4E gene may cause an abnormal splicing of RNA. For example, in a case where a mutation(s) occurs in any of GT bases at a 5' end side of an intron and 10 bases upstream and downstream of the GT bases, preferably in any of GT bases at a 5' end side of an intron and 5 bases upstream and downstream of the GT bases, more preferably in any of GT bases at a 5' end side of an intron and one base upstream and downstream of the GT bases or occurs in any of AG bases at a 3' end side of an intron and 10 bases upstream and downstream of the AG bases, preferably in any of AG bases at a 3' end side of an intron and 5 bases upstream and downstream of the AG bases, more preferably in any of AG bases at a 3' end side of an intron and one base upstream and downstream of the AG bases, intron splicing is unsuccessfully completed, and an abnormal mRNA occurs accordingly. This can produce an eIF(iso)4E protein which is non-functional with respect to a virus or suppress translation of the eIF(iso)4E gene.

A method of inducing a mutation in an eIF(iso)4E gene is not limited to a specific method and can be a known method.

The mutagen can be any chemical agent that induces a mutation in a genomic DNA of tobacco. Examples of such a chemical agent include, but are not limited to, ethyl methane sulfonate (EMS), sodium azide, ethidium bromide, and nitrous acid. Alternatively, the mutagen can be any radiation or the like that induces a mutation in a genomic DNA of tobacco. Examples of such a radiation or the like include, but are not limited to, gamma rays, heavy ion beams, X-rays, neutron beams, and UV. The mutagen is preferably EMS.

Any type of tissues or organs of tobacco can be treated with the mutagen, provided that a plant body can be regenerated from them. Examples of such tissues or organs include, but are not limited to, a seed, a root, a leaf, and a flower. A seed is preferably treated with the mutagen. With respect to mutagenesis population, a dosage of a mutagenic chemical agent or a radiation is empirically determined for each type of plant tissue so as to obtain a mutation frequency lower than a threshold level that leads to lethality or reproductive sterility.

Alternatively, the mutagen may be a transposon (movable genetic element). A transposon can be transferred in a tobacco genome to suppress the function of an eIF(iso)4E gene. A preferred example of such a transposon is exemplified by retrotransposon tnt1 of tobacco. Alternatively, a transposon of other plant can also be used by being introduced into tobacco. Examples of such a transposon include, but are not limited to, transposons Ac/Ds, Spm/dSpm, and Mu of maize, transposon nDart of rice, and transposon tam of snapdragon.

Further alternatively, T-DNA in Ti plasmid of *Agrobacterium* can be inserted into tobacco at random to suppress the function of an eIF (iso) 4E gene. Thus, from a prepared tobacco mutant population (panel) with T-DNA inserted, an individual in which the function of eIF (iso) 4E is suppressed can be screened with use of a base sequence of eIF(iso)4E as an index.

In an example of a method for producing a virus-resistant tobacco having mutations in two pairs of eIF(iso)4E genes (four eIF(iso)4E genes), tobacco is treated with a mutagen, as discussed above, to prepare a population (panel) of tobacco mutants with mutations in the whole tobacco genome, and genomic DNAs are extracted. By using gene-specific primers, eIF(iso)4E genes are amplified from the genomic DNAs of the panel or from those pooled. Subsequently, base sequences of resulting products are determined, and a line having a homozygous mutation is then screened. First, a line having a homozygous mutation in an S-type genome and a line having a homozygous mutation in a T-type genome are obtained and then crossed to obtain $F_1$ individuals. Subsequently, a selfed progeny ($F_2$) is cultivated from the $F_1$ individuals. From the selfed progeny ($F_2$) is obtained a line having homozygous mutations in both an S-type genome and a T-type genome (such a line is obtained at a probability of 1/16 since two elements are recessive). The thus obtained line having eIF(iso)4E gene mutations in both the S-type genome and the T-type genome is subjected to virus assay to verify resistance. In so doing, analysis of expression of eIF(iso)4E genes may be performed by a quantitative PCR or the like to confirm a reduced amount of transcripts.

Thus, an aspect of a method for producing a virus-resistant tobacco may include at least one of the following steps of: preparing a population (panel) of tobacco mutants with mutations in the whole tobacco genome; extracting genomic DNAs; determining base sequences of eIF(iso)4E genes; screening a line having a homozygous mutation; and performing a virus assay to verify resistance.

Further, for the purpose of removing a mutation(s) at a position(s) other than the eIF(iso) 4E genes in DNA, a line having undergone mutation treatment may be crossed at any given timing with a line not having undergone mutation treatment.

Extraction of genomic DNA from a tobacco mutant can be performed by a known method and may be performed by using a commercially available extraction kit. Further, genomic DNA may be a crudely purified one or may be a purified one obtained through several purification steps.

Amplification of a polynucleotide can be performed by, for example, a PCR method, but may be performed by any of other known gene amplification methods including, for example, a ligase chain reaction (LCR) method, a Loop-Mediated Isothermal Amplification (LAMP) method.

A primer sequence for amplifying each polynucleotide can be designed based on, for example, a base sequence represented by SEQ ID NO: 7 or a base sequence represented by SEQ ID NO: 8. First, an S-type specific region and a T-type specific region are determined from a result of analysis of homology between the base sequence represented by SEQ ID NO: 7 (S-type eIF(iso)4E gene) and the base sequence represented by SEQ ID NO: 8 (T-type eIF (iso)4E gene). With primers designed for those regions, the S-type gene and the T-type gene can be independently amplified specifically from a tobacco genome in which an S-type genome and a T-type genome are mixed. A target site at which each of the primers is designed can be selected from the S-type specific region or the T-type specific region, but is preferably an intron, a 5' untranslated region, or a 3' untranslated region. The length of each primer is preferably 15 bases to 30 bases and particularly preferably 17 bases to 25 bases. The primer sequence may be designed based on a sequence of the region specific to the base sequence represented by SEQ ID NO: 7, a sequence of the region specific to the base sequence represented by SEQ ID NO: 8, or a sequence of a region which both of the base sequences have in common. As long as the primer can serve as a primer for amplifying a sequence of a predetermined number of bases including a mutation site, the sequence of the primer may include one or more substitutions, deletions, and/or additions. Further, the primer may be labeled with, for example, a fluorescent substance or a radioactive substance, if necessary.

The length of each polynucleotide to be amplified can be any length that is permitted to be used by various detection methods (described later) and is, for example, 20 bases to 5000 bases, more preferably 50 bases to 2000 bases, even more preferably 100 bases to 700 bases, further more preferably 100 bases to 500 bases.

The followings are non-limiting, typical examples of a method of detecting a mutation(s):

(1) A method of detecting the presence or absence of a mutation(s) by directly reading base sequence of each polynucleotide by means of, for example, a commercially available sequencer; and (2) A method of detecting the presence or absence of a mutation(s) by using a single strand conformation polymorphism (SSCP) method.

By identifying base sequences of (PCR) products which are amplified by primers specific to the eIF(iso)4E genes from a tobacco mutant in which a mutation has been detected by any of the above methods, it is possible to determine whether the mutation is a homozygous mutation or a heterozygous mutation or whether the mutation is a mutation occurring in the S-type genome or a mutation occurring in the T-type genome.

In a case where the EMS treatment is performed, most of mutations that occur in DNA are C to T mutations and G to A mutations. Thus, codons that can turn into stop codons when mutated by the EMS treatment (i.e., potential codons for nonsense mutation) are the following four types of codons: CAA (C appearing in the 1st site is substituted by T), CGA (C appearing in the 1st site is substituted by T), TGG (G appearing in the 2nd or 3rd site is substituted by A), and CAG (C appearing in the 1st site is substituted by T).

For example, in the case of SEQ ID NO: 7, a change to a termination codon (TAA, TAG, or TGA) occurs when there occurs (1) C to T substitution at position 270, (2) G to A substitution at position 295, (3) G to A substitution at position 296, (4) G to A substitution at position 304, (5) G to A substitution at position 305, (6) C to T substitution at position 315, (7) C to T substitution at position 330, (8) G to A substitution at position 343, (9) G to A substitution at position 344, (10) C to T substitution at position 357, (11) G to A substitution at position 394, (12) G to A substitution at position 395, (13) C to T substitution at position 1740, (14) G to A substitution at position 1813, (15) G to A substitution at position 1814, (16) G to A substitution at position 1846, (17) G to A substitution at position 1847, (18) G to A substitution at position 1888, (19) G to A substitution at position 1889, (20) C to T substitution at position 2050, (21) C to T substitution at position 2104, (22) G to A substitution at position 2123, (23) G to A substitution at position 2124, (24) C to T substitution at position 2152, (25) G to A substitution at position 4742, (26) G to A substitution at position 4743, or (27) C to T substitution at position 4926. Thus, a preferred example of a virus-resistant tobacco has one or more of the above mutations (1) to (27) in an eIF(iso)4E gene consisting of a base sequence represented by SEQ ID NO: 7 in genomic DNA. Among these mutations, it is preferable that any of the mutations (1) to (26) occurs, and it is more preferable that any of the mutations (1) to (24) occurs.

For example, in the case of SEQ ID NO: 8, a change to a termination codon (TAA, TAG, or TGA) occurs when there occurs (1) C to T substitution at position 264, (2) G to A substitution at position 289, (3) G to A substitution at position 290, (4) G to A substitution at position 298, (5) G to A substitution at position 299, (6) C to T substitution at position 315, (7) G to A substitution at position 328, (8) G to A substitution at position 329, (9) C to T substitution at position 342, (10) G to A substitution at position 379, (11) G to A substitution at position 380, (12) C to T substitution at position 1630, (13) G to A substitution at position 1703, (14) G to A substitution at position 1704, (15) G to A substitution at position 1736, (16) G to A substitution at position 1737, (17) G to A substitution at position 1778, (18) G to A substitution at position 1779, (19) C to T substitution at position 1940, (20) C to T substitution at position 1994, (21) G to A substitution at position 2013, (22) G to A substitution at position 2014, (23) C to T substitution at position 2042, (24) G to A substitution at position 3224, (25) G to A substitution at position 3225, or (26) C to T substitution at position 3406. Thus, an preferred example of a virus-resistant tobacco has one or more of the above mutations (1) to (26) in an eIF(iso)4E gene consisting of a base sequence represented by SEQ ID NO: 8 in genomic DNA. Among these mutations, it is preferable that any of the mutations (1) to (25) occurs, and it is more preferable that any of the mutations (1) to (23) occurs.

Alternatively, the mutation may be one or more of the following mutations (1) to (4): (1) C of codon CAA is substituted by T; (2) C of codon CGA is substituted by T; (3) C of codon CAG is substituted by T; and (4) G (either one or both of two Gs) of codon TGG is substituted by A, in (a) an exon of a wild-type translation initiation factor eIF(iso)4E gene which encodes a functional translation initiation factor eIF(iso)4E protein having a sequence identity of 92% or higher with an amino acid sequence represented by SEQ ID NO: 3 or SEQ ID NO: 4 or (b) an exon of a wild-type translation initiation factor eIF(iso)4E gene which causes production of mRNA having a sequence identity of 92% or higher with a base sequence represented by SEQ ID NO: 5 or SEQ ID NO: 6 and encodes a functional translation initiation factor eIF(iso)4E protein.

As another means for causing a mutation in the eIF(iso)4E gene, a gene editing technique can be used. The gene editing technique is a technique of introducing a mutation to any region of genome. Examples of such a technique include TALEN (Transcription activator-like effector), CRISPR (Clustered regularly interspaced short palindromic repeat)/CAS, ODM (Oligonucleotide Directed Mutagenesis), and ZFN (Zinc Finger Nuclease).

The definitions of ODM and ZFN are described in Lusser et al. (2012) Nature Biotechnology 30: 231-239. As for ODM, its application to a plant is described in, for example, Zhu et al. (1999) Proc. Natl. Acad. Sci. USA 96: 8768-8773 and Oh and May (2001) Current Opinion in Biotechnology 12:169-172. As for ZFN, its application to a plant is described in Durai et al. (2005) Nucleic Acids Res 33: 5978-5990. In accordance with any of the methods described in these literatures, it is possible to introduce a mutation to the eIF(iso)4E gene.

TALEN will be explained below. A DNA-binding protein derived from a plant pathogen, Transcription activator-like (TAL) effector, has a structural portion in which 34 amino acids are repeated. Such repeating structures recognize bases of a DNA on one-by-one basis. Four types of bases (A, T, G, and C) are present in DNA, and binding specificity of a DNA sequence is determined by two amino acids (13th and 14th amino acids) in the repeating structure of the TAL effector. That is, by selecting the 13th and 14th amino acids in each of the repeating structures, it is possible to artificially bind the TAL effector to a desired region of a DNA. A fusion of the TAL effector with the enzyme FokI, which shows a DNA cleavage activity when it is a dimer, is referred to as TAL effector nuclease (TALEN). When two TALENs are so designed as to bind in close vicinity to each other, FokI forms a dimer to cleave a DNA that is present between the two TALENs. After the cleavage occurs, the DNA is repaired. During the repair, deletion or addition may occur to some extent at a site of the cleavage. TALENs have been found to function in plants (Literature: Zhang et al. (2013) Plant Physiology 161: 20-27).

For example, an eIF(iso)4E-specific nucleotide sequence of preferably 15 bases to 25 bases, more preferably 18 bases to 22 bases, is designed in SEQ ID NO: 1 or SEQ ID NO: 2, preferably in a protein coding region. Then, another nucleotide sequence is designed similarly in a place preferably 9 bases to 15 bases away from the previously designed nucleotide sequence. A portion flanked by these two nucleotides is supposed to be cut out later.

In order to determine whether the nucleotide sequences thus designed are specific to the eIF(iso)4E gene, not only a sequence itself but also the presence or absence of a region having a high homology including that sequence may be determined by performing, for example, homology search of the designed nucleotide sequence through a known sequence database of tobacco (*Nicotiana tabacum*), alternatively *Nicotiana sylvestris* or *Nicotiana tomentosiformis*. Examples of the sequence database as used include GenBank, EMBL (The European Molecular Biology Loboratory), and DDBJ (DNA Data Bank of Japan). As a sequence analysis algorithm, for example, BLAST can be used. Examples of types of databased sequences include, but are not limited to, Nucleotide Collection (nr/nt), Expressed Sequence Tags (EST), Genomic survey sequences (GSS), and Whole genome shotgun contigs (WGS).

Based on the designed specific nucleotide sequence, a gene sequence of a TALE is designed. For example, GoldenGateTALEN Kit (Addgene), which is a non-limiting example, can be used to bind a plurality of repeating structures. In fusing the TALE and the FokI, for example, a suitable linker sequence may be arranged. Note that sequence of the FokI is included on a known database. A promotor for expressing a TALE/FokI fusion gene in tobacco is preferably a promotor that achieves high-level expression. Examples of such a promotor include, but are not limited to, constitutive expression promotors such as a promotor of a cauliflower mosaic virus 35S RNA gene, a promotor of an actin gene, and a promotor of a ubiquitin gene; green tissue specific promotors such as a promotor of a Rubisco small subunit gene and a promotor of a PPDK gene; and organ specific promotors and stage specific promotors. In order to increase an expression level, a desired intron may be arranged between the promotor and TALE/

FokI. In order to further increase an expression level, codons of TALE/FokI may be optimized to be plant (tobacco) codons. The plant codons are listed in, for example, a known database such as Codon Usage Database (zwww.kazusa.orjp/codon/).

A vector for introducing a TALEN expression cassette to a plant may have incorporated thereinto not only the aforementioned cassette, but also an expression cassette of a drug resistance gene (selection marker) for selecting a plant cell to which the TALEN expression cassette is introduced. The drug resistance gene is any drug resistance gene for a drug capable of selecting tobacco cells, and examples thereof include, but are not limited to, a kanamycin resistance gene (neomycin phosphotransferase: NPT-II) and a hygromycin resistance gene (hygromycin phosphotransferase: HPT). Further, the promoter is not limited to a specific one, provided that it enables constitutive expression.

Furthermore, in a case where *Agrobacterium* is used to stably introduce the TALEN expression cassette to a plant, the TALEN expression cassette and the selection marker expression cassette need to be present in T-DNA. In this case, a right border (RB) sequence and a left border (LB) sequence, as boundary sequences of the T-DNA, are arranged at both ends of the T-DNA.

Examples of a vector for introducing the TALEN expression cassette to a plant, the vector enabling a gene to be introduced into tobacco include, but are not limited to, a pBI vector and a pSB vector (Literature: Komari et al. 2006 Methods in Mol. Biol. 343: 15-41.), a pLC vector (Literature: Specification of U.S. Pat. No. 8,298,819), and a pGreen vector (Literature: Hellens et al. 2000 Plant Mol. Biol. 42: 819-832.).

A method of introducing the TALEN expression cassette to a plant is not limited to a specific method, and can be a method commonly employed by those skilled in the art, such as the aforementioned method using *Agrobacterium*, a method using a particle gun, a PEG method, an electroporation method, and an agroinfiltration method. A tissue or organ of tobacco to undergo the introduction is not limited to a specific type of tissue or organ, provided that regeneration of a plant body is achieved. Examples of such a tissue or organ include a seed, a root, a leaf, and a flower.

Selection and cultivation of a transformed plant can be easily performed by those skilled in the art. Examples of a drug used for the selection include, but are not limited to, kanamycin and hygromycin. The concentration of the drug is, for example, 20 mg/mL to 200 mg/mL, preferably 50 mg/mL to 100 mg/mL. A medium for the cultivation of a plant culture may be a medium commonly used. Examples of a type of inorganic salt include MS and LS. To the inorganic salt, for example, sucrose, agar, or plant hormone is added. A concentration of such a substance can be determined in accordance with a protocol commonly used by those skilled in the art.

As a tissue or organ to undergo gene introduction, not only the tissue or organ listed above, but also a protoplast can be used. The protoplast can be prepared by a usual method using a cell wall degrading enzyme. Further, as a gene introduction method, not only the aforementioned stable transformation method, but also a transient method can be employed. Transient assay can be carried out using an electroporation method, a PEG method, or other usual method. Another transient assay method is exemplified by, for example, Agro-infiltration and a viral vector. Examples of the viral vector include, but are not limited to, ALSV (Apple latent spherical virus) and TRV (Tobacco rattle virus).

Whether the eIF(iso)4E gene is mutated in an individual, or in a tissue or organ, which has been regenerated from a transgenic cell can be confirmed by designing primers that flank a target region, extracting DNA from a desired plant tissue, amplifying that region by PCR or the like method, and then examining a base sequence of a PCR product.

A method of analyzing gene expression is not limited to a specific one, and can be any of known methods including, for example, a northern hybridization method and a quantitative PCR method. A probe used in hybridization can be designed to have a base sequence represented by SEQ ID NO: 1 or a part of that base sequence (e.g., SEQ ID NO: 9), to have a base sequence represented by SEQ ID NO: 2 or a part of that base sequence, or to have a base sequence in which one or more bases are substituted, deleted, or inserted in any of these base sequences. The length of the probe can be, for example, 20 bases to a full length of the sequence.

Extraction of RNA for use in the expression analysis is performed by a known method including, for example, a method using guanidine hydrochloride and an SDS-phenol method, and may be performed using a commercially available kit. Total RNA may be purified to obtain mRNA (polyA+RNA).

Synthesis of cDNA for use in performing the quantitative PCR can be performed by a known method using reverse transcriptase and either an oligo dT primer or a gene-specific primer, and can be performed by means of a commercially available kit.

Further, a primer for quantitative PCR can be designed based on SEQ ID NO: 1 or SEQ ID NO: 2. The length of the primer is preferably 15 bases to 30 bases, particularly preferably 17 bases to 25 bases. The length of a target sequence to be amplified by a set of primers is not limited to a specific length, and can be, for example, 40 bases to a full length of the sequence, preferably 50 bases to 500 bases.

In performing quantitative PCR using a fluorescent PCR apparatus, not only sequences of the primers, but also a sequence of a probe are set in a target sequence. The length of the target sequence is preferably 40 bases to 200 bases, more preferably 50 bases to 150 bases. A reporter dye for labeling the primers and the probe is exemplified by FAM, HEX, TET, and Cyanine5, and a quencher dye is exemplified by, for example, TAMRA and BHQ1. The reporter dye and the quencher dye are not limited to these dyes, and can be selected and combined as appropriate by those skilled in the art. A gene used as an internal standard for quantitative PCR can be any constitutive expression gene. A preferable internal standard gene is exemplified by, for example, an elongation factor gene and an actin gene.

CRISPR/CAS will be explained below. CRISPR/CAS system, which is a gene editing technique using (i) a guide RNA that recognizes a DNA sequence and (ii) CAS nuclease, is known to function in a plant (Literature: Belhaj et al. (2013) Plant Methods 9:39). This technique, which is a technique for cutting a DNA having a desired sequence on genome, relies, regarding deletion, addition, and insertion in a target genomic sequence, on mistakes made by a DNA repair system of a host, as is the case with TALEN.

A promotor for expressing CAS9 in a plant is preferably a promotor that achieves high-level expression. Examples of such a promotor include, but are not limited to, a promotor of a 35S RNA gene, a promotor of a ubiquitin gene, and a promotor of a PPDK gene, which are listed earlier. In order to increase an expression level, a desired intron may be arranged between the promotor and CAS9. Note that the base sequence of CAS9 is known. In order to further increase an expression level, codons of CAS9 may be optimized to be plant (tobacco) codons. Further, a nuclear localization signal (NLS) may be added to CAS9.

A desired genomic sequence and a complementary guide RNA are designed. For example, an eIF(iso)4E-specific nucleotide sequence of preferably 19 bases to 22 bases is determined in SEQ ID NO: 1 or SEQ ID NO: 2, preferably in a protein coding region. In this case, at a 3' end side of that sequence, a NGG sequence called protospacer-adjacent motif (PAM) needs to be present. Further, in a case where the type of the promoter described later is U6, a transcription initiation point (5' end of a guide RNA) needs to be G. In a case where the type of the promoter is U3, the transcription initiation point needs to be A.

In order to determine whether the sequence of the guide RNA is specific to the eIF(iso)4E gene, not only a sequence itself but also the presence or absence of a region having a high homology including that sequence can be determined by performing, for example, homology search of the designed sequence through the sequence database of tobacco (*Nicotiana tabacum*), alternatively *Nicotiana sylvestris* or *Nicotiana tomentosiformis*. The sequence database and sequence analysis algorithm are similar to those discussed earlier.

After the guide RNA is designed, a sgRNA scaffold sequence is fused to a 3' end of the guide RNA to obtain a sgRNA (guide (g)RNA+gRNA scaffold), and a construct for expressing the sgRNA is then produced. At that time, a promoter including, for example, U6 and U3 of RNA polymerase III can be used as a promotor. The construct completed with use of a suitable vector is introduced into tobacco, a recombinant is selected, and regeneration is then performed. In order to further ensure the occurrence of a mutation, a plurality of guide RNAs can be designed within eIF(iso)4E, and constructs for expressing the respective guide RNAs can be introduced into tobacco simultaneously. In this case, a plurality of guide RNA expression cassettes and a CAS9 expression cassette may be arranged on one T-DNA simultaneously.

Note that a vector for introducing, to a plant, a cassette that enables expression of a guide RNA and CAS9 and a method of tobacco transformation are similar to those explained earlier for TALEN.

As a tissue or organ to undergo gene introduction, not only the tissue or organ listed above, but also a protoplast can be used. The protoplast can be prepared by a usual method using a cell wall degrading enzyme. Further, as a gene introduction method, not only the aforementioned stable transformation method, but also a transient method can be employed. Transient assay is similar to that explained earlier for TALEN.

Whether the eIF(iso)4E gene is mutated in an individual, or in a tissue or organ, which has been regenerated from a transgenic cell can be confirmed by a method similar to that explained earlier for TALEN.

Examples of a virus assay method include, but are not limited to, a mechanical inoculation method using a combination of a virus solution and solid powder such as carborundum and an inoculation method using an aphid infected with a virus. The virus as used is not limited to a specific virus, and may be any of the viruses listed above as the virus to which a virus-resistant tobacco shows resistance.

(Aspect 2 of Virus-Resistant Tobacco and Method for Producing the Virus-Resistant Tobacco)

Another aspect of a virus-resistant tobacco in accordance with the present invention is a virus-resistant tobacco in which an expression level of an eIF(iso)4E gene is 20% or lower, as compared to a wild type. An expression level of an eIF(iso)4E gene in tobacco in which eIF(iso)4E expression is suppressed is preferably 15% or lower and more preferably 10% or lower, in a case where the expression level in the wild type is 100%. Here, the "wild type" refers to tobacco in which a factor that suppresses expression of an eIF(iso)4E gene has not been introduced and in which the eIF(iso)4E gene is not mutated.

For the production of such a virus-resistant tobacco, any of known methods in the art can be employed, including, for example, a method using antisense, a method using cosuppression, a method using RNA interference (RNAi), a method using microRNA, a method using VIGS, a method using ribozymes, a method using homologous recombination, and a method using expression of dominant negative gene products. Specifically, it is possible to produce the virus-resistant tobacco by introducing a factor that suppresses the expression level of the eIF(iso)4E gene to 20% or lower, preferably 15% or lower, more preferably 10% or lower as compared to the wild type.

A method of suppressing eIF(iso)4E expression is preferably RNAi. Specifically, RNAi construct is prepared by using, as a trigger, a base sequence of the eIF(iso)4E gene (e.g., SEQ ID NO: 1) or a part of that base sequence (e.g., SEQ ID NO: 9) or a base sequence represented by, for example, SEQ ID NO: 2 or a part of that base sequence. The RNAi construct thus prepared is fused with a promotor that causes expression in a plant, and a fusion thus obtained is introduced into tobacco by using a vector. Thus, a virus-resistant tobacco is obtained in which the RNAi construct is expressed to suppress expression of the eIF(iso)4E gene. Therefore, a virus-resistant tobacco according to an aspect can retain RNAi construct for suppressing expression of the eIF(iso)4E gene.

The length of the trigger can be, for example, 21 bases to a full length of the sequence, preferably 50 bases or more, more preferably 100 bases or more. A trigger sequence may be such that one or more bases are substituted, deleted, or inserted.

In RNAi, an RNAi construct is prepared such that a portion of the trigger sequence extending in a sense direction and the other portion of the trigger sequence extending in an antisense direction are functionally linked so that the trigger sequence is an inverted repeat sequence. In preparation of the RNAi construct, a spacer sequence is preferably provided between both of the triggers. Such a spacer sequence is preferably a sequence that is not contained in a tobacco genome or a region, such as an intron sequence, that is not contained in mature mRNA. Examples of such a sequence include, but are not limited to, intron sequences of β-glucuronidase (GUS) gene, pyruvate dehydrogenase kinase (pdk) gene, and catalase (cat) gene.

Examples of a promotor for causing transcription of the RNAi construct in a plant include, but are not limited to, constitutive expression promotors such as a promoter of a cauliflower mosaic virus 35S RNA gene, a promoter of an actin gene, and a promoter of a ubiquitin gene; green tissue specific promotors such as a promoter of a Rubisco small subunit gene and a promoter of a PPDK gene; and organ specific promotors and stage specific promotors. The promotor is preferably a promoter that causes expression in a tissue infected with a virus.

A terminator can be any terminator that functions in a plant. Examples of the terminator include, but are not limited to, a terminator of a cauliflower mosaic virus 35S RNA gene, a terminator of a cauliflower mosaic virus 19S RNA gene, and a terminator of a nopaline synthetase gene.

A vector for introducing an RNAi expression cassette to a plant may have incorporated thereinto not only the aforementioned cassette, but also an expression cassette of a drug resistance gene for selecting a plant cell to which the RNAi expression cassette is introduced. The drug resistance gene is any drug resistance gene for a drug capable of selecting tobacco cells, and examples thereof include, but are not limited to, a kanamycin resistance gene (neomycin phosphotransferase: NPT-II) and a hygromycin resistance gene (hygromycin phosphotransferase: HPT). Further, the promoter is not limited to a specific one, provided that it enables constitutive expression.

Furthermore, in a case where *Agrobacterium* is used to stably introduce the RNAi expression cassette to a plant, the RNAi expression cassette and the selection marker expression cassette need to be present in T-DNA. In this case, a right border (RB) sequence and a left border (LB) sequence, as boundary sequences of the T-DNA, are arranged respectively at both ends of the T-DNA.

Further, in order to visually predict gene expression, an expression cassette of a fluorescent protein may be arranged in the T-DNA. Examples of the fluorescent protein include, but are not limited to, green fluorescent protein (GFP) and yellow fluorescent protein (YFP). The fluorescent protein is preferably GFP. Fluorescence can be observed by an image analyzer.

Examples of a vector for introducing the RNAi expression cassette to a plant, the vector enabling a gene to be introduced into tobacco include, but are not limited to, pBI vectors and pSB vectors (Literature: Komari et al. 2006 Methods in Mol. Biol. 343: 15-41.), pLC vectors (Literature: Specification of U.S. Pat. No. 8,298,819), a pGreen vector (Literature: Hellens et al. 2000 Plant Mol. Biol. 42: 819-832.), a pHellsgate vector (Literature: Wesley et al. 2001 Plant J 27: 581-590.), and a pSP231 vector (Literature: International publication No. WO 2011/102394).

A method of introducing the RNAi expression cassette to a plant is not limited to a specific method, and can be a method commonly employed by those skilled in the art, such as the aforementioned method using *Agrobacterium*, a method using a particle gun, a PEG method, an electroporation method, and an agroinfiltration method. A tissue or organ of tobacco to undergo the introduction is not limited to a specific type of tissue or organ, provided that regeneration of a plant body is achieved. Examples of such a tissue or organ include a seed, a root, a leaf, and a flower.

Selection and cultivation of a transformed plant can be easily performed by those skilled in the art. Examples of a drug used for the selection include, but are not limited to, kanamycin and hygromycin. The concentration of the drug is, for example, 20 mg/mL to 200 mg/mL, preferably 50 mg/mL to 100 mg/mL. A medium for the cultivation of a plant culture may be a medium commonly used. Examples of a type of inorganic salt include MS and LS. To the inorganic salt, for example, sucrose, agar, or plant hormone is added. A concentration of such a substance can be determined in accordance with a protocol commonly used by those skilled in the art.

A method of analyzing gene expression and a virus assay method are as discussed earlier.

[2. Method of Imparting Virus Resistance to Tobacco]

The present invention also provides a method of imparting virus resistance to tobacco.

An aspect of the method imparts virus resistance to tobacco by introducing a mutation to a translation initiation factor eIF(iso)4E gene, the mutation causing production of a translation initiation factor eIF(iso)4E protein which is non-functional to a virus or suppressing expression of the translation initiation factor eIF(iso)4E gene. A method of introducing such a mutation is as discussed in [1. Virus-resistant tobacco and method for producing the virus-resistant tobacco].

Another aspect of the method imparts virus resistance to tobacco by introducing a factor that suppresses an expression level of a translation initiation factor eIF(iso)4E gene to 20% or lower, preferably 15% or lower, more preferably 10% or lower, as compared to the wild type. A method of introducing such a factor is as discussed in [1. Virus-resistant tobacco and method for producing the virus-resistant tobacco].

[3. DNA Marker and Use Thereof]

According to the present invention, a DNA marker can be developed by using the mutation that occur on an eIF (iso)4E gene of tobacco, and the DNA marker can be utilized for marker breeding. The "DNA marker" refers to a difference in DNA base sequence (mutation or polymorphism) between varieties or individuals or a tool for detecting the difference, and also refers to a difference in DNA base sequence (mutation or polymorphism) which serves as a marker for identifying varieties or individuals from each other or a tool for detecting the difference. In a case where a mutation in an eIF(iso)4E gene is determined, and it is confirmed that the mutation renders tobacco resistant to a virus, a tobacco mutant with that mutation can be used as a breeding mother plant having that virus resistance. Further, since the mutation responsible for the resistance has been already found, it is possible to design, on an eIF(iso)4E gene, a marker which can be used for identification of the mutation responsible for the resistance. Since a relation between that mutation and the virus resistance will never be broken by genetic segregation, it is possible to perform a precise marker breeding. Detection of the presence or absence of this mutation eliminates a need to confirm virus resistance after each iteration of crossbreeding or the like breeding.

Extraction of genomic DNA from tobacco can be performed by a usual method, and may be performed by using a commercially available extraction kit, which is a non-limiting example. Further, genomic DNA may be a crudely purified one or may be a purified one obtained through several purification steps. The presence or absence of a mutation can be detected by any technique that enables detection of the presence or absence of a mutation. Examples of such a technique include RFLP, a technique to which nucleic acid (also referred to as a "polynucleotide") hybridization using a single-stranded DNA as a probe is applied, and a technique, like PCR etc., involving amplification of a polynucleotide.

Amplification of a polynucleotide can be performed by, for example, a PCR method, but may be performed by any of other known gene amplification methods including, for example, a LCR method, a Strand Displacement Amplification (SDA) method, and a LAMP method. The length of each polynucleotide to be amplified can be any length that is permitted to be used by various detection methods (described later) and is, for example, preferably 40 bases to 5000 bases, more preferably 100 bases to 1000 bases, even more preferably 100 bases to 700 bases, further more preferably 100 bases to 500 bases.

A primer sequence for amplifying each polynucleotide is preferably designed so as to flank or contain a mutation site. However, the position at which the primer sequence is designed is not limited to a specific position. The length of each primer is preferably 15 bases to 30 bases and particularly preferably 17 bases to 25 bases. As long as the primer can serve as a primer for amplifying a sequence of a predetermined number of bases including a mutation site, the sequence of the primer may include one or more substitutions, deletions, and/or additions. Further, the primer may be labeled with, for example, a fluorescent substance or a radioactive substance, if necessary.

The mutation to be detected is a mutation that causes production of an eIF(iso)4E protein which is non-functional with respect to a virus or a mutation that suppresses expression of an eIF (iso) 4E gene. Specific examples of the mutation are as discussed in [1. Virus-resistant tobacco and method for producing the virus-resistant tobacco].

The followings are non-limiting, typical examples of a method of detecting a mutation(s):

(1) A method of detecting the presence or absence of a mutation(s) by directly reading base sequence of an amplified polynucleotide by means of, for example, a commercially available sequencer;

(2) A method of detecting the presence or absence of a mutation(s) by using a single strand conformation polymorphism (SSCP) method; and (3) A method of processing an amplified polynucleotide with a restriction enzyme that specifically recognizes a sequence of a mutation site (a sequence before or after a mutation occurs), and then determining the presence or absence of cleavage (Cleaved Amplified Polymorphic Sequence (CAPS) method). As other method, a derived CAPS (dCAPS) method may be employed of using a primer set containing an intentionally designed mismatch primer to produce a restriction enzyme recognition site. Examples of such a primer set include, but are not limited to, a set of the following nucleic acids: as primers for detecting C to T mutation at 330th base of the base sequence of an S-type eIF(iso)4E gene represented by SEQ ID NO: 7, a nucleic acid consisting of a base sequence represented by SEQ ID NO: 45; and a nucleic acid consisting of a base sequence represented by SEQ ID NO: 46. The use of a mismatch primer, like the base sequence represented by SEQ ID NO: 46, can worsen an amplification efficiency. In that case, the mutation may be detected in the following manner. That is, PCR is performed once with primers containing no mismatch (in the above case, for example, a set of nucleic-acid primers consisting of base sequences represented by SEQ ID NO: 25 and SEQ ID NO: 26, respectively) designed at sites outside the target sequence. Subsequently, another PCR is performed for re-amplification, using a mismatch primer and a part of PCR products, which serve as a template, and PCR products thus obtained are then processed with a restriction enzyme.

Examples of the primer set containing a mismatch primer include, but are not limited to, a set of the following nucleic acids: as primers for detecting G to A mutation at 299th base of the base sequence of a T-type eIF(iso)4E gene represented by SEQ ID NO: 8, a nucleic acid consisting of a base sequence represented by SEQ ID NO: 47; and a nucleic acid consisting of a base sequence represented by SEQ ID NO: 48. The use of a mismatch primer, like the base sequence represented by SEQ ID NO: 48, can worsen an amplification efficiency. In that case, the mutation may be detected in the following manner. That is, PCR is performed once with primers containing no mismatch (in the above case, for example, a set of nucleic-acid primers consisting of base sequences represented by SEQ ID NO: 31 and SEQ ID NO: 32, respectively) designed at sites outside the target sequence. Subsequently, another PCR is performed for re-amplification, using a mismatch primer and a part of PCR products, which serve as a template, and PCR products thus obtained are then processed with a restriction enzyme.

Note that, in a case where a mutation other than the mutations exemplified above is detected, those skilled in the art can design a primer sequence, perform PCR, and detect an intended mutation, without requiring much effort. For example, the primer sequence can be designed via a web (Literature: Neff et al. (2002) Web-based primer design for single nucleotide polymorphism analysis. TRENDS in Genetics 18: 613-615).

Note that in a case where a DNA polymerase having proofreading activity is used to perform PCR with primers containing a mismatch near a 3' end of one of the primers, the mismatch is corrected, and a failure to cause cleavage with the restriction enzyme may occur. Accordingly, in a case where a mismatch primer is used in the dCAPS method, DNA polymerase having no proofreading activity is preferably used. Such DNA polymerase is exemplified by, but not limited to, TaKaRa Taq™ (Takara-Bio Inc.). Further, in a case where a cleavage site for the restriction enzyme is provided near the 3' end of the primer, the presence or absence of cleavage is detected as a difference in primer length.

(4) A method of confirming the presence or absence of a mutation by performing hybridization with a probe designed to hybridize specifically with a mutation site.

An analysis process is not limited to a specific one. For example, PCR performed by a TaqMan (registered trademark) probe method, MassARRAY (registered trademark) analysis which is a measurement technique using TOF-MS, or the like method can be used.

(5) A method of detecting the presence or absence of a mutation from the presence or absence of amplification by performing amplification by, for example, a PCR method with use of a primer sequence designed to contain a part of a sequence of a mutation site (sequence before and/or after a mutation occurs) (allele-specific PCR method).

Examples of primers used in such a method include, but are not limited to, a set of the following nucleic acids: as primers for detecting C to T mutation at 330th base of the base sequence of an S-type eIF(iso)4E gene represented by SEQ ID NO: 7, a nucleic acid consisting of a base sequence represented by SEQ ID NO: 37; and a nucleic acid consisting of a base sequence represented by SEQ ID NO: 39. In this case, for example, a nucleic-acid primer being specific to the base sequence before the mutation occurs and consisting of a base sequence represented by SEQ ID NO: 38 can be used as a control.

Further, examples of primers for detecting G to A mutation at 299th base of the base sequence of a T-type eIF(iso)4E gene represented by SEQ ID NO: 8 include, but are not limited to, a set of the following nucleic acids: a nucleic acid consisting of a base sequence represented by SEQ ID NO: 40; and a nucleic acid consisting of a base sequence represented by SEQ ID NO: 42. In this case, for example, a nucleic-acid primer being specific to the base sequence before the mutation occurs and consisting of a base sequence represented by SEQ ID NO: 41 can be used as a control.

In a case where a base corresponding to a target mutation is to be provided near a 3' end of a primer, that base is preferably provided at the end of the primer or at any of positions corresponding to several bases near the end of the primer. Further, in a case where a target mutation is provided near the 3' end of the primer, not only a sequence of a mutant type but also a sequence of a wild type having no mutation may be amplified. In such a case, a mismatch other than a target mismatch may be introduced to a primer for mutant-type detection and to a primer for wild-type detection at the same positions (bases represented by smaller letters in SEQ ID NO: 38, SEQ ID NO: 39, SEQ ID NO: 41, and SEQ ID NO: 42), so that PCR is performed to obtain mutant type-specific or wild type-specific amplification.

In addition to primers for a target gene, primers for a gene that serves as an internal standard of PCR (for example, primers consisting of base sequences represented by SEQ ID NO: 43 and SEQ ID NO: 44) may be added to a PCR reaction solution, if necessary.

Note that, in a case where a mutation other than the mutations exemplified above is detected, those skilled in the art can design a primer sequence, perform PCR, and detect an intended mutation, without requiring much effort.

Note that a gene mutation detection technique is detailed in the following literature: the website of the Japan Patent Office: www.jpo.go.jp/shiryou/s_sonota/hyoujun_gijutsu/kakusan/0025.html. Further, gene mutation detection and analysis methods are detailed in the following literature: the website of the Japan Patent Office: www.jpo.go.jp/shiryou/s_sonota/hyoujun_gijutsu/kakusan/0028.html. Alternatively, reference may be made to the following literature: Agarwal et al. (2008): Advances in molecular marker techniques and their applications in plant sciences. Plant Cell Rep. 27:617-631.; and Neff et al. (1998): dCAPS, a simple technique for the genetic analysis of single nucleotide polymorphisms: experimental applications in *Arabidopsis thaliana* genetics. Plant J. 14: 387-392.

Thus, the present invention provides a polynucleotide for detecting a mutation in an eIF(iso)4E gene. The mutation is a mutation that causes production of an eIF(iso)4E protein which is non-functional with respect to a virus or a mutation that suppresses expression of the eIF(iso)4E gene. Specific examples of the mutation are as discussed in [1. Virus-resistant tobacco and method for producing the virus-resistant tobacco].

Further, an aspect of the detection-use polynucleotide is a nucleic-acid primer or a set of nucleic-acid primers. The set of nucleic-acid primers may be a set of nucleic-acid primers flanking the mutation or a set of nucleic-acid primers which contains a polynucleotide consisting of a continuous base sequence which contains the mutation or a sequence complementary to the continuous base sequence. Another aspect of the detection-use polynucleotide is a nucleic-acid probe that hybridizes with a continuous base sequence which contains the mutation or a sequence complementary to the continuous base sequence.

The present invention also provides a method for evaluating tobacco for resistance to a virus, the method using, as an index of virus resistance, occurrence of the mutation in an eIF(iso)4E gene in genomic DNA of tobacco.

The present invention also provides a kit for evaluating tobacco for resistance to a virus, the kit including a set of nucleic-acid primers for detecting the mutation in an eIF(iso)4E gene.

The present invention also provides a kit for evaluating tobacco for resistance to a virus, the kit including a probe that hybridizes with a continuous base sequence which contains the mutation in an eIF(iso)4E gene or a sequence complementary to the continuous base sequence.

The present invention also provides a method for breeding a virus-resistant tobacco, the method including a selection step of selecting tobacco having resistance to a virus by using the above evaluation method.

The present invention also provides a method of selecting a virus-resistant tobacco, the method including: an examination step of examining tobacco for presence or absence of the mutation in genomic DNA by using the aforementioned detection-use polynucleotide; and a selection step of selecting, as a virus-resistant tobacco, tobacco in which the mutation has been detected in the examination step. Details of the examination method using a detection-use polynucleotide are as discussed earlier.

The present invention also provides a DNA marker for evaluating tobacco for resistance to a virus, the DNA marker including a polynucleotide consisting of a continuous base sequence which contains the mutation in an eIF(iso)4E gene or a sequence complementary to the continuous base sequence.

[4. Leaf Tobacco and Tobacco Product]

Leaf tobacco produced through cultivation of a virus-resistant tobacco of the present invention does not suffer from a disease caused by the virus (for example, the PVY strain that breaks virus resistance of Virgin A mutant or TBTV). Therefore, such leaf tobacco is less deteriorated and is of a high quality, as compared to leaf tobacco produced from a virus non-resistant tobacco which has been cultivated particularly in an environment where the disease can break out. As a result, it is possible to produce a tobacco product of higher quality.

The "leaf tobacco", which is obtained by drying harvested fresh leaves of a tobacco plant, refers to an ingredient for production of a tobacco product. The "tobacco product" refers to, for example, cigarette (with a filter and without a filter), cigar, cigarillos, snus, snuff, chewing tobacco, and electronic tobacco.

Accordingly, the present invention provides leaf tobacco which is produced from the virus-resistant tobacco.

The present invention also provides a tobacco product containing the leaf tobacco as an ingredient.

[5. Recapitulation]

As described above, the inventors of the present invention diligently studied to solve the foregoing problems and found for the first time that tobacco in which the functioning of eIF(iso)4E is suppressed has resistance to the PVY-breaking strain and TBTV. The inventors also elucidated that one of two pairs of eIF(iso)4E genes present in a tobacco genome is involved in resistance to the PVY-breaking strain while the other pair is involved in resistance to TBTV, and found that suppression of the function of each pair of eIF(iso)4E genes can impart resistance to the corresponding virus. Further, the inventors verified that growth inhibition never occurs in the tobacco in which the function of eIF(iso)4E is suppressed, and accomplished the present invention.

An aspect of a virus-resistant tobacco in accordance with the present invention is such that the virus-resistant tobacco includes a mutation in a translation initiation factor eIF(iso)4E gene, the mutation causing production of a translation initiation factor eIF(iso)4E protein which is non-functional with respect to a virus or suppressing expression of the translation initiation factor eIF(iso)4E gene.

The aspect of the virus-resistant tobacco in accordance with the present invention is preferably such that the mutation is a nonsense mutation.

The aspect of the virus-resistant tobacco in accordance with the present invention may be such that the mutation is one or more of the following mutations (1) to (4): (1) C of codon CAA is substituted by T; (2) C of codon CGA is substituted by T; (3) C of codon CAG is substituted by T; and (4) G (either one or both of two Gs) of codon TGG is substituted by A, in (a) an exon of a wild-type translation initiation factor eIF(iso)4E gene which encodes a translation initiation factor eIF(iso)4E protein consisting of an amino acid sequence represented by SEQ ID NO: 3 or SEQ ID NO:

4, (b) an exon of a wild-type translation initiation factor eIF(iso)4E gene which encodes a functional translation initiation factor eIF(iso)4E protein having a sequence identity of 92% or higher with the amino acid sequence represented by SEQ ID NO: 3 or SEQ ID NO: 4, (c) an exon of a wild-type translation initiation factor eIF(iso)4E gene which causes production of mRNA consisting of a base sequence represented by SEQ ID NO: 5 or SEQ ID NO: 6, or (d) an exon of a wild-type translation initiation factor eIF(iso)4E gene which causes production of mRNA having a sequence identity of 92% or higher with the base sequence represented by SEQ ID NO: 5 or SEQ ID NO: 6 and encodes a functional translation initiation factor eIF(iso)4E protein.

The aspect of the virus-resistant tobacco in accordance with the present invention may be such that the mutation is one or more of the following mutations (1) to (27): (1) C to T substitution at position 270, (2) G to A substitution at position 295, (3) G to A substitution at position 296, (4) G to A substitution at position 304, (5) G to A substitution at position 305, (6) C to T substitution at position 315, (7) C to T substitution at position 330, (8) G to A substitution at position 343, (9) G to A substitution at position 344, (10) C to T substitution at position 357, (11) G to A substitution at position 394, (12) G to A substitution at position 395, (13) C to T substitution at position 1740, (14) G to A substitution at position 1813, (15) G to A substitution at position 1814, (16) G to A substitution at position 1846, (17) G to A substitution at position 1847, (18) G to A substitution at position 1888, (19) G to A substitution at position 1889, (20) C to T substitution at position 2050, (21) C to T substitution at position 2104, (22) G to A substitution at position 2123, (23) G to A substitution at position 2124, (24) C to T substitution at position 2152, (25) G to A substitution at position 4742, (26) G to A substitution at position 4743, and (27) C to T substitution at position 4926, in a translation initiation factor eIF(iso)4E gene consisting of a base sequence represented by SEQ ID NO: 7 in genomic DNA.

The aspect of the virus-resistant tobacco in accordance with the present invention may be such that the mutation is one or more of the following mutations (1) to (26): (1) C to T substitution at position 264, (2) G to A substitution at position 289, (3) G to A substitution at position 290, (4) G to A substitution at position 298, (5) G to A substitution at position 299, (6) C to T substitution at position 315, (7) G to A substitution at position 328, (8) G to A substitution at position 329, (9) C to T substitution at position 342, (10) G to A substitution at position 379, (11) G to A substitution at position 380, (12) C to T substitution at position 1630, (13) G to A substitution at position 1703, (14) G to A substitution at position 1704, (15) G to A substitution at position 1736, (16) G to A substitution at position 1737, (17) G to A substitution at position 1778, (18) G to A substitution at position 1779, (19) C to T substitution at position 1940, (20) C to T substitution at position 1994, (21) G to A substitution at position 2013, (22) G to A substitution at position 2014, (23) C to T substitution at position 2042, (24) G to A substitution at position 3224, (25) G to A substitution at position 3225, and (26) C to T substitution at position 3406, in a translation initiation factor eIF(iso)4E gene consisting of a base sequence represented by SEQ ID NO: 8 in genomic DNA.

The aspect of the virus-resistant tobacco in accordance with the present invention may be such that the mutation is one or more mutations in (a) a wild-type translation initiation factor eIF(iso)4E gene which encodes a translation initiation factor eIF(iso)4E protein consisting of an amino acid sequence represented by SEQ ID NO: 3, (b) a wild-type translation initiation factor eIF(iso)4E gene which encodes a functional translation initiation factor eIF(iso)4E protein having a sequence identity of 92% or higher with the amino acid sequence represented by SEQ ID NO: 3, (c) a wild-type translation initiation factor eIF(iso)4E gene which causes production of mRNA consisting of a base sequence represented by SEQ ID NO: 5, or (d) a wild-type translation initiation factor eIF(iso)4E gene which causes production of mRNA having a sequence identity of 92% or higher with the base sequence represented by SEQ ID NO: 5 and encodes a functional translation initiation factor eIF(iso)4E protein, and the virus is a virus belonging to the genus Umbravirus.

The aspect of the virus-resistant tobacco in accordance with the present invention is preferably such that the virus belonging to the genus Umbravirus is Tobacco bushy top virus.

The aspect of the virus-resistant tobacco in accordance with the present invention may be such that the mutation is one or more mutations in (a) a wild-type translation initiation factor eIF(iso)4E gene which encodes a translation initiation factor eIF(iso)4E protein consisting of an amino acid sequence represented by SEQ ID NO: 4, (b) a wild-type translation initiation factor eIF(iso)4E gene which encodes a functional translation initiation factor eIF(iso)4E protein having a sequence identity of 92% or higher with the amino acid sequence represented by SEQ ID NO: 4, (c) a wild-type translation initiation factor eIF(iso)4E gene which causes production of mRNA consisting of a base sequence represented by SEQ ID NO: 6, or (d) a wild-type translation initiation factor eIF(iso)4E gene which causes production of mRNA having a sequence identity of 92% or higher with the base sequence represented by SEQ ID NO: 6 and encodes a functional translation initiation factor eIF(iso)4E protein, and the virus is a virus belonging to the genus Potyvirus.

The virus belonging to the genus Potyvirus is preferably a strain of Potato virus Y, the strain breaking virus resistance of Virgin A mutant of tobacco.

Another aspect of the virus-resistant tobacco in accordance with the present invention is such that an expression level of a translation initiation factor eIF(iso)4E gene is 20% or lower, as compared to a wild type.

The another aspect of the virus-resistant tobacco in accordance with the present invention is more preferably such that the expression level is 10% or lower as compared to the wild type.

The another aspect of the virus-resistant tobacco in accordance with the present invention may be such that the virus-resistant tobacco retains an RNAi construct for suppressing expression of the translation initiation factor eIF(iso)4E gene.

An aspect of a method for producing a virus-resistant tobacco in accordance with the present invention, includes introducing a mutation to a translation initiation factor eIF(iso)4E gene, the mutation causing production of a translation initiation factor eIF(iso)4E protein which is non-functional with respect to a virus or suppressing expression of the translation initiation factor eIF(iso)4E gene, in order to produce tobacco having resistance to a virus.

The aspect of the method for producing a virus-resistant tobacco in accordance with the present invention is preferably such that the mutation is a nonsense mutation.

The aspect of the method for producing a virus-resistant tobacco in accordance with the present invention is preferably such that the mutation is caused by ethyl methane sulfonate.

The aspect of the method for producing a virus-resistant tobacco in accordance with the present invention may be such that the mutation is one or more of the following mutations (1) to (4): (1) C of codon CAA is substituted by T; (2) C of codon CGA is substituted by T; (3) C of codon CAG is substituted by T; and (4) G (either one or both of two Gs) of codon TGG is substituted by A, in (a) an exon of a wild-type translation initiation factor eIF(iso)4E gene which encodes a translation initiation factor eIF(iso)4E protein consisting of an amino acid sequence represented by SEQ ID NO: 3 or SEQ ID NO: 4, (b) an exon of a wild-type translation initiation factor eIF(iso)4E gene which encodes a functional translation initiation factor eIF(iso)4E protein having a sequence identity of 92% or higher with the amino acid sequence represented by SEQ ID NO: 3 or SEQ ID NO: 4, (c) an exon of a wild-type translation initiation factor eIF(iso)4E gene which causes production of mRNA consisting of a base sequence represented by SEQ ID NO: 5 or SEQ ID NO: 6, or (d) an exon of a wild-type translation initiation factor eIF(iso)4E gene which causes production of mRNA having a sequence identity of 92% or higher with the base sequence represented by SEQ ID NO: 5 or SEQ ID NO: 6 and encodes a functional translation initiation factor eIF(iso)4E protein.

The aspect of the method for producing a virus-resistant tobacco in accordance with the present invention may be such that the mutation is one or more of the following mutations (1) to (27): (1) C to T substitution at position 270, (2) G to A substitution at position 295, (3) G to A substitution at position 296, (4) G to A substitution at position 304, (5) G to A substitution at position 305, (6) C to T substitution at position 315, (7) C to T substitution at position 330, (8) G to A substitution at position 343, (9) G to A substitution at position 344, (10) C to T substitution at position 357, (11) G to A substitution at position 394, (12) G to A substitution at position 395, (13) C to T substitution at position 1740, (14) G to A substitution at position 1813, (15) G to A substitution at position 1814, (16) G to A substitution at position 1846, (17) G to A substitution at position 1847, (18) G to A substitution at position 1888, (19) G to A substitution at position 1889, (20) C to T substitution at position 2050, (21) C to T substitution at position 2104, (22) G to A substitution at position 2123, (23) G to A substitution at position 2124, (24) C to T substitution at position 2152, (25) G to A substitution at position 4742, (26) G to A substitution at position 4743, and (27) C to T substitution at position 4926, in a translation initiation factor eIF(iso)4E gene consisting of a base sequence represented by SEQ ID NO: 7 in genomic DNA.

The aspect of the method for producing a virus-resistant tobacco in accordance with the present invention may be such that the mutation is one or more of the following mutations (1) to (26): (1) C to T substitution at position 264, (2) G to A substitution at position 289, (3) G to A substitution at position 290, (4) G to A substitution at position 298, (5) G to A substitution at position 299, (6) C to T substitution at position 315, (7) G to A substitution at position 328, (8) G to A substitution at position 329, (9) C to T substitution at position 342, (10) G to A substitution at position 379, (11) G to A substitution at position 380, (12) C to T substitution at position 1630, (13) G to A substitution at position 1703, (14) G to A substitution at position 1704, (15) G to A substitution at position 1736, (16) G to A substitution at position 1737, (17) G to A substitution at position 1778, (18) G to A substitution at position 1779, (19) C to T substitution at position 1940, (20) C to T substitution at position 1994, (21) G to A substitution at position 2013, (22) G to A substitution at position 2014, (23) C to T substitution at position 2042, (24) G to A substitution at position 3224, (25) G to A substitution at position 3225, and (26) C to T substitution at position 3406, in a translation initiation factor eIF(iso)4E gene consisting of a base sequence represented by SEQ ID NO: 8 in genomic DNA.

Another aspect of the method for producing a virus-resistant tobacco in accordance with the present invention includes introducing a factor that suppresses an expression level of a translation initiation factor eIF(iso)4E gene to 20% or lower as compared to a wild type, in order to produce tobacco having resistance to a virus.

The another aspect of the method for producing a virus-resistant tobacco in accordance with the present invention is more preferably such that a factor that suppresses the expression level to 10% or lower as compared to the wild type is introduced into tobacco.

The another aspect of the method for producing a virus-resistant tobacco in accordance with the present invention is preferably such that the factor is an RNAi construct.

A method for producing a virus-resistant tobacco in accordance with the present invention is preferably such that the virus is a virus belonging to the genus Potyvirus.

A method for producing a virus-resistant tobacco in accordance with the present invention is more preferably such that the virus belonging to the genus Potyvirus is Potato virus Y.

A method for producing a virus-resistant tobacco in accordance with the present invention is more preferably such that the virus belonging to the genus Potyvirus is a strain of Potato virus Y, the strain breaking virus resistance of Virgin A mutant of tobacco.

A method for producing a virus-resistant tobacco in accordance with the present invention is preferably such that the virus is a virus belonging to the genus Umbravirus.

A method for producing a virus-resistant tobacco in accordance with the present invention is more preferably such that the virus belonging to the genus Umbravirus is Tobacco bushy top virus.

An aspect of a detection-use polynucleotide in accordance with the present invention is a polynucleotide for detecting a mutation in a translation initiation factor eIF(iso)4E gene of tobacco, the mutation causing production of a translation initiation factor eIF(iso)4E protein which is non-functional with respect to a virus or suppressing expression of the translation initiation factor eIF(iso)4E gene.

The aspect of the detection-use polynucleotide in accordance with the present invention is preferably such that the mutation is a nonsense mutation.

The aspect of the detection-use polynucleotide in accordance with the present invention may be such that the mutation is one or more of the following mutations (1) to (4): (1) C of codon CAA is substituted by T; (2) C of codon CGA is substituted by T; (3) C of codon CAG is substituted by T; and (4) G (either one or both of two Gs) of codon TGG is substituted by A, in (a) an exon of a wild-type translation initiation factor eIF(iso)4E gene which encodes a translation initiation factor eIF(iso)4E protein consisting of an amino acid sequence represented by SEQ ID NO: 3 or SEQ ID NO: 4, (b) an exon of a wild-type translation initiation factor eIF(iso)4E gene which encodes a functional translation initiation factor eIF(iso)4E protein having a sequence identity of 92% or higher with the amino acid sequence represented by SEQ ID NO: 3 or SEQ ID NO: 4, (c) an exon of a wild-type translation initiation factor eIF(iso)4E gene which causes production of mRNA consisting of a base sequence represented by SEQ ID NO: 5 or SEQ ID NO: 6, or (d) an exon of a wild-type translation initiation factor eIF(iso)4E gene which causes production of mRNA having a sequence identity of 92% or higher with the base sequence represented by SEQ ID NO: 5 or SEQ ID NO: 6 and encodes a functional translation initiation factor eIF(iso)4E protein.

The aspect of the detection-use polynucleotide in accordance with the present invention may be such that the mutation is one or more of the following mutations (1) to (27): (1) C to T substitution at position 270, (2) G to A substitution at position 295, (3) G to A substitution at position 296, (4) G to A substitution at position 304, (5) G to A substitution at position 305, (6) C to T substitution at position 315, (7) C to T substitution at position 330, (8) G to A substitution at position 343, (9) G to A substitution at position 344, (10) C to T substitution at position 357, (11) G to A substitution at position 394, (12) G to A substitution at position 395, (13) C to T substitution at position 1740, (14) G to A substitution at position 1813, (15) G to A substitution at position 1814, (16) G to A substitution at position 1846, (17) G to A substitution at position 1847, (18) G to A substitution at position 1888, (19) G to A substitution at position 1889, (20) C to T substitution at position 2050, (21) C to T substitution at position 2104, (22) G to A substitution at position 2123, (23) G to A substitution at position 2124, (24) C to T substitution at position 2152, (25) G to A substitution at position 4742, (26) G to A substitution at position 4743, and (27) C to T substitution at position 4926, in a translation initiation factor eIF(iso)4E gene consisting of a base sequence represented by SEQ ID NO: 7 in genomic DNA.

The aspect of the detection-use polynucleotide in accordance with the present invention may be such that the mutation is one or more of the following mutations (1) to (26): (1) C to T substitution at position 264, (2) G to A substitution at position 289, (3) G to A substitution at position 290, (4) G to A substitution at position 298, (5) G to A substitution at position 299, (6) C to T substitution at position 315, (7) G to A substitution at position 328, (8) G to A substitution at position 329, (9) C to T substitution at position 342, (10) G to A substitution at position 379, (11) G to A substitution at position 380, (12) C to T substitution at position 1630, (13) G to A substitution at position 1703, (14) G to A substitution at position 1704, (15) G to A substitution at position 1736, (16) G to A substitution at position 1737, (17) G to A substitution at position 1778, (18) G to A substitution at position 1779, (19) C to T substitution at position 1940, (20) C to T substitution at position 1994, (21) G to A substitution at position 2013, (22) G to A substitution at position 2014, (23) C to T substitution at position 2042, (24) G to A substitution at position 3224, (25) G to A substitution at position 3225, and (26) C to T substitution at position 3406, in a translation initiation factor eIF(iso)4E gene consisting of a base sequence represented by SEQ ID NO: 8 in genomic DNA.

The aspect of the detection-use polynucleotide in accordance with the present invention is a set of nucleic-acid primers flanking the mutation or a set of nucleic-acid primers which contains a polynucleotide consisting of a continuous base sequence which contains the mutation or a sequence complementary to the continuous base sequence.

An aspect of a method of selecting a virus-resistant tobacco in accordance with the present invention includes: an examination step of examining tobacco for presence or absence of a mutation in genomic DNA by using the detection-use polynucleotide recited in any one of claims 27 to 32; and a selection step of selecting, as a virus-resistant tobacco, tobacco in which the mutation has been detected in the examination step.

An aspect of a DNA marker for evaluating tobacco for resistance to a virus in accordance with the present invention, includes: a polynucleotide consisting of a continuous base sequence which contains a mutation in a translation initiation factor eIF(iso)4E gene or a sequence complementary to the continuous base sequence, the mutation causing production of a translation initiation factor eIF(iso)4E protein which is non-functional with respect to a virus or suppressing expression of the translation initiation factor eIF(iso)4E gene.

In any plants, only eIF4E was previously mentioned about its association with PVY resistance, and no information about association of eIF(iso)4E with PVY resistance was disclosed. There was a report of tobacco in which an eIF(iso)4E expression level is decreased to a given degree, but no mention was made of association with virus resistance. As for tobacco, there was a report of association between PVY resistance and eIF4E, but no association between Potyvirus resistance and a mutation of eIF4E or eIF(iso)4E. Thus, the situation was still in chaos. Regarding a virus belonging to the genus Umbravirus, association between resistance to that virus and a translation initiation factor was not pointed out at all. Besides, the situation was such that it was impossible to easily predict a tobacco gene responsible for resistance to the PVY-Breaking strain or TBTV for the following reasons. One reason is that a candidate for a host factor required for virus reproduction was not only the translation initiation factor, but also many candidates including, for example, DEAD-box RNA helicase-like protein, VPg-interacting protein, and Translation elongation factor, as described earlier. Another reason is that since many genes are present in the eIF4E family of tobacco, much effort and much time are required to find an effective gene out of those genes.

The following description will discuss details of the embodiment of the present invention with reference to Examples. The present invention is of course not limited to the Examples below and particulars can have various aspects. Further, the present invention is not limited to the embodiments, but can be altered by a skilled person in the art within the scope of the claims. An embodiment derived from a proper combination of technical means disclosed in respective different embodiments is also encompassed in the technical scope of the present invention. Moreover, all the literatures described in this specification are hereby incorporated by reference.

EXAMPLES

Example 1

(Gene Acquisition)

Known databases were searched to acquire the cDNA sequence (SEQ ID NO: 10) of a translation initiation factor eIF4E1 (GenBank accession number: AY702653) and the cDNA sequence (SEQ ID NO: 1) of a translation initiation factor eIF(iso)4E (GenBank accession number: AY699609) of tobacco (*Nicotiana tabacum*).

By BLAST analysis using the Whole-genome shotgun contigs (WGS) of the GenBank database, it was found that eIF(iso)4E assigned accession number AY699609 is derived from *Nicotiana sylvestris*. Further, two sequences assigned GenBank accession numbers EB683576 (SEQ ID NO: 2) and FN666434 were identified as *Nicotiana tomentosiformis*-derived tobacco (*Nicotiana tabacum*) eIF(iso)4E. These genes or pieces of sequence information thereof were subjected to the following experiment. FN666434, which is a sequence derived from a T-type eIF(iso)4E gene derived from tobacco variety Samsun NN, had a sequence identity of 97% with the sequence (EB683576) of the aforementioned T-type eIF(iso)4E derived from tobacco variety K326. Proteins encoded by these two genes showed an amino acid sequence identity (identity) of 97% and an amino acid sequence similarity (similarity) of 99%. Such a sequence difference between them was attributed to a difference in origin variety between them. Further, the S-type eIF(iso)4E (AY699609) and the T-type eIF(iso)4E (EB683576) showed a DNA sequence identity of 91%. The amino acid sequence (SEQ ID NO: 3) of the S-type eIF(iso)4E and the amino acid sequence (SEQ ID NO: 4) of the T-type eIF(iso)4E showed an identity of 91% and a similarity of 96%. For analyses of sequence identities, etc., nucleic acid and amino acid sequence analysis software GENETYX (registered trademark) (ver.12) (GENETYX CORPORATION) was used.

(Construction of RNAi Constructs)

In order to produce eIF4E1 expression-suppressed tobacco and eIF(iso)4E expression-suppressed tobacco, RNAi constructs having respective internal sequences of those genes as triggers were constructed independently.

First, primers for specifically amplifying an eIF4E1 trigger sequence (SEQ ID NO: 11) and an eIF(iso)4E trigger sequence (SEQ ID NO: 9) were produced (Table 1). A CACC sequence for use in cloning discussed later was added to the 5 end of a FW primer for each gene.

TABLE 1

Table 1: Primers for cloning of RNAi trigger sequence of translation initiation factor

| Name of primer | Sequence (5'-3') | Target gene | SEQ ID NO: |
|---|---|---|---|
| Nt-eIF4E1-FW (CACC) | CACCGAAGACTAATACTCGTGAGG | Nt-eIF4E1 | SEQ ID NO: 12 |
| Nt-eIF4E1-RV | TCCGTTGGCGCAGACAGG | | SEQ ID NO: 13 |
| Nt-eIF(iso)4E-FW (CACC) | CACCAGAGGCGACGGAGGTTCC | Nt-eIF(iso)4E | SEQ ID NO: 14 |
| Nt-eIF(iso)4E-RV | TCTGCTGCTCGTAACAGTCC | | SEQ ID NO: 15 |

By using MagDEA (Registered Trademark) RNA100 (GC) (Precision System Science Co., Ltd.), RNA was extracted from tobacco seedling and purified. Then, PrimeScript™ RT reagent kit (Takara-Bio Inc.) was used to synthesize cDNA from the purified RNA. With use of the cDNA as a template and the gene-specific primers shown in Table 1, gene fragments of eIF4E1 and eIF(iso)4E were amplified. Specifically, 10 ng of the template DNA and 5 pmoles each of the primers were contained in a 20 µL reaction solution, PrimeSTAR Max DNA Polymerase (Takara-Bio Inc.) was used as an enzyme, and a reaction was performed under the following conditions: 35 cycles of 98° C. for 10 seconds, 55° C. for 15 seconds, and 72° C. for 15 seconds. PCR products (approximately 320 bp for eIF4E1; approximately 310 bp for eIF(iso)4E) were purified by using MiniElute PCR Purification kit (Qiagen Inc.). Thereafter, the purified PCR products were cloned in a vector pENTR™/D-TOPO (Registered Trademark) (Life Technologies Corporation). After the base sequence of the insert was confirmed, GateWay (Registered Trademark) LR Clonase (Registered Trademark) II Enzyme mix (Life Technologies Corporation) were used to clone the insert into RNAi vector pSP231 (see the literature: International publication WO2011/102394). The vector pSP231, which is a vector in which a GFP (Green-fluorescent protein gene) expression cassette was inserted into a SacI site of pHellsgate 12 (see the literature: Wesley et al., 2001, Plant J., 27, 581-590), is a binary vector that drives, with a cauliflower mosaic virus 35SRNA gene promotor, a RNAi sequence formed with a pdk/cat intron located between inverted repeat sequences of the trigger sequence. After the cloning into pSP231, an RNAi trigger sequence and its orientation were confirmed. As a result, a final RNAi construct was obtained.

The RNAi construct thus prepared was introduced into *Agrobacterium* LBA4404 strain by electroporation method.

(Tobacco transformation) Transformation of tobacco was carried out by a usual method (leaf disc method). As Tobacco variety, Petit Havana SR1 was used.

Tobacco cotyledon was cut at four corners thereof, and leaf segments thus obtained were immersed in an *Agrobacterium* solution for 10 minutes. The leaf segments were wiped dry and then placed on an LS solid medium (containing 3% sucrose and 0.8% agar). The leaf segments were cultured in the dark at 25° C. for 3 days so that tobacco was infected with recombinant *Agrobacterium* to introduce the RNAi construct of each translation initiation factor into SR1. The leaf segments were placed for 4 days on an LS solid medium containing 250 mg/L of Cefotaxime, 2-isopentenyl adenine (2iP) (10 mg/L), and IAA (0.3 mg/L), both of which are plant hormones, to eradicate *Agrobacterium* therefrom. Selection of a recombinant was carried out on an LS medium containing Cefotaxime and the plant hormones in the above concentrations and further containing 50 mg/L kanamycin. A shoot, which had been redifferentiated from the selected recombinant, was placed on a rooting medium (LS solid medium containing 1.5% sucrose, 0.3% gellan gum and further containing Cefotaxime and kanamycin in the above concentrations) so that it was rooted. The resulting recombinant tobacco was cultivated in a greenhouse.

(Transcriptional Analysis of the Translation Initiation Factor in the Recombinant Tobacco at the Original Generation of Transformation)

In order to examine expression of eIF4E1 or eIF(iso)4E gene in the recombinant tobacco, a set of primers and a probe for real-time PCR were designed based on the base sequence of each gene (Table 2). Further, total RNA was extracted from a leaf of each recombinant tobacco by using RNeasy Plant Mini Kit (QIAGEN Inc.). Synthesis of cDNA from the obtained RNA was performed by using Prime Script reagent Kit (Takara-Bio Inc.), and the cDNA was used as a template for real-time PCR. In the real-time PCR, TaqMan Fast Advanced Master mix (Life Technologies Corporation) was used to perform amplification reaction. The reaction was performed under the following conditions: 50° C. for 2 minutes and 95° C. for 20 seconds, followed by 40 cycles of 95° C. for 1 second and 60° C. for 20 seconds. Expression analysis was performed using StepOne Software v2.2 (Life Technologies Corporation). As an internal standard for PCR, an elongation factor 1-alpha (EF1-α) gene was used. For comparison to an expression level of the EF1-α gene, a relative gene expression level of a target gene was calculated. As a control, a non-recombinant tobacco (SR1) was used.

TABLE 2

Table 2: Primers and a probe for quantitative PCR

| Target gene | Primers/Probe | Sequence (5'-3') | SEQ ID NO: |
|---|---|---|---|
| eIF4E1 | Forward | CGAGTTAGACAAGAAAAAATAGCTTTGT | SEQ ID NO: 16 |
|  | Reverse | ATCCAGAAATTCTTCCAYTGTTT* | SEQ ID NO: 17 |
|  | Probe | ACCAGGAATGCTGCCAATGAAACAGC | SEQ ID NO: 18 |
| eIF(iso)4E | Forward | GCCACTGAAGCACCGATAGAG | SEQ ID NO: 19 |
|  | Reverse | TTATCGAACCAGAATGTCCATCTC | SEQ ID NO: 20 |
|  | Probe | TCCGCCGGCGTCAGCGAC | SEQ ID NO: 21 |
| EF-α | Forward | CTAAGGGTGCTGCCAGCTTT | SEQ ID NO: 22 |
|  | Reverse | GTCAAGCACTGGAGCATATCCA | SEQ ID NO: 23 |
|  | Probe | ATCATGAACCATCCAGGACAGATTGG | SEQ ID NO: 24 |

*Y = C/T

As a result, the amount of transcripts of eIF4E1 genes in the tobacco into which the RNAi construct of eIF4E1 had been introduced and the amount of transcripts of eIF(iso)4E gene in the tobacco into which the RNAi construct of the eIF(iso)4E had been introduced, were much lower than expression levels in the control. As lines exhibiting a high degree of eIF4E1 transcription inhibition in the transformant at the original generation, were selected the following five lines: #1, #2, #3, #7, and #8 (their transcript amounts were 1%, 1%, 1%, 36%, and 1% of expression levels in the control variety SR1). As lines exhibiting a high degree of eIF(iso)4E transcription suppression in the transformant in the original generation, were selected the following three lines: #1, #7, and #15 (their transcript amounts were 4%, 6%, and 5% of expression levels in the control variety SR1).

(Segregation of the Recombinant Tobacco at the Next Generation of Transformation)

Seeds of the five lines exhibiting a high degree of eIF4E1 transcription suppression in the transformant at the original generation and seeds of the three lines exhibiting a high degree of eIF(iso)4E transcription suppression in the transformant at the original generation were aseptically sown on an LS solid medium (containing 3% sucrose and 0.8% agar). GFP fluorescences of seedling plants which had germinated and grown were measured by using Fluor Imager 595 (Molecular Dynamics, Inc.). As described earlier, pSP231 used for construct introduction includes a 35S promoter-GFP expression cassette provided next to the RNAi expression cassette on the T-DNA region. The seedling plants that had emit strong GFP fluorescence was determined to be homozygous lines for RNAi construct, the seedling plants that had emit no fluorescence was determined to be null segregant lines for RNAi construct (in which none of the RNAi constructs were present), and the seedling plants that had emit weak fluorescence was determined to be hemizygous lines for RNAi construct. Three weeks after the sowing, the plants were transferred to a greenhouse and then planted and cultivated on a culture soil.

(Transcriptional Analysis of the Translation Initiation Factor in the Recombinant Tobacco at the Next Generation of Transformation)

In order to examine expression of eIF(iso)4E gene in the next generation of each line of the recombinant tobacco, RNA was extracted from a leaf of the recombinant tobacco, and cDNA was synthesized from the RNA and was used a template for real-time PCR, as discussed earlier. The real-time PCR was performed as in the manner discussed earlier. As an internal standard for PCR, EF1-α gene was used. As a control plant, a non-recombinant tobacco (SR1) was used.

Figure 1:
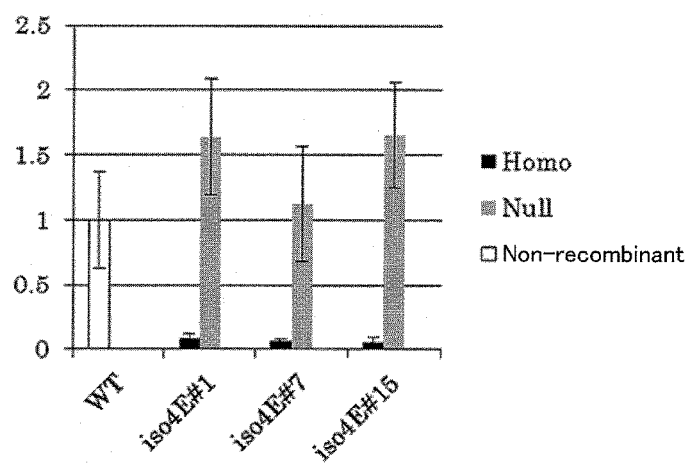
FIG. 1 is a graph showing the result of eIF(iso)4E gene expression analysis by real-time PCR (values relative to a value of WT which is a non-recombinant) in Example of the present invention, wherein error bars represent standard deviations.

From the result of eIF(iso)4E gene expression analysis by the real-time PCR (FIG. 1), it was confirmed that the homozygous lines of the eIF(iso)4E expression suppression lines #1, #7, and #15 suppressed the expression to approximately 8%, 6%, and 6% of the expression in the non-recombinant line (SR1), respectively. It was also confirmed that the expression suppression did not occur in the null segregant lines of the three eIF(iso)4E expression suppression lines.

(Virus Inoculation Tests on Recombinant Tobacco Plants in which Transcription of the Translation Initiation Factor was Suppressed)

Individual plants 7 to 10 days after transplantation into a culture soil were inoculated with PVY (PVY-N), PVY-B, or TBTV (Tobacco bushy top virus). PVY-B, which is a virus strain that was isolated at the Leaf Tobacco Research Center of Japan Tobacco Inc., is a VAM breaking strain that causes a necrosis symptom in the existing tobacco variety Virgin A mutant, which is PVY resistant. TBTV, which is a virus belonging to the genus Umbravirus, causes a mottling symptom on a leaf of tobacco. As an inoculum, a leaf of flue-cured tobacco, Tsukuba 1, which had been infected with each virus and developed a disease symptom was used. The variety Tsukuba 1 is susceptible to PVY, PVY-B, and TBTV, and shows clear disease symptoms. The infected leaf was collected and then ground in 0.01N phosphate buffer solution in a mortar. Virus was inoculated by rubbing a viral solution obtained by the grinding with use of carborundum into a half of the largest leaf of a tobacco seedling one week after the transplantation (fourth or fifth leaf from the bottom). Thereafter, the individuals were cultivated in a greenhouse, and their disease symptoms were observed in a timely manner.

As a result, most of the individuals of the eIF4E1 function-suppressed tobacco lines (eIF4E1#1, eIF4E1#2, eIF4E1#3, eIF4E1#7, eIF4E1#8) showed the symptoms of diseases caused by PVY, PVY-B, and TBTV. They were susceptible to those viruses. In this point, there was practically no difference from the control variety and the null segregant lines.

Table 3 shows results of virus inoculation tests of the eIF(iso)4E function-suppressed tobacco.

In a disease symptom evaluation on the 7th day after PVY-B inoculation, the symptom was not observed in the individuals (a total of 9 individuals) in the three homozygous lines of the eIF(iso)4E function-suppressed tobacco (eIF(iso)4E#1, eIF(iso)4E#7, eIF(iso)4E#15). In all of the individuals in the null segregant lines having no RNAi construct for eIF(iso)4E and the control variety SR1, the symptoms of the disease was observed. This proved that the eIF(iso)4E function-suppressed tobacco has resistance to PVY-B. It was considered that replication or cell-to-cell movement of the virus was inhibited in the eIF(iso)4E function-suppressed tobacco (tobacco with a reduced amount of transcripts of eIF(iso)4E). On the other hand, the symptoms of a disease caused by PVY was observed in 5 individuals of the 9 individuals of the homozygous three lines of the eIF(iso)4E function-suppressed tobacco, but was not observed in 4 individuals out of the 9 individuals. Growth inhibition of the eIF(iso)4E function-suppressed tobacco was not observed at all.

In a disease symptom evaluation on the 9th day after TBTV inoculation, the symptom of a disease was not observed in the individuals (a total of 9 individuals) in the homozygous three lines of the eIF(iso)4E function-suppressed tobacco (eIF(iso)4E#1, eIF(iso)4E#7, eIF(iso)4E#15). In contrast, the symptom of the disease was observed in all of the individuals in the null segregant lines having no RNAi construct for eIF(iso)4E and the control variety SR1. This proved that the eIF(iso)4E function-suppressed tobacco has resistance to TBTV.

The above results demonstrate that suppression of the function of the translation initiation factor eIF(iso)4E in tobacco enables imparting PVY-B and TBTV resistance to tobacco.

the T-type eIF(iso)4E gene). Both of the sequences are genomic sequences derived from the tobacco variety K326.

Further, it was found that the eIF(iso)4E genes consist of five exons and four introns. FIG. 2 is a diagram of an exon-intron structure of an S-type eIF(iso)4E gene. FIG. 3 is a diagram of an exon-intron structure of a T-type eIF(iso)4E gene. In FIGS. 2 and 3, numbers provided in lower parts of FIGS. 2 and 3 indicate the numbers of positions at which potential nonsense mutations occur when the EMS treatment causes a G to A mutation or a C to T mutation, and arrows indicate the positions of primers in the Examples. In the case of the S-type eIF(iso)4E, the bases that can turn into stop codons when the EMS treatment causes a G to A mutation or a C to T mutation were 12 bases in the first exon (in SEQ ID NO: 7, C at position 270, G at position 295, G at position 296, G at position 304, G at position 305, C at position 315, C at position 330, G at position 343, G at position 344, C at position 357, G at position 394, and G at position 395), 7 bases in the second exon (C at position 1740, G at position 1813, G at position 1814, G at position 1846, G at position 1847, G at position 1888, and G at position 1889), 5 bases in the third exon (C at position 2050, C at position 2104, G at position 2123, G at position 2124, and C at position 2152), 2 bases in the fourth exon (G at position 4742 and G at position 4743), and one base in the fifth exon (C at position 4926).

Meanwhile, in the case of the T-type eIF(iso)4E, the bases that can turn into stop codons when the EMS treatment causes a G to A mutation or a C to T mutation were 11 bases in the first exon (in SEQ ID NO: 8, C at position 264, G at position 289, G at position 290, G at position 298, G at position 299, C at position 315, G at position 328, G at position 329, C at position 342, G at position 379, and G at position 380), 7 bases in the second exon (C at position 1630, G at position 1703, G at position 1704, G at position 1736, G at position 1737, G at position 1778, and G at position 1779), 5 bases in the third exon (C at position 1940, C at position 1994, G at position 2013, G at position 2014, and C at position 2042), 2 bases in the fourth exon (G at position 3224 and G at position 3225), and one base in the fifth exon (C at position 3406).

For the first exon and a combination of the second exon and the third exon, primers were designed for amplifying a region containing the exon(s) and the boundary sites between an exon and an intron (Table 4). In Table 4, "S-type eIF(iso)4E" refers to *Nicotiana sylvestris*-derived eIF(iso) 4E (*Nicotiana tabacum* sequence), "T-type eIF(iso)4E"

TABLE 3

Results of virus inoculation tests on recombinant tobaccos in which transcription of the translation initiation factor is suppressed

| Line | | Expression Level | PVY (7 days after inoculation) (Number of individuals showing disease symptom/number of individuals under test | PVY-B (7 days after inoculation) (Number of individuals showing disease symptom/number of individuals under test | TBTV (9 days after inoculation) (Number of individuals showing disease symptom/number of individuals under test |
|---|---|---|---|---|---|
| eIF(iso)4E #1 | Homo | 8% of WT | 3/3 | 0/3 | 0/3 |
| | Null | Same as WT | 1/1 | 1/1 | 1/1 |
| eIF(iso)4E #7 | Homo | 6% of WT | 1/3 | 0.3 | 0/3 |
| | Null | Same as WT | 1/2 | 2/2 | 2/2 |
| eIF(iso)4E #15 | Homo | 6% of WT | 1/3 | 0/3 | 0/3 |
| | Null | Same as WT | 2/2 | 2/2 | 3/3 |
| eIF(iso)4E | Homo | 6-8% of WT | 5/9 (56%) | 0/9 (0%) | 0/9 (0%) |
| Total | Null | Same as WT | 4/5 (80%) | 5/5 (100%) | 6/6 (100%) |
| SR1 (Control-WT) | | | 5/5 (100%) | 5/5 (100%) | 5/5 (100%) |

Example 2

(Screening of eIF(Iso)4E Tobacco Mutant)

Searches of the Whole Genome Shotgun Contigs of *Nicotiana tabacum* in the GenBank database were conducted using mRNA sequences of the S-type eIF(iso)4E (AY699609) and T-type eIF(iso)4E (EB683576). As a result, genomic sequences showing 100% sequence identity in a protein coding region other than the intron regions were acquired (accession number for the S-type eIF(iso)4E was AWOJ01412288, and accession number for the T-type eIF (iso)4E was AWOJ01054542). In these whole contig sequences, sequences of each eIF(iso)4E genes were represented by SEQ ID NO: 7 (genomic sequence of the S-type eIF(iso)4E gene) and SEQ ID NO: 8 (genomic sequence of refers to *Nicotiana tomentosiformis*-derived eIF(iso)4E (*Nicotiana tabacum* sequence).

TABLE 4

Table 4: Primers for tobacco mutant screening

| Target site | Primer | Sequence (5'-3') | SEQ ID NO: |
|---|---|---|---|
| S-type eIF(iso)4E Exon 1 Combination 1 | Forward Reverse | GGCCTAAACGTTGTAAGACAA TGCTTAGTTAAATGCTACAGGG | SEQ ID NO: 25 SEQ ID NO: 26 |
| S-type eIF(iso)4E Exon 1 Combination 2 | Forward Reverse | TTACGCCTCTCCGTTCGCTA TGCTTAGTTAAATGCTACAGGG | SEQ ID NO: 27 SEQ ID NO: 26 |
| S-type eIF(iso)4E Exons 2 & 3 Combination 1 | Forward Reverse | CTGGGTTTGTTGTTGTAAAGTA CACAGTTTTCAGTTCAGTAAC | SEQ ID NO: 28 SEQ ID NO: 29 |
| S-type eIF(iso)4E Exons 2 & 3 Combination 2 | Forward Reverse | CTGGGTTTGTTGTTGTAAAGTA GATGGGCCATATCATCATCAT | SEQ ID NO: 28 SEQ ID NO: 30 |
| T-type eIF(iso)4E Exon 1 Combination 1 | Forward Reverse | GACCTGAACATTGCAAGATGA GGCTTACTTGAATGCTACAAGG | SEQ ID NO: 31 SEQ ID NO: 32 |
| T-type eIF(iso)4E Exon 1 Combination 2 | Forward Reverse | TTACGCCTCAATCGACACAA GGCTTACTTGAATGCTACAAGG | SEQ ID NO: 33 SEQ ID NO: 32 |
| T-type eIF(iso)4E Exons 2 & 3 Combination 1 | Forward Reverse | CCCCAGTAATGGATTCTACC ATCAGATTTAGGATATAGGGG | SEQ ID NO: 34 SEQ ID NO: 35 |
| T-type eIF(iso)4E Exons 2 & 3 Combination 2 | Forward Reverse | CCCCAGTAATGGATTCTACC CAGATACTATTTGACACCAC | SEQ ID NO: 34 SEQ ID NO: 36 |

PCR was performed, and base sequences of the products thus obtained were confirmed. Using 5 ng of tobacco (variety: Tsukuba No. 1) genome, PCR was performed in a 20 μL reaction system. As an enzyme, Tks Gflex™ DNA Polymerase (Takara-Bio Inc.) was used. The reaction was performed under the following conditions: 94° C. for 2 minutes followed by 40 cycles of 94° C. for 30 seconds, 60° C. for 30 seconds, and 72° C. for 90 seconds. As a result, all the products thus obtained were of a desired length, and their base sequences were confirmed. That is, S-type specific and T-type specific eIF(iso)4E gene regions were successfully amplified from a tobacco genome by using the above primers.

By extracting genomic DNAs from individuals having a mutation caused by an EMS treatment, performing PCR with use of the above primers to amplify S-type specific and T-type specific eIF(iso)4E gene regions, and confirming base sequences of amplified products, eIF(iso)4E tobacco mutants having stop codons occurring within the first exon, the second exon, or the third exon were screened.

Specifically, screening was performed using a tobacco mutant library prepared by Tajima et al. (Literature: The 2011 Annual Meeting of the Phytopathological Society of Japan, P234, "Construction of mutant panel in *Nicotiana tabacum* L."). This panel consists of (i) a set of seeds (M2 bulk seeds) of selfed mutant progeny obtained from each individual (M1 generation) bred from (several thousands of) seeds of the tobacco variety Tsukuba No. 1, which seeds were subjected to the EMS treatment as a mutagen treatment, and (ii) a set of bulk DNA extracted from seedlings of 8 individuals of each line grown from the sown M2 seeds.

(Screening of S-Type Mutant of eIF(Iso)4E Gene)

Using the DNA samples (DNA samples of 1974 lines) as templates, PCR was performed with use of the primers represented by "S-type eIF(iso)4E-Exon 1 Combination 1 (SEQ ID NO: 25 and SEQ ID NO: 26)" and the primers represented by "S-type eIF(iso)4E-Exons 2863 Combination 1 (SEQ ID NO: 28 and SEQ ID NO: 29)" out of the primers shown in Table 4. Subsequently, base sequences of the PCR products thus obtained were determined. As a result, mutations in Exon 1 were detected in 58 samples (50 positions), and mutations in Exon 2 and Exon 3 were detected in a total of 58 samples (45 positions). All of the mutations were heterozygous mutations. Samples in which a nonsense mutation (a mutation that caused stop codon) was detected in Exon 1 were 4 samples (in SEQ ID NO: 7, a G to A mutation at position 295, 394, or 395 or a C to T mutation at position 330). A sample in which a nonsense mutation was detected in Exons 2 and 3 was one sample (in SEQ ID NO: 7, a G to A mutation at position 1814). Out of these lines, seeds of the line (M2) having a C to T mutation at position 330 were sown, DNAs were extracted from 24 individuals of that line, and their base sequences were determined. As a result, 11 individuals each having a target mutation as homozygous mutation (eIF(iso)4E_S-type mutant homozygotes) were obtained.

(Screening of T-type mutant of eIF(iso)4E gene)

Using the DNA samples (DNA samples of 1974 lines) as templates, PCR was performed with use of the primers represented by "T-type eIF(iso)4E-Exon 1 Combination 1 (SEQ ID NO: 31 and SEQ ID NO: 32)" and the primers represented by "T-type eIF(iso)4E-Exons 2863 Combination 2 (SEQ ID NO: 34 and SEQ ID NO: 36)" out of the primers shown in Table 4. Subsequently, base sequences of the PCR products thus obtained were determined in the same manner as in the above case. As a result, mutations in Exon 1 were detected in 43 samples (38 positions), and mutations in Exon 2 and Exon 3 were detected in a total of 66 samples (55 positions). All of the mutations were heterozygous mutations. Samples in which a nonsense mutation was detected in Exon 1 were 5 samples (in SEQ ID NO: 8, a G to A mutation at position 289, 299, 328, 329, or 380). Samples in which a nonsense mutation was detected in Exons 2 and 3 were 4 samples (3 samples had a G to A mutation at position 1704 in SEQ ID NO: 8, and one sample had a G to A mutation at position 1737 in SEQ ID NO: 8). DNAs were extracted from 24 individuals of the line (M2) having a G to A mutation at position 299 out of the above lines, and their base sequences were determined. As a result, 8 individuals having a target mutation in the form of homozygous mutation (eIF(iso)4E_T-type mutant homozygotes) were obtained.

(Line Breeding and Selection of eIF(Iso)4E_ST Double Homozygous Mutant)

The eIF(iso)4E_S-type mutant homozygote and the eIF(iso)4E_T-type mutant homozygote were crossed with each other. The crossing produced an F1 line in which a wild-type gene (with no mutation) and a mutant-type gene were held in a heterozygous manner both in a locus of an S-type eIF(iso)4E and in a locus of a T-type eIF(iso)4E. The individuals in the F1 line were self-pollinated (selfed) to obtain individuals in an F2 line. Theoretically, the probability of the individuals in the F2 line with both the S-type mutation and the T-type mutation as homozygous mutations is 1/16. F2 seeds were sown, and DNAs were extracted from 700 individuals.

DNA extraction was performed as follows. A tobacco leaf sample (1 cm×1 cm) was put in a 2 mL tube, 400 μL of extraction solution (composition: 200 mM Tris-HCl (pH7.5), 250 mM NaCl, 25 mM EDTA, 0.5% SDS) and 200 μL of Protein Precipitation Solution (manufactured by QIAGEN Inc.) were added to the tube. Thereafter, the tobacco leaf sample was crushed in the presence of metal cones. Subsequently, the tube was centrifuged at 13000 rpm for 10 minutes. To another 1.5 mL tube, 300 μL of supernatant was transferred, and 800 μL of 100% ethanol was added. A mixture solution was mixed by inversion. After centrifugation at 15000 rpm for 10 minutes, a supernatant was completely removed. After a pellet was confirmed to be dry, 50 μL of TE (10 mM Tris-HCl (pH7.5), 1 mM EDTA) was added.

As a DNA marker using PCR, allele specific primer (ASP) markers were designed. The ASP marker is a marker that utilizes a feature such that, with a primer designed to have a single nucleotide polymorphism (SNP) located at a 3' end side of a primer sequence, PCR products are obtained from only a sample having a specific polymorphism, and PCR products cannot be obtained from the other samples due to mismatches. The prepared primers are as shown in Table 5.

Nia2 gene (control, Literature: Vincentz and Caboche (1991) Constitutive expression of nitrate reductase allows normal growth and development of *Nicotiana plumbaginifolia* plants. EMBO J. 10: 1027-1035.). Next, another primer mix was prepared for detecting a mutant-type (Mut) eIF(iso)4E gene. The primer mix was composed of 10 μM each of primers F and R of eIF(iso)4E_S_Mut, 10 μM each of primers F and R of eIF(iso)4E_T_Mut, and 1 μM each of primers F and R of Nia2 gene (control). These primer mixes were provided for PCR for detection of a wild-type (WT) eIF(iso)4E gene and for PCR for detection of a mutant-type (Mut) eIF(iso)4E gene, respectively. The conditions for the PCR were as follows. A mixture of 1 μL of DNA solution adjusted to be 5 ng/μL, 1 μL of primer mix for WT or Mut detection, 3 μL of sterile water, and 5 μL of Multiplex PCR 2× Master Mix (QIAGEN Inc.) was used in the PCR as a 10 μL of system. The PCR was performed under the following conditions: 95° C. for 15 minutes and 40 cycles of 94° C. for 30 seconds, 59° C. for 90 seconds, and 72° C. for 1 minute, followed by 72° C. for 10 minutes. PCR products were electrophoresed by using QIAxcel (Qiagen Inc.), and detection was performed.

Figure 4:
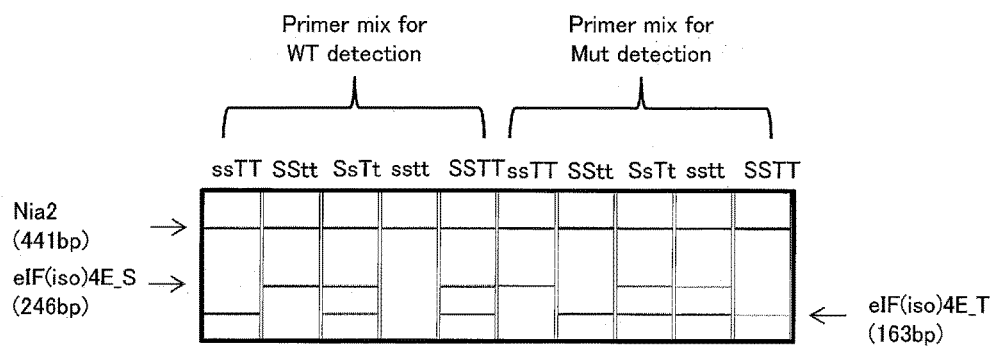
FIG. 4 is a diagram showing the result of mutant detection performed using an ASP marker in Example of the present invention.
Figure 5:
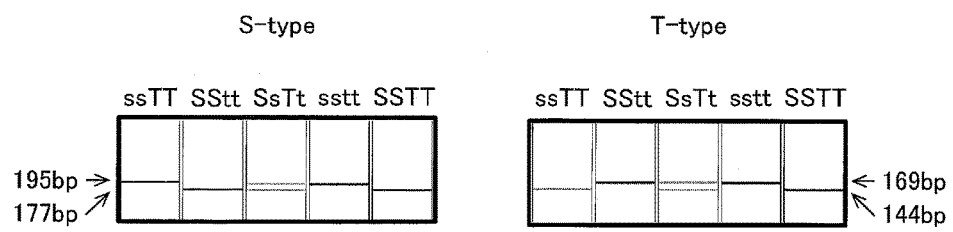
FIG. 5 is a diagram showing the result of mutant detection performed using a dCAPS marker in Example of the present invention.

Some of the results are shown in FIG. 4. First, amplification of the Nia2 gene, which was used as a control, was confirmed (441 bp of band in an upper part of FIG. 4). With the primer mix for wild type (WT) detection, both in an S-type eIF(iso)4E gene and in a T-type eIF(iso)4E gene, WT is detected. With the primer mix for mutant type (Mut) detection, both in an S-type eIF(iso)4E gene and in a T-type eIF(iso)4E gene, Mut is detected. Therefore, the type of mutation was determined based on the results of both the WT detection and the Mut detection. In one example, in a case where amplified products were not found by the primers for eIF(iso)4E_S_WT, amplified products were detected by the primers for eIF(iso)4E_T_WT, amplified products were detected by the primers for eIF(iso)4E_S_Mut, and amplified products were not detected by the primers for eIF(iso)4E_T_Mut, a sample of interest was determined to be of a genotype ssTT, in which only S-type eIF(iso)4E genes are mutant genes. In another example, in a case where

TABLE 5

Table 5: Primers for ASP marker used for tobacco mutant selection

| Target site | Primer | | Sequence (5'-3') | SEQ ID NO: |
|---|---|---|---|---|
| eIF(iso)4E_S_WT | Forward | (F) | CCATACCCTGATTCTCTTCC | SEQ ID NO: 37 |
| | Reverse | (R) | AACTTCCCCAAGCGGCTCaTaGT* | SEQ ID NO: 38 |
| eIF(iso)4E_S_Mut | Forward | (F) | CCATACCCTGATTCTCTTCC | SEQ ID NO: 37 |
| | Reverse | (R) | AACTTCCCCAAGCGGCTCaTaAT* | SEQ ID NO: 39 |
| eIF(iso)4E_T_WT | Forward | (F) | GCCTCAATCGACACAAAAGGGAGAG | SEQ ID NO: 40 |
| | Reverse | (R) | TTGCTTCGGCTTATCGAtCC* | SEQ ID NO: 41 |
| eIF(iso)4E_T_Mut | Forward | (F) | GCCTCAATCGACACAAAAGGGAGAG | SEQ ID NO: 40 |
| | Reverse | (R) | GGCTTATCGAtTC* | SEQ ID NO: 42 |
| Nia2 (Control) | Forward | (F) | CCGAGTAAAGATGAATGTGTGC | SEQ ID NO: 43 |
| | Reverse | (R) | TTGCCAGGAGAGTCAGAGGT | SEQ ID NO: 44 |

*A lower-case letter indicates a base which causes a mismatch with target template DNA.

First, a primer mix was prepared for detecting a wild-type (WT) eIF(iso)4E gene in which no mutation occurs. The primer mix was composed of 10 μM each of primers F and R of eIF(iso)4E_S_WT, 10 μM each of primers F and R of eIF(iso)4E_T_WT, and 1 μM each of primers F and R of PCR products were not detected by the two pair of primers for WT detection, and PCR products were detected by the two pair of primers for Mut detection, a sample of interest was determined to be of a genotype sstt, in which both S-type eIF(iso)4E genes and T-type eIF(iso)4E genes are mutant genes. Note that a faint band that appears in the rightmost lane (for Mut detection, SSTT) in FIG. 4 was considered to be an artifact.

In this manner, the eIF(iso)4E_ST double homozygous mutant (individual having homozygous mutations both in S-type eIF(iso)4E genes and in T-type eIF(iso)4E genes; genotype: sstt), and an eIF(iso)4E_wild type individual (individual having wild-type S-type eIF(iso)4E genes and wild-type T-type eIF(iso)4E genes; genotype: SSTT) as a control were obtained from the F2 line by polymorphism analysis using DNA markers. DNA sequences of PCR products from the selected individuals were decoded to confirm mutations. As a result, it was verified that the result of the DNA marker selection was accurate.

(Reproduction of eIF(Iso)4E_S-Type Mutant and eIF(Iso)4E_T-Type Mutant)

The aforementioned eIF(iso)4E_S-type mutant (with homozygously mutated S-type eIF(iso)4E genes; genotype: ssTT) and eIF(iso)4E_T-type mutant (with homozygously mutated T-type eIF(iso)4E genes; genotype: SStt) were cultivated to obtain selfed progenies for reproduction of seeds. Some of the seeds obtained from the progenies were sown and cultivated. In the same manner as in the above case, DNAs were extracted to perform polymorphism analysis using a DNA marker. As a result, the seeds were confirmed to have a homozygous mutation in the S-type eIF(iso)4E gene or in the T-type eIF(iso)4E gene.

Those seeds in which the mutations had been confirmed were deposited in the National Institute of Technology and Evaluation International Patent Organism Depositary (#120, 2-5-8 Kazusakamatari, Kisarazu-shi, Chiba 292-0818, Japan). The seeds of the eIF(iso)4E_S-type mutant were deposited as NtS1, while the seeds of the eIF(iso)4E_T-type mutant were deposited as NtT1. Their respective accession numbers are FERM BP-22284 (accession date: Feb. 25, 2015) and FERM BP-22285 (accession date: Feb. 25, 2015).

(Development of dCAPS Marker for Identifying Genotype of a Mutant)

dCAPS markers were developed as a DNA marker for detecting a polymorphism of each eIF (iso) 4E gene with a higher degree of accuracy. In a case where a polymorphism is present in a restriction enzyme recognition sequence, the polymorphism can be identified by detecting differences in fragment length between fragments obtained by treatment with a restriction enzyme. This is referred to as CAPS marker or PCR-RFLP marker. In the case of the above-mentioned mutations that occurred in the S-type eIF(iso)4E gene and in the T-type eIF(iso)4E gene (the C to T mutation at position 330 in SEQ ID NO: 7 and the G to A mutation at position 299 in SEQ ID NO: 8, respectively), any restriction enzyme recognition sequence was not contained in sequences around a single nucleotide polymorphism (SNP). Thus, primers for use in PCR were designed such that a restriction enzyme site was artificially introduced in the vicinity of the SNP. In the case of the above-mentioned mutations, a mutant type gene required substitutions of two bases to contain a restriction site (in the case of an S-type eIF(iso)4E gene, "CATG" as Nla III site, and in the case of a T-type eIF(iso)4E gene, "GATC" as Mbo I site), whereas a wild type gene required a substitution of a single base to contain a restriction site. Accordingly, Example 2 introduced a substitution of a single base to prepare a dCAPS marker such that a restriction enzyme cuts PCR products obtained from a wild type gene, but does not cut PCR products obtained from a mutant type gene. In this case, a difference in fragment length is detected as a difference in length of a primer. The primers thus prepared are as shown in Table 6.

Take SEQ ID NO: 46 as an example. In a case where a template DNA of a wild type is used, bases "CaT" at a 3' end side are followed by "G", which leads to a Nla III site (CATG). On the other hand, in a case where a template DNA of a mutant is used, bases "CaT" at a 3' end side are followed by "A", which does not lead to a restriction site. Take SEQ ID NO: 48 as another example. In a case where a template DNA of a wild type is used, bases "GAt" at a 3' end side are followed by "C", which leads to a Mbo I site (GATC). On the other hand, in a case where a template DNA of a mutant is used, bases "GAt" at a 3' end side are followed by "T", which does not lead to a restriction site.

Assume that a mismatch is provided in the vicinity of a 3' end of a primer. In this case, when PCR is performed with DNA polymerase having a proofreading activity, the mismatch can be corrected by the DNA polymerase. Thus, cutting with a restriction enzyme may end in failure. In fact, no polymorphism was detected in products obtained by performing PCR, using a genomic DNA as a template, with Tks Gflex™ DNA Polymerase (manufactured by Takara-Bio Inc.) having proofreading activity, and treating PCR products with a restriction enzyme. Meanwhile, using a genomic DNA as a template, PCR was performed with TaKaRa Taq™ (Takara-Bio Inc.) free from proofreading activity. In this case, an adequate amplification was not attained. As such, nested PCR was performed such that 1st PCR with Tks Gflex™ DNA Polymerase (having a proofreading function) was performed to specifically amplify a region containing an SNP region and its surroundings, and 2nd PCR with TaKaRa Taq™ (free from a proofreading function) was then performed to produce a restriction enzyme recognition site.

TABLE 6

Table 6: Primers for dCAPS marker used for tobacco mutant selection

| Target site | Primer | Sequence (5'-3') | SEQ ID NO: |
|---|---|---|---|
| eIF(iso)4E_S_1$^{st}$PCR | Forward (F) | GGCCTAAACGTTGTAAGACAA | SEQ ID NO: 25 |
|  | Reverse (R) | TGCTTAGTTAAATGCTACAGGG | SEQ ID NO: 26 |
| eIF(iso)4E_S_2$^{nd}$PCR | Forward (F) | AAATCGACACAAAGGGAGGAG | SEQ ID NO: 45 |
|  | Reverse (R) | AACTTCCCCAAGCGGCTCCaT* | SEQ ID NO: 46 |
| eIF(iso)4E_T_1$^{st}$PCR | Forward (F) | GACCTGAACATTGCAAGATGA | SEQ ID NO: 31 |
|  | Reverse (R) | GGCTTACTTGAATGCTACAAGG | SEQ ID NO: 32 |
| eIF(iso)4E_T_2$^{nd}$PCR | Forward (F) | GCCTCAATCGACACAAAAGGGAGAG | SEQ ID NO: 47 |
|  | Reverse (R) | AGCGCCTTGCTTCGGCTTATCGAt* | SEQ ID NO: 48 |

*A lower-case letter indicates a base which was inserted to create a restriction enzyme site in a wild type and causes a mismatch with target template DNA.

Primers for use in 2nd PCR were designed to include mismatches so that a product amplified by the eIF(iso)4E_S primers can be cut with a restriction enzyme Nla III only in a case where a wild type SNP is contained in the product, and so that a product amplified by the eIF(iso)4E_T primers can be cut with a restriction enzyme Mbo I only in a case where a wild type SNP is contained in the product.

First, 1st PCR was performed with Tks Gflex™ DNA Polymerase. As a template, approximately 5 ng of genomic DNA was used. The primers were so adjusted as to be in concentration of 1 µM. As a buffer, a buffer accompanying the enzyme was used. PCR was performed under the following conditions: 94° C. for 1 minute and 30 cycles of 98° C. for 10 seconds, 60° C. for 15 seconds, and 68° C. for 30 seconds, followed by 68° C. for 90 seconds. Thereafter, products obtained by 1st PCR were diluted by a 100-fold dilution factor. Using 1 µL of dilute as a template, 2nd PCR was performed with TaKaRa Taq™. As in 1st PCR, the primers were so adjusted as to be in concentration of 1 µM, and the buffer accompanying the enzyme was used. PCR was performed under the following conditions: 94° C. for 2 minutes and 40 cycles of 94° C. for 30 seconds, 52° C. for 30 seconds, and 72° C. for 30 seconds, followed by 72° C. for 90 seconds. Products obtained by 2nd PCR of eIF(iso) 4E_S were treated with Nla III (New England Biolabs Inc.). Products obtained by 2nd PCR of eIF(iso)4E_T were treated with Mbo I (Takara-Bio, Inc.).

The results are shown in Table 5. As for a sample such that products amplified by the eIF(iso)4E_S primers were not cut when they were treated with the restriction enzyme, the genotype of the sample was determined to be "ss". Meanwhile, as for a sample such that products amplified by the eIF(iso)4E_T primers were not cut when they were treated with the restriction enzyme, the genotype of the sample was determined to be "tt". For example, as for a sample such that products amplified by the eIF(iso)4E_S primers were not cut with the restriction enzyme, and products amplified by the eIF(iso)4E_T primers were cut with the restriction enzyme, the genotype of the sample was determined to be "ssTT". As for a sample such that products amplified by the eIF(iso) 4E_S primers were cut with the restriction enzyme, and products amplified by the eIF(iso)4E_T primers were not cut with the restriction enzyme, the genotype of the sample was determined to be "SStt". As for a sample such that products amplified by the eIF(iso)4E_S primers were cut with the restriction enzyme, and products amplified by the eIF(iso) 4E_T primers were cut with the restriction enzyme, the genotype of the sample was determined to be "SSTT". As for a sample such that products amplified by the eIF(iso) 4E_S primers were not cut with the restriction enzyme, and products amplified by the eIF(iso)4E_T primers were not cut with the restriction enzyme, the genotype of the sample was determined to be "sstt". As for a sample such that some of products amplified by the eIF(iso)4E_S primers was cut with the restriction enzyme while the other was not cut, and some of products amplified by the eIF(iso)4E_T primers was cut with the restriction enzyme while the other was not cut, the genotype of the sample was determined to be "SsTt". In this manner, determination of the genotype was easily performed. Thus, as in the case with the above ASP marker, the dCAPS marker in Example 2 was confirmed to be effectively used for identification of the genotype of an individual in which a mutation has occurred in an eIF(iso)4E gene of tobacco.

(Analysis of Expression of eIF(Iso)4E Tobacco Mutant)

Transcription analysis of eIF(iso)4E gene was performed on various eIF(iso)4E tobacco mutants. From each of the followings: the eIF(iso)4E_S-type mutant (ssTT), the eIF (iso)4E_T-type mutant (SStt), the eIF(iso)4E_ST double homozygous mutant (sstt), and the eIF(iso)4E_wild type line (SSTT), all of which were selected by a DNA marker, RNA was extracted as in the aforementioned case, and cDNA was synthesized, and a quantitative PCR was performed. As a set of primers and a probe, SEQ ID NO: 19, SEQ ID NO: 20, and SEQ ID NO: 21 shown in Table 2 were used for an S-type eIF(iso)4E gene. For a T-type eIF(iso)4E gene, SEQ ID NO: 49, SEQ ID NO: 50, and SEQ ID NO: 51 shown in Table 6 were newly designed and provided in an experiment.

TABLE 7

Table 7: A set of primers and a probe for quantitative PCR of T-type eIF(iso)4E gene

| Target gene | Primers/ Probe | Sequence (5'-3') | SEQ ID NO: |
|---|---|---|---|
| eIF(iso) 4E-T | Forward | GCCGGATACGGTGGAGAAG | SEQ ID NO: 49 |
| | Reverse | CCAAACAGCGCCTTGCTT | SEQ ID NO: 50 |
| | Probe | ATGGACATTCMGTTCGAT | SEQ ID NO: 51 |

Figure 6:
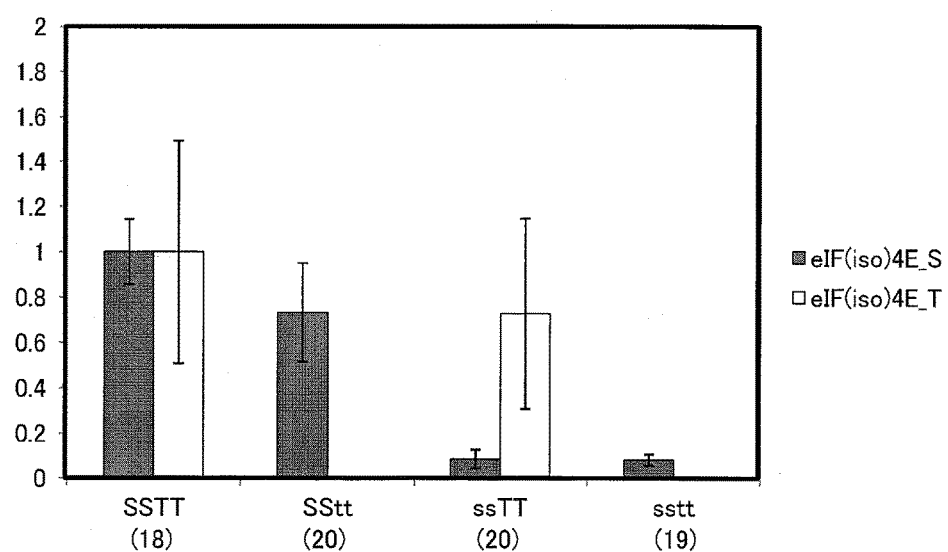
FIG. 6 is a graph showing the result of eIF(iso)4E gene expression analysis by quantitative PCR (expression levels relative to an average value of the amount of transcripts of the line SSTT) in Example of the present invention, wherein error bars represent standard deviations.

Measurement results are shown in FIG. 6. FIG. 6 shows respective expression levels of eIF(iso)4E genes measured relative to an average value of the amount of transcripts of the line of the genotype SSTT. A horizontal axis represents a genotype of each mutant, and a numerical value in parentheses indicates the number of analyzed individuals. A vertical axis represents a relative average value of the amounts of transcripts in a line having each genotype, and a bar represents a standard deviation. As for the line of the genotype SStt, the amount of transcripts of S-type eIF(iso) 4E gene was 73% of the control, but transcripts of T-type eIF(iso)4E gene were not detected at all. In contrast, as for the line of the genotype ssTT, the amount of transcripts of T-type eIF(iso)4E gene was 73% of the control, but the amount of transcripts of S-type eIF(iso)4E gene was reduced to 8.0% of the control. Further, as for the line of the genotype sstt, transcripts of T-type eIF(iso)4E genes were not detected at all, and the amount of transcripts of S-type eIF(iso)4E genes was reduced to 8.3% of the control. The above results proved that the line of the genotype SStt specifically suppressed expression of T-type eIF(iso)4E gene, that the line of the genotype ssTT specifically suppressed expression of S-type eIF(iso)4E gene, and the line of the genotype sstt suppressed expressions of S- and T-types of eIF(iso)4E genes.

Transcriptional suppression resulting from a nonsense mutation was attributed to nonsense-mediated mRNA decay (NMD) (Literature: Baker and Parker 2004, Current Opinion in Cell Biology 16: 293-299) was considered.

(Virus Inoculation Tests on eIF(Iso)4E Tobacco Mutants)

Individual plants two weeks after transplantation into a culture soil were inoculated with PVY-B (VAM-breading strain of Potato virus Y) or TBTV (Tobacco bushy top virus). Preparation of the viral inoculum and inoculation of the virus into tobacco were performed in the same manner as in Example 1. After the inoculation, the individuals were cultivated in a greenhouse, and their disease symptoms were observed at appropriate times. The results of virus inoculation tests on the eIF(iso)4E function-lacking tobacco mutants are shown in Tables 8 and 9.

In disease symptom evaluations performed at the 10th day after the PVY-B inoculation, the disease symptom was not observed in the individuals in the eIF(iso)4E_ST double homozygous mutant line (line having homozygous mutations both in S-type eIF(iso)4E genes and in T-type eIF(iso)4E genes; genotype: sstt). On the other hand, in a disease symptom evaluation performed on the 8th day after the PVY-B inoculation, the disease symptom was observed in all of the individual plants in the eIF(iso)4E_wild type line (line having wild-type S-type eIF(iso)4E genes and wild-type T-type eIF(iso)4E genes; genotype: SSTT) and in the cultivar TN90. This proved that the tobacco mutant lacking both the S-type eIF(iso)4E function and the T-type eIF(iso)4E function had resistance to PVY-B. Further, the disease symptom evaluations performed at the 10th day after the PVY-B inoculation showed that the line lacking only the T-type eIF(iso)4E function (eIF(iso)4E_T-type mutant line with homozygously mutated T-type eIF(iso)4E genes; genotype: SStt) greatly suppressed the disease symptom, as compared to the eIF(iso)4E_wild type line, the cultivar TN90, and the line lacking only the S-type eIF(iso)4E function (eIF(iso)4E_S-type mutant line with homozygously mutated S-type eIF(iso)4E genes; genotype: ssTT). From these results, PVY-B was presumed to mainly utilize T-type eIF(iso)4E for expressing its disease symptom caused by replication or cell-to-cell movement of PVY-B, and it was considered that suppression of T-type eIF(iso)4E expression enables suppression of the disease symptom caused by PVY-B.

In disease symptom evaluations performed at the 12th day after the TBTV inoculation, the disease symptom was not observed in the individual plants in the eIF(iso)4E_ST double homozygous mutant line (sstt). On the other hand, in a disease symptom evaluation on the 10th day after the TBTV inoculation, the disease symptom was observed in more than half of the individual plants in the eIF(iso)4E_wild type line (SSTT) and in the cultivar TN90. This proved that the tobacco mutant lacking both the S-type eIF(iso)4E function and the T-type eIF(iso)4E function had resistance to TBTV. Further, the line lacking only the S-type eIF(iso)4E function (eIF(iso)4E_S-type mutant line; ssTT) greatly suppressed the disease symptom, as compared to the eIF(iso)4E_wild type line (SSTT), the cultivar TN90, and the line lacking only the T-type eIF(iso)4E function (eIF(iso)4E_T-type mutant line; SStt). From these results, TBTV was presumed to mainly utilize S-type eIF(iso)4E for expressing its disease symptom caused by replication or cell-to-cell movement of TBTV, and it was considered that suppression of S-type eIF(iso)4E expression enables suppression of the disease symptom caused by TBTV. Growth inhibition of the eIF(iso)4E function-suppressed tobacco was not observed at all.

The above results demonstrated that suppression of the function of the translation initiation factor eIF(iso)4E in tobacco imparts PVY-B resistance to tobacco, and further demonstrated that suppression of only the function of the T-type eIF(iso)4E in tobacco enables imparting PVY-B resistance to tobacco. Furthermore, the above results demonstrated that suppression of the function of the translation initiation factor eIF(iso)4E in tobacco imparts TBTV resistance to tobacco, and further demonstrated that suppression of only the function of the S-type eIF(iso)4E in tobacco enables imparting TBTV resistance to tobacco.

TABLE 8

Results of PVY-B inoculation tests on eIF(iso)4E function-lacking tobacco mutants

| Line (genotype) | Number of individuals showing disease symptom 7 days after inoculation/number of individuals under test | Number of individuals showing disease symptom 8 days after inoculation/number of individuals under test | Number of individuals showing disease symptom 10 days after inoculation/number of individuals under test |
|---|---|---|---|
| eIF(iso)4E_ST double homozygous mutant line (sstt) | 0/9 (0.0%) | 0/9 (0.0%) | 0/9 (0.0%) |
| eIF(iso)4E_T-type mutant line (SStt) | 0/10 (0.0%) | 1/10 (10.0%) | 3/10 (30.0%) |
| eIF(iso)4E_S-type mutant line (ssTT) | 10/10 (100.0%) | 10/10 (100.0%) | 10/10 (100.0%) |
| eIF(iso)4E_wild type line (SSTT) | 8/8 (100.0%) | 8/8 (100.0%) | 8/8 (100.0%) |
| TN90 (Control; cultivar) | 5/9 (55.6%) | 9/9 (100.0%) | 9/9 (100.0%) |

TABLE 9

Results of TBTV inoculation tests on eIF(iso)4E function-lacking tobacco mutants

| Line (genotype) | Number of individuals showing disease symptom 7 days after inoculation/number of individuals under test | Number of individuals showing disease symptom 10 days after inoculation/number of individuals under test | Number of individuals showing disease symptom 12 days after inoculation/number of individuals under test |
|---|---|---|---|
| eIF(iso)4E_ST double homozygous mutant line (sstt) | 0/10 (0.0%) | 0/10 (0.0%) | 0/10 (0.0%) |
| eIF(iso)4E_T-type mutant line (SStt) | 3/10 (30.0%) | 5/10 (50.0%) | 7/10 (70.0%) |
| eIF(iso)4E_S-type mutant line (ssTT) | 0/10 (0.0%) | 1/10 (10.0%) | 2/10 (20.0%) |

TABLE 9-continued

Results of TBTV inoculation tests on eIF(iso)4E function-lacking tobacco mutants

| Line (genotype) | Number of individuals showing disease symptom

-continued

```
agatggacat tctggttcga taagccgaag caaggcgctg tttgggcaag tgctcttcga    180
aaagcctata ctttcgaaac tgttgaggaa ttctggagtt tatatgatca gatattcaag    240
cccagcaagt tgactgctaa tgcggacttt catttgttca aagctgggat tgagcccaaa    300
tgggaagatc ctgagtgtgc caatggtggc aagtggactg tcacgagcag cagaaaggct    360
aatcttgaga ctatgtggct tgaaactctg atggcattgg tgggtgagca atttgatgaa    420
tcagaagaga tatgtggagt ggttgccagt gttcgtcgga gtcaggataa actttccttg    480
tggactagga ctgcctccaa tgaagcagct cagatgagca ttggtaggaa gtggaaggag    540
atcatcgatg ctgaaaaaat atcctatagt ttccatgatg actctaaaaa ggaaaggtca    600
gttaagagtc gatatactgt gtgaattccc ttattgtgtg ggattgacac cggtccctaa    660
gtttactgaa aattgtacga ttagcattag tttgcgcttg tctgctgcaa attttgattt    720
tcttgaaatt tattcgtact tgatatgtat ctttggatgt attgtgttaa agattttgtt    780
tgcttctttg ttacttgaaa aaaaa                                          805
```

```
<210> SEQ ID NO 3
<211> LENGTH: 200
<212> TYPE: PRT
<213> ORGANISM: Nicotiana tabacum

<400> SEQUENCE: 3

Met Ala Thr Glu Ala Pro Ile Glu Ala Thr Glu Val Pro Pro Ala Ser
1               5                   10                  15

Ala Thr Glu Thr Val Ala Lys Gln Pro His Lys Leu Glu Arg Arg Trp
            20                  25                  30

Thr Phe Trp Phe Asp Asn Gln Ser Lys Pro Lys Gln Gly Ala Ala Trp
        35                  40                  45

Gly Ser Ser Leu Arg Lys Ala Tyr Thr Phe Glu Thr Val Glu Glu Phe
    50                  55                  60

Trp Ser Leu Tyr Asp Gln Ile Phe Lys Pro Ser Lys Leu Thr Ala Asn
65                  70                  75                  80

Ala Asp Phe His Leu Phe Lys Ala Gly Ile Glu Pro Lys Trp Glu Asp
                85                  90                  95

Pro Glu Cys Ala Ser Gly Gly Lys Trp Thr Val Thr Ser Ser Arg Lys
            100                 105                 110

Ala Asn Leu Glu Thr Met Trp Leu Glu Thr Leu Met Ala Leu Val Gly
        115                 120                 125

Glu Gln Phe Asp Glu Ser Glu Glu Ile Cys Gly Val Val Ala Ser Val
    130                 135                 140

Arg Arg Ser Gln Asp Lys Leu Ser Leu Trp Thr Lys Thr Ala Ser Asn
145                 150                 155                 160

Glu Ala Ile Gln Met Ser Ile Gly Arg Lys Trp Lys Glu Ile Ile Asp
                165                 170                 175

Ala Glu Lys Ile Ser Tyr Ser Phe His Asp Asp Ser Lys Arg Glu Arg
            180                 185                 190

Ser Ala Lys Ser Arg Tyr Thr Val
        195                 200

<210> SEQ ID NO 4
<211> LENGTH: 195
<212> TYPE: PRT
<213> ORGANISM: Nicotiana tabacum

<400> SEQUENCE: 4
```

```
Met Ala Thr Glu Ala Pro Ile Glu Ala Thr Glu Val Leu Pro Ala Pro
1               5                   10                  15

Asp Thr Val Glu Lys Gln Pro His Lys Leu Glu Arg Arg Trp Thr Phe
            20                  25                  30

Trp Phe Asp Lys Pro Lys Gln Gly Ala Val Trp Ala Ser Ala Leu Arg
        35                  40                  45

Lys Ala Tyr Thr Phe Glu Thr Val Glu Glu Phe Trp Ser Leu Tyr Asp
50                  55                  60

Gln Ile Phe Lys Pro Ser Lys Leu Thr Ala Asn Ala Asp Phe His Leu
65                  70                  75                  80

Phe Lys Ala Gly Ile Glu Pro Lys Trp Glu Asp Pro Glu Cys Ala Asn
            85                  90                  95

Gly Gly Lys Trp Thr Val Thr Ser Ser Arg Lys Ala Asn Leu Glu Thr
            100                 105                 110

Met Trp Leu Glu Thr Leu Met Ala Leu Val Gly Glu Gln Phe Asp Glu
            115                 120                 125

Ser Glu Glu Ile Cys Gly Val Val Ala Ser Val Arg Arg Ser Gln Asp
            130                 135                 140

Lys Leu Ser Leu Trp Thr Arg Thr Ala Ser Asn Glu Ala Ala Gln Met
145                 150                 155                 160

Ser Ile Gly Arg Lys Trp Lys Glu Ile Ile Asp Ala Glu Lys Ile Ser
                165                 170                 175

Tyr Ser Phe His Asp Asp Ser Lys Lys Glu Arg Ser Val Lys Ser Arg
                180                 185                 190

Tyr Thr Val
        195

<210> SEQ ID NO 5
<211> LENGTH: 867
<212> TYPE: RNA
<213> ORGANISM: Nicotiana tabacum

<400> SEQUENCE: 5
uccauuacgc cucuccguuc gcuaaaaauc gacacaaagg gaggagagga uuuuuugagg         60
caaaaaucaa uggccacuga agcaccgaua gaggcgacgg agguuccgcc ggcgucagcg        120
acggagacgg uggcgaagca gccacauaag cuagagagga gauggacauu cugguucgau        180
aaucaaucua agccgaaaca aggagccgcu uggggaaguu ucuuucgaaa agcuuauacu        240
uucgaaacug uugaggaauu cuggaguuua uaugaucaga uauucaagcc cagcaaguug        300
acugcuaaug cggacuuuca uuuguucaaa gcugggauug agcccaaaug gaagauccu         360
gagugugcua guggugcaa guggacuguu acgagcagca gaaaggcuaa ucuugagacu        420
auggccuug aaacucugau ggcauugguc ggugagcagu uugaugaguc agaggagaua        480
ugggagugg uugccagugu acgucggagu caggauaaac uuccuuaug acuaagacu         540
gccuccaaug aagcaauuca gaugagcauu gguaggaagu ggaaggagau cauugaugcu        600
gaaaaauau ccuauaguuu ccaugaugac ucuaaaaggg aaaggucagc uaagagucga        660
uauacugugu gaauuccuuu auugugugg auugacacug gucccuagau uuccaauac         720
ugaaaauugu acgauuagca caguuuugcg cuugucugcu gcaaaauuuu gauuucuuu        780
uuaaauuuau ucgcacuuga uauggaucuu uggauguauu guguuaaaga uuuguuugg        840
uucuguguua aaaaaaaaaa aaaaaaa                                            867

<210> SEQ ID NO 6
```

<211> LENGTH: 805
<212> TYPE: RNA
<213> ORGANISM: Nicotiana tabacum

<400> SEQUENCE: 6

```
gacacaaaag ggagaggauu uuuugaggca aaaucaaugg ccacugaagc accgauagag    60
gcgacggagg uucugccggc gccggauacg guggagaagc agccgcauaa gcuagagagg   120
agauggacau ucugguucga uaagccgaag caaggcgcug uuugggcaag ugcucuucga   180
aaagccuaua cuuucgaaac uguugaggaa uucuggaguu uauaugauca gauauucaag   240
cccagcaagu ugacugcuaa ugcggacuuu cauuuguuca aagcugggau ugagcccaaa   300
ugggaagauc cugagugugc caaugguggc aaguggacug ucacgagcag cagaaaggcu   360
aaucuugaga cuauguggcu ugaaacucug auggcauugg ugggugagca auuugaugaa   420
ucagaagaga uauguggagu gguugccagu guucgucgga gucaggauaa acuuuccuug   480
uggacuagga cugccuccaa ugaagcagcu cagaugagca uuguaggaa gugguaggag    540
aucaucgaug cugaaaaaau auccuauagu uuccaugaug acucuaaaaa ggaaagguca   600
guuaagaguc gauauacugu gugaauuccc uauugugug ggauugacac cggucccuaa    660
guuuacugaa aauuguacga uuagcauuag uuugcgcuug ucugcugcaa auuugauuu    720
ucuugaaauu uauucguacu ugauauguau cuuuggaugu auugcguuaa agauuuuguu   780
ugcuucuuug uuacuugaaa aaaaa                                         805
```

<210> SEQ ID NO 7
<211> LENGTH: 5140
<212> TYPE: DNA
<213> ORGANISM: Nicotiana tabacum
<220> FEATURE:
<221> NAME/KEY: misc_feature
<222> LOCATION: (4151)..(4151)
<223> OTHER INFORMATION: n is a, c, g, or t

<400> SEQUENCE: 7

```
cacccgcggt tggataccg gcccagtcta tcaatatggg cctaaacgtt gtaagacaag    60
tcccactaat atcaatcaac tgggctacca taaataattc cagctccata ccctgattct   120
cttccaacaa ttccattacg cctctccgtt cgctaaaaat cgacacaaag ggaggagagg   180
attttttgag gcaaaaatca atggccactg aagcaccgat agaggcgacg gaggttccgc   240
cggcgtcagc gacggagacg gtggcgaagc agccacataa gctagagagg atgggacat   300
tctggttcga taatcaatct aagccgaaac aaggagccgc ttggggaagt tctcttcgaa   360
aagcttatac tttcgaaact gttgaggaat tctggaggta tacaaaaaat acaaaacacg   420
agatctcttt tagattcttc tggttatatt ttttttgccc taatttagat tttttaatga   480
aatttttatca attgttttat gaattgggta atagcactt tgattcataa gttattgaga    540
aattctgatt tgttccctg tagcatttaa ctaagcatat ttaacctttt attcattaaa    600
atgtgtgttt tttggtccca ttacatagga aatatgttt acatttagat tagttttaga   660
actatattac ccttaaatat gaagtagtag tacaaattta acataacata tgggtactta   720
aatgatttaa aagttaatag ttcgttaaag tgggtagatt cacaaataga aggatgaaaa   780
gtgcacattt taattaattc aagtttaagt atgcataaac agatagcaca aggactataa   840
ctagaatatt tcaacattta agggtcaaaa agaacactct tccgtcctta attaattaag   900
atgctttcat gttgcaatgt tatgttgatg taagagtata tgaatatgtt accttcacaa   960
agagagagca catgtcttgg acctactttg tgctggaaac atattaaaaa ttatactttc  1020
```

```
tactacctgc tcgctcatat gaaactctgt tttgggagtt cgaaaaaata ttcaccatta    1080
cgttaattat ggagtattat ttatggaaaa gttccattaa gaatattgtc ctatgcatct    1140
tttgcaattt tcaagaatct aagtgcacct aagggggtgg gctagtggtc aatgaagtac    1200
gagaagaacc ttgagatctc aggttcaagt tccagcggag cgaaaaaata gtaggtgatt    1260
tcttccaatt tgcctaagcc ttggtaggca gaatacccga taccaggtag caggtacacg    1320
gcagaagccg gacatcacgt cataaaaaaa tcaagaattt gaattattta acaatccaaa    1380
gcttgtgata tgttctctgt acacctaagt ttttaggtat caatttagta ttttctttaa    1440
ccaccactaa tataattact atacagtcaa gcattgtgct ataaaaccaa acagtgccat    1500
ttttatctta aatttcataa ttttccatgt aatgaattta ctgctgcaat ttatccatag    1560
tttggatgtt gtgtggcttt attttaattc attaatgaga tattactgtt tagaaagtgt    1620
aatagttcca ctatgtggga ttatactggg tttgttgttg taaagtataa tagttggata    1680
gaagctgctt ttaaatgtca attgaagtgt tagatctttc tcttttcagt ttatatgatc    1740
agatattcaa gcccagcaag ttgactgcta atgcggactt tcatttgttc aaagctggga    1800
ttgagcccaa atgggaagat cctgagtgtg ctagtggtgg caagtggact gttacgagca    1860
gcagaaaggc taatcttgag actatgtggc ttgaaactgt aataaaatct tctcttttact   1920 tttcttggtt tctgttcagt aggcaggatg tcatgaaagc attatgttga ttagtttcta    1980
gttaaagatg ctcacatgtt gtttgctcga tggaattctt ttgaatagct gatggcattg    2040
gtcggtgagc agtttgatga gtcagaggag atatgtggag tggttgccag tgtacgtcgg    2100
agtcaggata aactttcctt atggactaag actgcctcca atgaagcaat tcaggttatt    2160
ggaattctca tgatgtagaa tagttactga actgaaaact gtgttatgtt ttaccctata    2220
tcataaatct gatatgaaat attatttaaa aaagaatata ccagaatatg atcttttttct   2280 taatgatgat gatatggccc atcttcccett ctaaaaaagg agctatctcc aattcttttt    2340
taaatgctga aaaggagag cgtatttatt tgagcactga attttgagaa caagggaagc     2400
atgcccttcc ccgttgtgac ccatggatgg aacactagat ctagttatta aatatcggtt    2460
aaaaccatca catgccttag ctaatcagtg gctgaaacta gtatttcttg gtagggaagt    2520
ccttgatatt tcctttaact tgtctctaac cggagttggc agatatgatg ttgttttttgt   2580 aatggtatga cctctaccat gtatttgttt tgaattttttt cttttgataa agtaaataat    2640
tttcttagtg atggggtgac cccgtataca agcctatacc aaaaagtgga gaacctacaa    2700
caaaatatgg ttgtcagtga aagaaaccaa tcatttatac acataaagac ctcatgggta    2760
caccaaaaag ctagaaacga gaggtcgttt tgcaattttt cgaaagcatt atcaacctct    2820
tcaaatactc tcatgttcct ctcttttccat agaacccaca taatggctga tggggaaaca    2880
tcccatgccc tcggtcttct cttcctcctg aaggcccaag tatgcaacgc ctctttcatt    2940
gtgcacgcat cacgcattat attcgaaacc aatttaggac caccgaccgc aactgtccag    3000
ccacatgaca acgcaacaag agatggtttt acacctttgc ccgcacaact gtacaagatg    3060
caacaactaa ccatttgttc ttattatggg ccttttgttg ccgttttgca ttaggccttc    3120
gctaaaaaca ctttgacccct ggctcatatc ccttgaactg atctatggac atataggcat    3180
ctgaatgtgc ttcatttttca tcttctaaag tacccttgtg cttgaaatcg aaatttgctg    3240
tgtggtgatg ttctatagat catagatggt aagaaattcc aaaagggtgt gaagtttgca    3300
aaggtgttcc ctagaagtct gtactcatca gcttctcatc taaacacagg aatgtggtta    3360
```

```
ttttgaaggg ttttacttgt cacgaagtgg atgcaggacc ccctccccccc caacacacac    3420
acacaacaca cccacccacc caatatgtct ttgtctccaa tttaattact taatgattat    3480
ggatttggga aaatggaaat atgctatctg gactttaagg ttgtactttg caatcttttta   3540
accttttccga cttgaactgt ataatgaatt gataatgtta caacgacctt ttaacatttg   3600
tttagaaaaa agggcaactc ggtgcatgat gcatcccgcg tttacacaag atccggtgaa    3660
gagccgcaac actagtgcgt gtgatggaaa caactttact gttgctccaa gactccattt    3720
cacctttta acatttttagt ttttttatt aagtttgggg gtgggaagag ggatttcaaa    3780
tggagacgtg tacactagaa agaactaact gaaaaaggac aaaggacaga taacctaata   3840
ctgtacctgg gacataaacc atttctctta tctttgcctt catgatttag tgattttttct  3900
cttttttctt ttccttgcga agttttcaca ttgcctctta aaatgtttaa aaactcgtca   3960
gggtggtaaa gtgcaatagg ccttttatac gaatgaaaag acaagaaac agctaaactg    4020
aaatagtatt tcttcaatct cacctaacag tttcattcat ttacagtgta cctaattctg   4080
gttggtcttg tttaatacac cttctcctgt gtgtaccact aatgcacttg ctaaggatga   4140
tttaattccc nacacacaca cccacccacc cacacaaaag atgctggaaa atgtatcttt   4200
ctccctctga atatgcagct tggagtttta gacacaagtt cttgtatttc attcgttaag   4260
cactattcca tattatacta aaagcttata ttagacatgt tcatcttaca gtattgcaag   4320
acacaaggtt caatttaaat tccattacat tgctccacta ggtttccttt tttgtttatt   4380
gttgtgtgac tgcatgtgtt ttcctgcttt taacacatgt aacatgtctg gatatcaaca   4440
atcttcattc ctaacctttg tttttttggca tgatgctaca cttgatgcat tgttttcctg  4500
cttttaacac atgtaacatg tctggatatc aacaatcttc attcctaacc tttgtttttt    4560
ggcatgatgc tacacttgat gcattgtttt cctgctttta acacatgtaa cacgtctgga   4620
tatcaacaat cttcattcct aacctttgtt ttttggcatg atgctacact tgatgcattg   4680
tggtttcgca attatatata accggttggt tttatgctgc agatgagcat tggtaggaag   4740
tggaaggaga tcattgatgc tgaaaaaata tcctatagtt tccatgtaac ttcccttgcc   4800
gcttgccatt attgcaaagt caagtgtctt ttatctttcc tcctgttaat ttcttttcct   4860
ctcgtaatca accaatcttt tggtcgttgc aggatgactc taaaagggaa aggtcagcta   4920
agagtcgata tactgtgtga attcctttat tgtgtgggat tgacactggt ccctagattt    4980
tccaatactg aaaattgtac gattagcaca gttttgcgct tgtctgctgc aaaattttga   5040
ttttctttt aaatttattc gcacttgata tggatctttg gatgtattgt gttaaagatt    5100
ttgtttggtt ctgtgttact tatctggagc ctgccccatg                          5140
```

<210> SEQ ID NO 8
<211> LENGTH: 3620
<212> TYPE: DNA
<213> ORGANISM: Nicotiana tabacum

<400> SEQUENCE: 8

```
acaacaaata cccgaggtag gattaccggc ccagtctgtc atcatatatg gacctgaaca     60
ttgcaagatg aggcccaata atagcaatca actgggccag tataaataaa attccagctc    120
cataacctga ttttcttccc aacaattcca ttacgcctca atcgacacaa aagggagagg    180
attttttgag gcaaaaatca atggccactg aagcaccgat agaggcgacg gaggttctgc    240
cggcgccgga tacggtggag aagcagccgc ataagctaga gaggagatgg acattctggt    300
tcgataagcc gaagcaaggc gctgtttggg caagtgctct tcgaaaagcc tatactttcg    360
```

-continued

```
aaactgttga ggaattctgg aggtatacaa aaaatacaaa acacgagatc acttctagat      420
tcttctggtt atatttattt gccctaattt agatctttaa tgaaattttg tcaattgttt      480
tattaattgg gataatagca cttttgatca tcagttattg ataaattcgg attttgttcc      540
ttgtagcatt caagtaagcc tatttaacct tgaattcatt aaaatgtgtg tttttggtcc      600
ctttacatag gaaatatgtt acatttagat tagttttaga actatattac cctaaaataa      660
gaagtgctag tacaaattta acataacata ggggtactta aatgatattg aaagttaaca      720
attcattaaa gttgtgtaga ttcacaaata gaaggatcaa aagtgcacat tttaattaat      780
tcaaggttaa gtatgcataa gcagatagca caaggactat aactagaata tgtcaatgtt      840
taagggacaa aaagcacaat cttccattct taattagtta agatgctttc atgctgcaag      900
gttctatgtt gatgtaagag tatatgaata tgttaccttc acaaaaagag aacatatatc      960
ttggaccttc tttgtgctgg aaaacatatt gaaaattata ctttctactt cctgcttata     1020
tgactctctg ttttgggact tcaggaattt ttcaccatta cactaattat tgagtattat     1080
tatggaaaag tttctttaag aatattgttc tatgcatctt ttgcaatttt caagaatcta     1140
actgcaacca atgggtgtag ctagtggtga atgaagtggg agaagaacct tgaggtctcg     1200
ggttcaaatt acagcggcag tgaaaagaat actagttccc atttgcaggt acccggcgga     1260
agctggatac cgcatcattt aaaaaaaacc aagaatttga attatttaac aatccaaagc     1320
ttgtgatatg ttctctataa aactaacttt ttagatatca atttagtgtt ttcttcaacc     1380
tccactaata taattactgt ccagtcaagc agtgtgctat aaaaccaaac cgtgcatttt     1440
tatcttaaat ttcataattt ccccagtaat ggattctacc gctgcaattt atccatactt     1500
gggatgttgt gtggctttat tttaattcat tgacgagata ttattattta gaaagtgtaa     1560
tagttggata gaagctgctt ttaaatgcca attgaagtgt tagatctttc tctttgcagt     1620
ttatatgatc agatattcaa gcccagcaag ttgactgcta atgcggactt tcatttgttc     1680
aaagctggga ttgagcccaa atgggaagat cctgagtgtg ccaatggtgg caagtggact     1740
gtcacgagca gcagaaaggc taatcttgag actatgtggc ttgaaactgt aataaagtct     1800
tccctttgct tctgttggtt tctgttcagt aggcaggatg tcatgaaagc attatgttga     1860
ttaatttctt gctaaagatg ctcacatatt gtttgctgga tggatttctt ttgggcagct     1920
gatggcattg gtgggtgagc aatttgatga atcagaagag atatgtggag tggttgccag     1980
tgttcgtcgg agtcaggata aactttcctt gtggactagg actgcctcca atgaagcagc     2040
tcaggttagt ttggaattct cgtggtgtca aatagtatct gaaattctga actaaaaact     2100
gtgttatttt ttcccctata tcctaaatct gatatgaaat attattaaaa aaaggatata     2160
ccagaatatt atcttttttct taatgatgat ctgtcccatc tccaattttt ttgtaaacgc     2220
tgaaaaagga gagcagcttt atttgagcac cgaattttga gaacaagaaa agaatgccct     2280
tccccattgt gacccatgga tggagcacta gatctgttat tcaatatata atttaaatat     2340
caattaaaac catcacatac cctagctaat cagtggctga aattattatt tttcttggca     2400
gggaatcctt gatatttcct ttcacttatt ctctaaccat aattggcagc tatgacgttt     2460
ttatttattg taatggtata gcttttctct ggcatttgtt cagttttctt gataaagtaa     2520
ataattttat tagtgatggg gagaccccgt atacaagcct ataccaaaaa gtggagaacc     2580
tacaacagaa tacggttctc catgaaagaa atacacatag gtacctcatg ggtacatcaa     2640
aaagaaacta gacaagagat tgttttgcaa ttttactaaa tcattatcaa ccccttcaaa     2700
```

| | |
|---|---|
| tgctctcatg ttcctttctt tccatataac ccacataatg gctgatgggg cgacatcaca | 2760 |
| tgccctcaat cttctgttcc tcctcctgaa ggcccaacta tgcaacacct ccttcattgt | 2820 |
| gcccgcatca cccattgtat tccaaaaaaa aagatgctgg aaaatgtatc ttttcccctc | 2880 |
| tgaacatgca gcttggagtt tgacataagt ttttgtattt cattctgtaa gcactgttcc | 2940 |
| agattatact aaaagcttat attagacatg ttcatcttac agtattgcaa tacacaaggt | 3000 |
| ttcaatttaa attcgattac atttctccac taggttccct tttttgttta ttgttgtctg | 3060 |
| actgcgtata tttcctgctt ttgaccatgt aacctgtctg gatatcaaca atcttcactc | 3120 |
| ttaacttttg ttttctggca tgttgctaca cttgatgctc catggttttg caatgatata | 3180 |
| tgactggttg gtttatgct gcagatgagc attggtagga agtggaagga gatcatcgat | 3240 |
| gctgaaaaaa tatcctatag tttccatgta acttctgttg ccccttacca ttattgcaaa | 3300 |
| atcaagtgtc ttttatcttt cctcctgtta atttttttct ttcttaatca acctttcttt | 3360 |
| tggttgttgc aggatgactc taaaaaggaa aggtcagtta agagtcgata tactgtgtga | 3420 |
| attcccttat tgtgtgggat tgacaccggt ccctaagttt actgaaaatt gtacgattag | 3480 |
| cattagtttg cgcttgtctg ctgcaaattt tgattttctt gaaatttatt cgtacttgat | 3540 |
| atgtatcttt ggatgtattg tgttaaagat tttgtttgct tctttgttac ttgtctaaag | 3600 |
| tgtgcctcat gtcttaattt | 3620 |

```
<210> SEQ ID NO 9
<211> LENGTH: 313
<212> TYPE: DNA
<213> ORGANISM: Artificial Sequence
<220> FEATURE:
<223> OTHER INFORMATION: RNAi trigger

<400> SEQUENCE: 9
```

| | |
|---|---|
| agaggcgacg gaggttccgc cggcgtcagc gacggagacg gtggcgaagc agccacataa | 60 |
| gctagagagg agatggacat tctggttcga taatcaatct aagccgaaac aaggagccgc | 120 |
| ttggggaagt tctcttcgaa aagcttatac tttcgaaact gttgaggaat tctggagttt | 180 |
| atatgatcag atattcaagc ccagcaagtt gactgctaat gcggactttc atttgttcaa | 240 |
| agctgggatt gagcccaaat gggaagatcc tgagtgtgct agtggtggca agtggactgt | 300 |
| tacgagcagc aga | 313 |

```
<210> SEQ ID NO 10
<211> LENGTH: 954
<212> TYPE: DNA
<213> ORGANISM: Nicotiana tabacum

<400> SEQUENCE: 10
```

| | |
|---|---|
| ggcacgagga acattgaac ttttcctacg aatacaaatt cggaatttct gtgagaagtt | 60 |
| acacattttc agttgaaacc catcaccaaa agtccaaaat cacaaatttc cagacgaaag | 120 |
| ctatagtgtt gagaacacca aaatggttga tgaagtagag aaaccggtgt cgttagagga | 180 |
| atcgaagact aatactcgtg aggtggaaga ggaaggagag atcgtggggg aatcagacga | 240 |
| tacgatgtcg tctttaggga acccaagcat ggcaatgaaa cacgcgctag aacattcatg | 300 |
| gacatttggg ttcgataacc catcagggaa atcaaaacag gctgcttggg gtagttccat | 360 |
| tcgaccaatt tacaccttct ccactgtcga agatttttgg agtgtgtaca acaatatcca | 420 |
| ccacccaagc aaattggctg tgggggcaga ctttcactgt tttaagaata aaattgagcc | 480 |
| aaagtgggag gatcctgtct gcgccaacgg aggaaagtgg acaatgagct tttcgagggg | 540 |

```
taaatctgat acctgctggc tgtatacgct gctggctatg attggagaac aatttgactg     600
cggagatgaa atttgtggag ctgttattaa tgttcgagtt agacaagaaa aaatagcttt     660
gtggaccagg aatgctgcca atgaaacagc tcaggtgagc attggtaaac agtggaagga     720
atttctggat tacaatgact cggttggctt tatatttcat gatgatgcaa agaagctaga     780
cagagctgcc aagaatcgtt attctgtgta gttctatcgt tacaatagga attgtgaacg     840
acacagttac tgagaagcag tcacctgtgg ctgcctgttt tgaccgctta cattggtatt     900
cacagttttc ataaggaaat ttgtttggtt ttgaaaaaaa aaaaaaaaaa aaaa           954

<210> SEQ ID NO 11
<211> LENGTH: 329
<212> TYPE: DNA
<213> ORGANISM: Artificial Sequence
<220> FEATURE:
<223> OTHER INFORMATION: RNAi trigger

<400> SEQUENCE: 11
cgaagactaa tactcgtgag gtggaagagg aaggagagat cgtgggggaa tcagacgata      60
cgatgtcgtc tttagggaac ccaagcatgg caatgaaaca cgcgctagaa cattcatgga     120
cattttggtt cgataaccca tcagggaaat caaaacaggc tgcttggggt agttccattc     180
gaccaattta caccttctcc actgtcgaag attttggag tgtgtacaac aatatccacc      240
acccaagcaa attggctgtg ggggcagact ttcactgttt taagaataaa attgagccaa     300
agtgggagga tcctgtctgc gccaacgga                                        329

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
caccgaagac taatactcgt gagg                                             24

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
tccgttggcg cagacagg                                                    18

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
caccagaggc gacggaggtt cc                                               22

<210> SEQ ID NO 15
<211> LENGTH: 20
<212> TYPE: DNA
<213> ORGANISM: Artificial Sequence
<220> FEATURE:
```

<223> OTHER INFORMATION: primer

<400> SEQUENCE: 15
tctgctgctc gtaacagtcc                                              20

<210> SEQ ID NO 16
<211> LENGTH: 28
<212> TYPE: DNA
<213> ORGANISM: Artificial Sequence
<220> FEATURE:
<223> OTHER INFORMATION: primer

<400> SEQUENCE: 16
cgagttagac aagaaaaaat agctttgt                                     28

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
atccagaaat tccttccayt gttt                                         24

<210> SEQ ID NO 18
<211> LENGTH: 26
<212> TYPE: DNA
<213> ORGANISM: Artificial Sequence
<220> FEATURE:
<223> OTHER INFORMATION: primer

<400> SEQUENCE: 18
accaggaatg ctgccaatga aacagc                                       26

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
gccactgaag caccgataga g                                            21

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
ttatcgaacc agaatgtcca tctc                                         24

<210> SEQ ID NO 21
<211> LENGTH: 18
<212> TYPE: DNA
<213> ORGANISM: Artificial Sequence
<220> FEATURE:
<223> OTHER INFORMATION: probe

<400> SEQUENCE: 21
tccgccggcg tcagcgac                                                18

```
<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
ctaagggtgc tgccagcttt                                               20

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
gtcaagcact ggagcatatc ca                                            22

<210> SEQ ID NO 24
<211> LENGTH: 26
<212> TYPE: DNA
<213> ORGANISM: Artificial Sequence
<220> FEATURE:
<223> OTHER INFORMATION: probe

<400> SEQUENCE: 24
atcatgaacc atccaggaca gattgg                                        26

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
ggcctaaacg ttgtaagaca a                                             21

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
tgcttagtta aatgctacag gg                                            22

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ttacgcctct ccgttcgcta                                               20

<210> SEQ ID NO 28
<211> LENGTH: 22
<212> TYPE: DNA
<213> ORGANISM: Artificial Sequence
<220> FEATURE:
<223> OTHER INFORMATION: primer
```

<400> SEQUENCE: 28
ctgggtttgt tgttgtaaag ta                                    22

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
cacagttttc agttcagtaa c                                     21

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
gatgggccat atcatcatca t                                     21

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
gacctgaaca ttgcaagatg a                                     21

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
ggcttacttg aatgctacaa gg                                    22

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
ttacgcctca atcgacacaa                                       20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
ccccagtaat ggattctacc                                       20

<210> SEQ ID NO 35
<211> LENGTH: 21

```
<212> TYPE: DNA
<213> ORGANISM: Artificial Sequence
<220> FEATURE:
<223> OTHER INFORMATION: primer

<400> SEQUENCE: 35
atcagattta ggatataggg g                                              21

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
cagatactat ttgacaccac                                                20

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
ccataccctg attctcttcc                                                20

<210> SEQ ID NO 38
<211> LENGTH: 23
<212> TYPE: DNA
<213> ORGANISM: Artificial Sequence
<220> FEATURE:
<223> OTHER INFORMATION: primer

<400> SEQUENCE: 38
aacttcccca agcggctcat agt                                            23

<210> SEQ ID NO 39
<211> LENGTH: 23
<212> TYPE: DNA
<213> ORGANISM: Artificial Sequence
<220> FEATURE:
<223> OTHER INFORMATION: primer

<400> SEQUENCE: 39
aacttcccca agcggctcat aat                                            23

<210> SEQ ID NO 40
<211> LENGTH: 25
<212> TYPE: DNA
<213> ORGANISM: Artificial Sequence
<220> FEATURE:
<223> OTHER INFORMATION: primer

<400> SEQUENCE: 40
gcctcaatcg acacaaaagg gagag                                          25

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
```
ttgcttcggc ttatcgatcc                                          20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
ttgcttcggc ttatcgattc                                          20

<210> SEQ ID NO 43
<211> LENGTH: 22
<212> TYPE: DNA
<213> ORGANISM: Artificial Sequence
<220> FEATURE:
<223> OTHER INFORMATION: primer

<400> SEQUENCE: 43
ccgagtaaag atgaatgtgt gc                                       22

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
ttgccaggag agtcagaggt                                          20

<210> SEQ ID NO 45
<211> LENGTH: 21
<212> TYPE: DNA
<213> ORGANISM: Artificial Sequence
<220> FEATURE:
<223> OTHER INFORMATION: primer

<400> SEQUENCE: 45
aaatcgacac aaagggagga g                                        21

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
aacttcccca agcggctcca t                                        21

<210> SEQ ID NO 47
<211> LENGTH: 25
<212> TYPE: DNA
<213> ORGANISM: Artificial Sequence
<220> FEATURE:
<223> OTHER INFORMATION: primer

<400> SEQUENCE: 47
gcctcaatcg acacaaaagg gagag                                    25

<210> SEQ ID NO 48
<211> LENGTH: 24
<212> TYPE: DNA
<213> ORGANISM: Artificial Sequence

```
<220> FEATURE:
<223> OTHER INFORMATION: primer

<400> SEQUENCE: 48
agcgccttgc ttcggcttat cgat                                              24

<210> SEQ ID NO 49
<211> LENGTH: 19
<212> TYPE: DNA
<213> ORGANISM: Artificial Sequence
<220> FEATURE:
<223> OTHER INFORMATION: primer

<400> SEQUENCE: 49
gccggatacg gtggagaag                                                    19

<210> SEQ ID NO 50
<211> LENGTH: 18
<212> TYPE: DNA
<213> ORGANISM: Artificial Sequence
<220> FEATURE:
<223> OTHER INFORMATION: primer

<400> SEQUENCE: 50
ccaaacagcg ccttgctt                                                     18

<210> SEQ ID NO 51
<211> LENGTH: 19
<212> TYPE: DNA
<213> ORGANISM: Artificial Sequence
<220> FEATURE:
<223> OTHER INFORMATION: Probe

<400> SEQUENCE: 51
atggacattc tggttcgat                                                    19
```

The invention claimed is:

1. A virus-resistant tobacco plant including a mutation in a translation initiation factor eIF(iso)4E gene, the mutation causing production of a translation initiation factor eIF(iso)4E protein with suppressed eIF(iso)4E gene function, the mutation being one or more mutations in (a) a translation initiation factor eIF(iso)4E gene encoding a translation initiation factor eIF(iso)4E protein consisting of an amino acid sequence represented by SEQ ID NO: 3 or SEQ ID NO: 4, (b) a translation initiation factor eIF(iso)4E gene encoding a functional translation initiation factor eIF(iso)4E protein having a sequence identity of 92% or higher with the amino acid sequence represented by SEQ ID NO: 3 or SEQ ID NO: 4, (c) a translation initiation factor eIF(iso)4E gene which causes production of mRNA consisting of a base sequence represented by SEQ ID NO: 5 or SEQ ID NO: 6, or (d) a translation initiation factor eIF(iso)4E gene encoding a functional translation initiation factor eIF(iso)4E protein which causes production of mRNA having a sequence identity of 92% or higher with the base sequence represented by SEQ ID NO: 5 or SEQ ID NO: 6, the virus being a strain of Potato virus Y, wherein said strain breaks virus resistance of Virgin A mutant of a tobacco plant, or the virus being Tobacco bushy top virus.

2. The virus-resistant tobacco plant according to claim 1, wherein the mutation is a nonsense mutation.

3. The virus-resistant tobacco plant according to claim 1, wherein the mutation is one or more of the following mutations (1) to (4): (1) C of codon CAA is substituted by T; (2) C of codon CGA is substituted by T; (3) C of codon CAG is substituted by T; and (4) G (either one or both of two Gs) of codon TGG is substituted by A, in (a) an exon of a translation initiation factor eIF(iso)4E gene which encodes a translation initiation factor eIF(iso)4E protein consisting of an amino acid sequence represented by SEQ ID NO: 3 or SEQ ID NO: 4, (b) an exon of a translation initiation factor eIF(iso)4E gene which encodes a functional translation initiation factor eIF(iso)4E protein having a sequence identity of 92% or higher with the amino acid sequence represented by SEQ ID NO: 3 or SEQ ID NO: 4, (c) an exon of a translation initiation factor eIF(iso)4E gene which causes production of mRNA consisting of a base sequence represented by SEQ ID NO: 5 or SEQ ID NO: 6, or (d) an exon of a translation initiation factor eIF(iso)4E gene which causes production of mRNA having a sequence identity of 92% or higher with the base sequence represented by SEQ ID NO: 5 or SEQ ID NO: 6 and encodes a functional translation initiation factor eIF(iso)4E protein.

4. The virus-resistant tobacco plant according to claim 1, wherein the mutation is one or more of the following mutations (1) to (27): (1) C to T substitution at position 270, (2) G to A substitution at position 295, (3) G to A substitution at position 296, (4) G to A substitution at position 304, (5) G to A substitution at position 305, (6) C to T substitution at position 315, (7) C to T substitution at position 330, (8) G to A substitution at position 343, (9) G to A substitution at position 344, (10) C to T substitution at position 357, (11) G to A substitution at position 394, (12) G to A substitution at position 395, (13) C to T substitution at position 1740, (14) G to A substitution at position 1813, (15) G to A substitution at position 1814, (16) G to A substitution at position 1846, (17) G to A substitution at position 1847, (18) G to A substitution at position 1888, (19) G to A substitution at position 1889, (20) C to T substitution at position 2050, (21) C to T substitution at position 2104, (22) G to A substitution at position 2123, (23) G to A substitution at position 2124, (24) C to T substitution at position 2152, (25) G to A substitution at position 4742, (26) G to A substitution at position 4743, and (27) C to T substitution at position 4926, in a translation initiation factor eIF(iso)4E gene consisting of a base sequence represented by SEQ ID NO: 7 in genomic DNA.

5. The virus-resistant tobacco plant according to claim 1, wherein the mutation is one or more of the following mutations (1) to (26): (1) C to T substitution at position 264, (2) G to A substitution at position 289, (3) G to A substitution at position 290, (4) G to A substitution at position 298, (5) G to A substitution at position 299, (6) C to T substitution at position 315, (7) G to A substitution at position 328, (8) G to A substitution at position 329, (9) C to T substitution at position 342, (10) G to A substitution at position 379, (11) G to A substitution at position 380, (12) C to T substitution at position 1630, (13) G to A substitution at position 1703, (14) G to A substitution at position 1704, (15) G to A substitution at position 1736, (16) G to A substitution at position 1737, (17) G to A substitution at position 1778, (18) G to A substitution at position 1779, (19) C to T substitution at position 1940, (20) C to T substitution at position 1994, (21) G to A substitution at position 2013, (22) G to A substitution at position 2014, (23) C to T substitution at position 2042, (24) G to A substitution at position 3224, (25) G to A substitution at position 3225, and (26) C to T substitution at position 3406, in a translation initiation factor eIF(iso)4E gene consisting of a base sequence represented by SEQ ID NO: 8 in genomic DNA.

6. The virus-resistant tobacco plant according to claim 1, wherein the mutation is one or more mutations in (a) a translation initiation factor eIF(iso)4E gene which encodes a translation initiation factor eIF(iso)4E protein consisting of an amino acid sequence represented by SEQ ID NO: 3, (b) a translation initiation factor eIF(iso)4E gene which encodes a functional translation initiation factor eIF(iso)4E protein having a sequence identity of 92% or higher with the amino acid sequence represented by SEQ ID NO: 3, (c) a translation initiation factor eIF(iso)4E gene which causes production of mRNA consisting of a base sequence represented by SEQ ID NO: 5, or (d) a translation initiation factor eIF(iso)4E gene which causes production of mRNA having a sequence identity of 92% or higher with the base sequence represented by SEQ ID NO: 5 and encodes a functional translation initiation factor eIF(iso)4E protein, and the virus is a Tobacco bushy top virus.

7. The virus-resistant tobacco plant according to claim 1, wherein the mutation is one or more mutations in (a) a translation initiation factor eIF(iso)4E gene which encodes a translation initiation factor eIF(iso)4E protein consisting of an amino acid sequence represented by SEQ ID NO: 4, (b) a translation initiation factor eIF(iso)4E gene which encodes a functional translation initiation factor eIF(iso)4E protein having a sequence identity of 92% or higher with the amino acid sequence represented by SEQ ID NO: 4, (c) a translation initiation factor eIF(iso)4E gene which causes production of mRNA consisting of a base sequence represented by SEQ ID NO: 6, or (d) a translation initiation factor eIF(iso)4E gene which causes production of mRNA having a sequence identity of 92% or higher with the base sequence represented by SEQ ID NO: 6 and encodes a functional translation initiation factor eIF(iso)4E protein, and the virus is a strain of Potato virus Y, wherein said strain breaks resistance of Virgin A mutant tobacco plants.

8. The virus-resistant tobacco plant according to claim 1, in which an expression level of a translation initiation factor eIF(iso)4E gene is 20% or lower as compared to a wild type.

9. The virus-resistant tobacco plant according to claim 8, wherein the expression level is 10% or lower as compared to the wild type.

10. The virus-resistant tobacco according to claim 8, wherein the virus-resistant tobacco retains an RNAi construct for suppressing expression of the translation initiation factor eIF(iso)4E gene.

11. A method for producing a virus-resistant tobacco plant, comprising introducing a mutation to a translation initiation factor eIF(iso)4E gene, the mutation causing production of a translation initiation factor eIF(iso)4E protein with suppressed eIF(iso)4E gene function, in order to produce a tobacco plant having resistance to a virus, the mutation being one or more mutations in (a) a translation initiation factor eIF(iso)4E gene encoding a translation initiation factor eIF(iso)4E protein consisting of an amino acid sequence represented by SEQ ID NO: 3 or SEQ ID NO: 4, (b) a translation initiation factor eIF(iso)4E gene encoding a functional translation initiation factor eIF(iso)4E protein having a sequence identity of 92% or higher with the amino acid sequence represented by SEQ ID NO: 3 or SEQ ID NO: 4, (c) a translation initiation factor eIF(iso)4E gene which causes production of mRNA consisting of a base sequence represented by SEQ ID NO: 5 or SEQ ID NO: 6, or (d) a translation initiation factor eIF(iso)4E gene encoding a functional translation initiation factor eIF(iso)4E protein which causes production of mRNA having a sequence identity of 92% or higher with the base sequence represented by SEQ ID NO: 5 or SEQ ID NO: 6, the virus being a strain of Potato virus Y, wherein said strain breaks virus resistance of Virgin A mutant of a tobacco plant, or the virus being Tobacco bushy top virus.

12. The method according to claim 11, wherein the mutation is a nonsense mutation.

13. The method according to claim 11, wherein the mutation is caused by ethyl methane sulfonate.

14. The method according to claim 11, wherein the mutation is one or more of the following mutations (1) to (4): (1) C of codon CAA is substituted by T; (2) C of codon CGA is substituted by T; (3) C of codon CAG is substituted by T; and (4) G (either one or both of two Gs) of codon TGG is substituted by A, in (a) an exon of a wild-type translation initiation factor eIF(iso)4E gene which encodes a translation initiation factor eIF(iso)4E protein consisting of an amino acid sequence represented by SEQ ID NO: 3 or SEQ ID NO: 4, (b) an exon of a translation initiation factor eIF(iso)4E gene which encodes a functional translation initiation factor eIF(iso)4E protein having a sequence identity of 92% or higher with the amino acid sequence represented by SEQ ID NO: 3 or SEQ ID NO: 4, (c) an exon of a translation initiation factor eIF(iso)4E gene which causes production of mRNA consisting of a base sequence represented by SEQ ID NO: 5 or SEQ ID NO: 6, or (d) an exon of a translation initiation factor eIF(iso)4E gene which causes production of mRNA having a sequence identity of 92% or higher with the base sequence represented by SEQ ID NO: 5 or SEQ ID NO: 6 and encodes a functional translation initiation factor eIF(iso)4E protein.

15. The method according to claim 11, wherein the mutation is one or more of the following mutations (1) to (27): (1) C to T substitution at position 270, (2) G to A substitution at position 295, (3) G to A substitution at position 296, (4) G to A substitution at position 304, (5) G to A substitution at position 305, (6) C to T substitution at position 315, (7) C to T substitution at position 330, (8) G to A substitution at position 343, (9) G to A substitution at position 344, (10) C to T substitution at position 357, (11) G to A substitution at position 394, (12) G to A substitution at position 395, (13) C to T substitution at position 1740, (14) G to A substitution at position 1813, (15) G to A substitution at position 1814, (16) G to A substitution at position 1846, (17) G to A substitution at position 1847, (18) G to A substitution at position 1888, (19) G to A substitution at position 1889, (20) C to T substitution at position 2050, (21) C to T substitution at position 2104, (22) G to A substitution at position 2123, (23) G to A substitution at position 2124, (24) C to T substitution at position 2152, (25) G to A substitution at position 4742, (26) G to A substitution at position 4743, and (27) C to T substitution at position 4926, in a translation initiation factor eIF(iso)4E gene consisting of a base sequence represented by SEQ ID NO: 7 in genomic DNA.

16. The method according to claim 11, wherein the mutation is one or more of the following mutations (1) to (26): (1) C to T substitution at position 264, (2) G to A substitution at position 289, (3) G to A substitution at position 290, (4) G to A substitution at position 298, (5) G to A substitution at position 299, (6) C to T substitution at position 315, (7) G to A substitution at position 328, (8) G to A substitution at position 329, (9) C to T substitution at position 342, (10) G to A substitution at position 379, (11) G to A substitution at position 380, (12) C to T substitution at position 1630, (13) G to A substitution at position 1703, (14) G to A substitution at position 1704, (15) G to A substitution at position 1736, (16) G to A substitution at position 1737, (17) G to A substitution at position 1778, (18) G to A substitution at position 1779, (19) C to T substitution at position 1940, (20) C to T substitution at position 1994, (21) G to A substitution at position 2013, (22) G to A substitution at position 2014, (23) C to T substitution at position 2042, (24) G to A substitution at position 3224, (25) G to A substitution at position 3225, and (26) C to T substitution at position 3406, in a translation initiation factor eIF(iso)4E gene consisting of a base sequence represented by SEQ ID NO: 8 in genomic DNA.

17. The method according to claim 11, wherein the virus is a strain of Potato virus Y, wherein said strain breaks resistance of Virgin A mutant of tobacco plants.

18. The method according to claim 11, wherein the virus is Tobacco bushy top virus.

* * * * *